United States Patent [19]

Stevenson

[11] Patent Number: 5,091,405
[45] Date of Patent: Feb. 25, 1992

[54] INSECTICIDAL PYRAZOLINES

[75] Inventor: Thomas M. Stevenson, Newark, Del.

[73] Assignee: E. I. Du Pont de Nemours and Company, Wilmington, Del.

[21] Appl. No.: 378,529

[22] PCT Filed: Jan. 4, 1988

[86] PCT No.: PCT/US88/00001
§ 371 Date: May 12, 1989
§ 102(e) Date: May 12, 1989

[87] PCT Pub. No.: WO88/05046
PCT Pub. Date: Jul. 14, 1988

Related U.S. Application Data

[63] and a continuation-in-part of Ser. No. 113,530, Oct. 28, 1987, abandoned.

[51] Int. Cl.$^5$ .................... C07D 231/06; A01N 43/56
[52] U.S. Cl. .................... 514/403; 548/379; 544/82; 544/130; 544/140; 546/187; 546/211; 514/232.2; 514/236.5; 514/316; 514/326
[58] Field of Search ............. 548/379; 544/82, 130, 544/140; 546/187, 211; 514/232.2, 236.5, 316, 326, 403

[56] References Cited

U.S. PATENT DOCUMENTS

| | | | |
|---|---|---|---|
| 3,753,978 | 8/1973 | Adelsberger et al. | 260/239.9 |
| 4,045,169 | 8/1977 | Mengler | 8/1 |
| 4,070,365 | 1/1978 | van Daalen et al. | 548/379 |
| 4,767,779 | 8/1988 | Duggan | 514/403 |

FOREIGN PATENT DOCUMENTS

| | | |
|---|---|---|
| 153127 | 8/1985 | European Pat. Off. |
| 232119 | 8/1987 | European Pat. Off. |

OTHER PUBLICATIONS

Vaughan, J. Org. Chem., 20 (1955), pp. 1619–1626.
Hassaneen et al., J. Heterocyclic Chem., 21 (1984), pp. 1013–1016.
Tewari et al., J. Chem. Eng. Data, vol. 28, 2 (1983), pp. 281–282.
Stecher et al., J. Org. Chem., 30, 1800 (1965).
Hill et al., Illinois State Acad. Sci., Trans, (1941), 112.
Shimizu et al., Bull. Chem. Soc. Jpn., 57, p. 787 (1984).
Padwa et al., J. Org. Chem. vol. 48, 19, (1983), p. 3191.
Huisgen et al., Monatsheltr fur Chemie, 98, 1618 (1967).
Kheruze et al., Zh. Org. Khim. 14, 1396 (1978).
Tewari et al., Tetrahedron 39, 129 (1983).
Gaudiano et al., Chem. Abst. 69, 27327y (1968).
Ezmirly et al., J. Heterocyclic Chem., 25, 257 (1988).
Meyer et al., Chemical Abstracts, vol. 52, Entry 7274c (1958).

Primary Examiner—John M. Ford
Attorney, Agent, or Firm—James A. Costello

[57] ABSTRACT

Pyrazolines and their intermediates, including all geometric and stereoisomers of the pyrazolines and intermediates, agricultural compositions containing the pyrazolines, and methods for use as insecticides.

21 Claims, No Drawings

INSECTICIDAL PYRAZOLINES

This U.S. application is a continuation of PCT/US88/0001, filed on Jan. 4, 1988, which was a continuation-in-part of U.S. applications 07/000,326, filed on Jan. 5, 1987, and 07/113,530, filed on Oct. 28, 1987, both now abandoned.

BACKGROUND OF THE INVENTION

Vaughan, *J. Org. Chem.*, 20 (1955), pages 1619 to 1626, discloses 1,5-diphenyl-2-pyrazoline-3-carboxamide. No utility is given for the disclosed compound which, in any event, does not suggest a compound of the instant invention.

U.S. Pat. No. 4,070,365 discloses insecticidal compounds of the formula

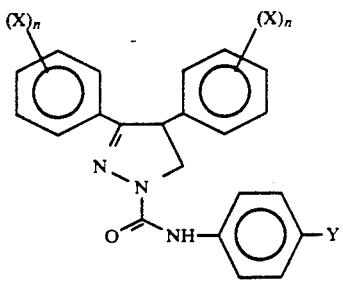

wherein X is halogen, and Y is halogen, $NO_2$ or alkyl.

EP 153,127 discloses insecticidal compounds of the formula

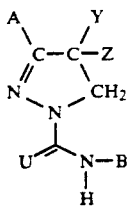

wherein
- A is unsubstituted or substituted phenyl;
- B is unsubstituted or substituted phenyl;
- U is O, S or NR;
- Y is alkyl, unsubstituted or substituted phenyl, or C(X)G;
- Z is H, cycloalkyl, unsubstituted or substituted phenyl $R^4$-Q;
- X is O or S; and
- G and $R^4$-Q are broadly defined.

Harhash et al., *J. Heterocyclic Chem.*, 21 (1984), at page 1013, discloses the preparation of five pyrazoline compounds, none of which is disclosed in the instant application. No utility is given for any of said compounds:

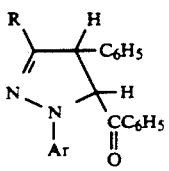

where R/Ar are $C_6H_5/C_6H_5$; $CO_2C_2H_5/C_6H_5$; $C(O)NHC_6H_5/C_6H_5$; $CH=CHC_6H_5/C_6H_5$; and $CH_3/4-NO_2-C_6H_4$.

SUMMARY OF THE INVENTION

This invention concerns certain 4,5-dihydro-1H-pyrazole-3-carboxamides (hereinafter referred to as pyrazolines) and intermediates to said compounds, including all geometric and stereoisomers of the pyrazolines and the intermediates. This invention also concerns agricultural compositions comprising at least one of said pyrazolines as active ingredient and an agriculturally suitable carrier therefor. This invention also concerns a method for controlling insects comprising contacting them or their environment with an effective amount of a pyrazoline of this invention.

More specifically, this invention pertains to pyrazolines of Formula I and agriculturally suitable salts thereof:

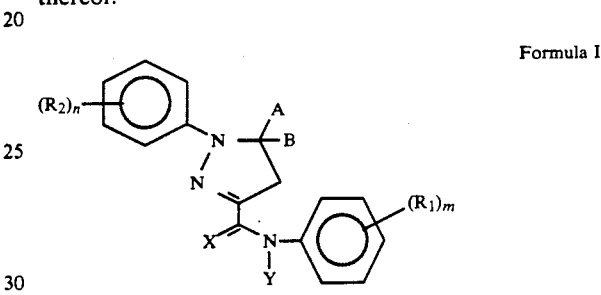

Formula I wherein:
- X is O or S;
- Y is H, $C_1$ to $C_4$ alkyl, $C_2$ to $C_4$ alkoxyalkyl, $C_1$ to $C_4$ alkylthio, $C_1$ to $C_4$ haloalkylthio, phenylthio, or phenylthio substituted with 1 to 3 substituents independently selected from W, $C_2$ to $C_4$ alkoxycarbonyl, C(O)H, $C_2$ to $C_4$ alkylcarbonyl or $C_2$ to $C_4$ haloalkylcarbonyl;
- A is H, $C_1$ to $C_6$ alkyl, phenyl, phenyl substituted by $(R_5)_p$, CN, $CO_2R_3$, $C(O)R_3$, $C(O)NR_3R_4$, $C(S)NR_3R_4$, $C(S)R_3$ or $C(S)SR_3$;
- B is H, $C_1$ to $C_6$ alkyl, $C_1$ to $C_6$ haloalkyl, $C_2$ to $C_6$ alkoxyalkyl, $C_2$ to $C_6$ cyanoalkyl, $C_3$ to $C_8$ alkoxycarbonylalkyl, $C_2$ to $C_6$ alkenyl, $C_2$ to $C_6$ alkynyl, $C_2$ to $C_6$ alkoxycarbonyl, phenyl, phenyl substituted with 1 to 3 substituents independently selected from W, benzyl or benzyl substituted with 1 to 3 substituents independently selected from W;
- W is halogen, CN, $NO_2$, $C_1$ to $C_2$ alkyl, $C_1$ to $C_2$ haloalkyl, $C_1$ to $C_2$ alkoxy, $C_1$ to $C_2$ haloalkoxy, $C_1$ to $C_2$ alkylthio, $C_1$ to $C_2$ haloalkylthio, $C_1$ to $C_2$ alkylsulfonyl or $C_1$ to $C_2$ haloalkylsulfonyl;
- $R_1$, $R_2$ and $R_5$ are independently $R_3$, halogen, CN, $N_3$, SCN, $NO_2$, $OR_3$, $SR_3$, $S(O)R_3$, $S(O)_2R_3$, $OC(O)R_3$, $OS(O)_2R_3$, $CO_2R_3$, $C(O)R_3$, $C(O)NR_3R_4$, $S(O)_2NR_3R_4$, $NR_3R_4$, $NR_4C(O)R_3$, $OC(O)NHR_3$, $NR_4C(O)NHR_3$, $NR_4S(O)_2R_3$, or when m, n or p is 2, $R_1$, $R_2$ or $R_5$ can be taken together as $-OCH_2O-$, $-OCF_2O-$, $-OCH_2CH_2O-$, $-CH_2C(CH_3)_2O-$, $-OCF_2CF_2O-$, or $-CF_2CF_2O-$ to form a cyclic bridge; provided $R_1$ is other than H;
- $R_3$ is H, $C_1$ to $C_4$ alkyl, $C_1$ to $C_4$ haloalkyl, $C_2$ to $C_4$ alkenyl, $C_2$ to $C_4$ haloalkenyl, $C_2$ to $C_4$ alkynyl, $C_2$ to $C_4$ haloalkynyl, $C_2$ to $C_4$ alkoxyalkyl, $C_2$ to $C_4$ alkylthioalkyl, $C_1$ to $C_4$ nitroalkyl, $C_2$ to $C_4$ cyanoalkyl, $C_3$ to $C_6$ alkoxycarbonylalkyl, $C_3$ to $C_6$ cycloalkyl, $C_3$ to $C_6$ halocycloalkyl, phenyl, benzyl, or phenyl or benzyl substituted with 1 to 3 substituents independently selected from W;

$R_4$ is H or $C_1$ to $C_4$ alkyl, or when $R_3$ and $R_4$ are attached to a single nitrogen atom, they can be taken together as $CH_{2\ 4}$, $CH_{2\ 5}$ or $CH_2CH_2OCH_2CH_2$;

m is 1 to 3;

n is 0 to 3; and p is 0 to 3.

In the above definitions, the term "alkyl", used either alone or in compound words such as "alkylthio" or "haloalkyl", means straight chain or branched alkyl such as methyl, ethyl, n-propyl, isopropyl or the different butyl, pentyl, hexyl isomers.

Alkoxy includes methoxy, ethoxy, n-propyloxy, isopropyloxy and the different butoxy or pentoxy isomers.

Alkenyl includes straight chain or branched alkenes, such as vinyl, 1-propenyl, 2-propenyl, 3-propenyl and the different butenyl, pentenyl and hexenyl isomers.

Alkynyl includes straight chain or branched alkynes, such as ethynyl, 1-propynyl, 2-propynyl and the different butynyl, pentynyl and hexynyl isomers.

Alkylthio includes methylthio, ethylthio and the different propylthio and butylthio isomers.

Alkylsulfonyl and the like are used analogously to the above examples.

Cycloalkyl includes cyclopropyl, cyclobutyl, cyclopentyl and cyclohexyl.

The term "halogen", either alone or in compound words such as "haloalkyl", means fluorine, chlorine, bromine or iodine. Further, when used in compound words such as "haloalkyl" said alkyl can be partially or fully substituted with halogen atoms, which may be the same or different. Examples of haloalkyl include $CH_2CH_2F$, $CF_2CF_2H$ and $CH_2CHFCl$. The terms "halocycloalkyl", "haloalkenyl" and "haloalkynyl" are used analogously to "haloalkyl".

The total number of carbon atoms in a substituent group is indicated by the "$C_i$ to $C_j$" prefix where i and j are numbers from 1 to 8. For example, $C_1$ to $C_3$ alkylsulfonyl would designate methylsulfonyl through propylsulfonyl; $C_2$ alkoxyalkoxy would designate $OCH_2OCH_3$; $C_4$ alkoxyalkoxy would designate the various isomers of an alkoxy group substituted with a second alkoxy group containing a total of 4 carbon atoms, examples including $OCH_2OCH_2CH_2CH_3$ and $OCH_2CH_2OCH_2CH_3$; $C_2$ cyanoalkyl would designate $CH_2CN$ and $C_3$ cyanoalkyl would designate $CH_2CH_2CN$ and $CH(CN)CH_3$; $C_2$ alkylcarbonyl would designate $C(O)CH_3$ and $C_4$ alkylcarbonyl would include $C(O)CH_2CH_2CH_3$ and $C(O)CH(CH_3)_2$; and as a final example, $C_3$ alkoxycarbonylalkyl would designate $CH_2CO_2CH_3$ and $C_4$ alkoxycarbonylalkyl would include $CH_2CH_2CO_2CH_3$, $CH_2CO_2CH_2CH_3$ and $CH(CH_3)CO_2CH_3$.

Preferred compounds (A) are those of Formula I wherein x is O;

Y is H, $CH_3$, $SCH_3$, $SCCl_3$, $SC_6H_5$, 2-$(NO_2)C_6H_4S$, $C(O)CH_3$, $C(O)H$, $C(O)CF_3$, $CO_2CH_3$ or $CO_2C_2H_5$;

$R_3$ is $C_1$ to $C_4$ alkyl, $C_1$ to $C_2$ haloalkyl, $C_2$ to $C_4$ alkenyl, $C_2$ to $C_4$ haloalkenyl, propargyl, phenyl, benzyl, or phenyl or benzyl substituted with one of F, Cl, Br, $CF_3$, $OCF_2H$, $OCF_3$ or $NO_2$;

n is 0 to 2;

p is 0 to 2; and m is 1 to 2.

Preferred compounds (B) are preferred compounds (A) wherein $R_1$ is halogen, CN, SCN, $NO_2$, $R_3$, $OR_3$, $SR_3$, $S(O)_2R_3$, $CO_2R_3$ or $C(O)R_3$, or when m is 2, $R_1$ can be taken together as $-OCF_2O-$, $-CH_2C(CH_3)_2O-$, $-OCF_2CF_2O-$ or $-CF_2CF_2O-$;

$R_2$ and $R_5$ are independently halogen, CN, SCN, $NO_2$, $R_3$, $OR_3$, $SR_3$, $S(O)_2R_3$, $OC(O)R_3$, $OS(O)_2R_3$, $CO_2R_3$, $C(O)R_3$, $C(O)NR_3R_4$, $S(O)_2NR_3R_4$ or $NR_3R_4$;

$R_3$ is $C_1$ to $C_4$ alkyl, $C_1$ to $C_2$ haloalkyl, $C_2$ to $C_4$ alkenyl, $C_2$ to $C_4$ haloalkenyl or propargyl;

$R_4$ is H or $C_1$ to $C_2$ alkyl;

A is $C_1$ to $C_4$ alkyl, phenyl, phenyl substituted with $(R_5)_p$, $CO_2R_3$, $C(O)R_3$, $C(O)NR_3R_4$ or $C(O)NR_4$-phenyl said phenyl optionally substituted with F, Cl, Br, $CF_3$, $OCF_2H$, $OCF_3$ or $NO_2$; and B is H, $C_1$ to $C_4$ alkyl, $C_1$ to $C_4$ haloalkyl, or $C_3$ to $C_4$ alkenyl.

Preferred compounds (C) are preferred compounds (B) wherein

Y is H, $CH_3$, $C(O)CH_3$ or $CO_2CH_3$;

m is 1 or 2 and one substituent is in the 4-position of the phenyl ring;

n is 1 or 2 and one substituent is in the 4-position of the phenyl ring;

p is 1 or 2 and one substituent is in the 3 or 4-position of the phenyl ring;

$R_1$ is F, Cl, Br, $CF_3$, $OCF_2H$, $OCF_3$ or CN, or when m is 2, $R_1$ can be taken together as $-CH_2C(CH_3)_2O-$ or $-CF_2CF_2O-$;

$R_2$ is F, Cl, Br, CN, $NO_2$, $CF_3$, $CH_3$, $OCH_3$, $OCF_2H$, $OCF_3$, $SCH_3$, $SCF_2H$, $S(O)_2CH_3$ or $N(CH_3)_2$;

$R_5$ is F, Cl, Br, CN, $NO_2$, $CF_3$, $CH_3$, $OCH_3$, $OCF_2H$, $OCF_3$, $SCH_3$, $SCF_2H$, $S(O)_2CH_3$, $S(O)_2CF_2H$, $CO_2CH_3$, $C(O)NHCH_3$, $C(O)N(CH_3)_2$, $S(O)_2N(CH_3)_2$ or $N(CH_3)_2$;

A is phenyl or phenyl substituted with $(R_5)_p$; and

B is H or $CH_3$.

Preferred compounds (D) are preferred compounds (B) wherein

Y is H, $CH_3$, $C(O)CH_3$ or $CO_2CH_3$;

m is 1 or 2 and one substituent is in the 4-position of the phenyl ring;

n is 1 or 2 and one substituent is in the 4-position of the phenyl ring;

$R_1$ is F, Cl, Br, $CF_3$, $OCF_2H$, $OCF_3$ or CN, or when m is 2, $R_1$ can be taken together as $-CH_2C(CH_3)_2O-$ or $-CF_2CF_2O-$;

$R_2$ is F, Cl, Br, CN, $NO_2$, $CF_3$, $CH_3$, $OCH_3$, $OCF_2H$, $OCF_3$, $SCH_3$, $SCF_2H$, $S(O)_2CH_3$, $S(O)_2CF_2H$, $CO_2CH_3$, $C(O)NHCH_3$, $C(O)N(CH_3)_2$, $S(O)_2N(CH_3)_2$ or $N(CH_3)_2$;

A is $CO_2CH_3$, $CO_2C_2H_5$, $C(O)NHCH_3$ or $C(O)N(CH_3)_2$; and

B is $CH_3$.

Especially preferred compounds are:

(E) A compound of (D): Methyl 1-(4-chlorophenyl)-4,5-dihydro5-methyl-3-[[4-(trifluoromethyl)phenyl]aminocarbonyl]-1H-pyrazole-5-carboxylate.

(F) A compound of (C): 1-(4-chlorophenyl)-5-(4-fluorophenyl)-4,5-dihydro-N-[4-(trifluoromethyl)phenyl]-1H-pyrazole-3-carboxamide.

(G) A compound of (C): 1,5-bis(4-chlorophenyl)-4,5-dihydro-N-[4-(trifluoromethyl)phenyl]-1H-pyrazole-3-carboxamide.

(H) A compound of (C): 1-(4-chlorophenyl)-5-(4-cyanophenyl)-4,5-dihydro-N-[4-(trifluoromethyl)phenyl]-1H-pyrazole-3-carboxamide.

This invention also pertains to compounds of Formula II which are useful as intermediates to prepare compounds of Formula I. The intermediates of this invention are:

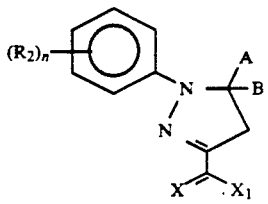

Formula II wherein:
X is O or S;
$X_1$ is OH, Cl or $C_1$ to $C_6$ alkoxy;
A is H, $C_1$ to $C_6$ alkyl, phenyl, phenyl substituted by $(R_5)_p$, CN, $CO_2R_3$, $C(O)R_3$, $C(O)NR_3R_4$, $C(S)NR_3R_4$, $C(S)R_3$ or $C(S)SR_3$;
B is H, $C_1$ to $C_6$ alkyl, $C_1$ to $C_6$ haloalkyl, $C_2$ to $C_6$ alkoxyalkyl, $C_2$ to $C_6$ cyanoalkyl, $C_3$ to $C_8$ alkoxycarbonylalkyl, $C_1$ to $C_6$ alkenyl, $C_1$ to $C_6$ alkynyl, $C_2$ to $C_6$ alkoxycarbonyl, phenyl, or phenyl substituted with 1 to 3 substituents independently selected from W. benzyl, benzyl substituted with 1 to 3 substituents independently selected from W;
W is halogen, CN, $NO_2$, $C_1$ to $C_2$ alkyl, $C_1$ to $C_2$ haloalkyl, $C_1$ to $C_2$ alkoxy, $C_1$ to $C_2$ haloalkoxy, $C_1$ to $C_2$ alkylthio, $C_1$ to $C_2$ haloalkylthio, $C_1$ to $C_2$ alkylsulfonyl or $C_1$ to $C_2$ haloalkylsulfonyl;
$R_2$ and $R_5$ are independently $R_3$, halogen, CN, $N_3$, SCN, $NO_2$, $OR_3$, $SR_3$, $S(O)R_3$, $S(O)_2R_3$, $OC(O)R_3$, $OS(O)_2R_3$, $CO_2R_3$, $C(O)NR_3R_4$, $S(O)_2NR_3R_4$, $NR_3R_4$, $NR_4C(O)R_3$, $OC(O)NHR_3$, $NR_4C(O)NHR_3$, $NR_4S(O)_2R_3$, or, when n or p is 2, $R_2$ or $R_5$ can be taken together as $-OCH_2O-$, $-OCF_2O-$, $-OCH_2CH_2O-$, $-CH_2C(CH_3)_2O-$, $-OCF_2CF_2O-$ or $-CF_2CF_2O-$ to form a cyclic bridge; except that both $R_2$ and $R_5$ are not H;
$R_3$ is H, $C_1$ to $C_4$ alkyl, $C_1$ to $C_4$ haloalkyl, $C_2$ to $C_4$ alkenyl, $C_2$ to $C_4$ haloalkenyl, $C_2$ to $C_4$ alkynyl, $C_2$ to $C_4$ haloalkynyl, $C_2$ to $C_4$ alkoxyalkyl, $C_2$ to $C_4$ alkylthioalkyl, $C_1$ to $C_4$ nitroalkyl, $C_2$ to $C_4$ cyanoalkyl, $C_3$ to $C_6$ alkoxycarbonylalkyl, $C_3$ to $C_6$ cycloalkyl, $C_3$ to $C_6$ halocycloalkyl, phenyl, benzyl, or phenyl or benzyl substituted with 1 to 3 substituents independently selected from W;
$R_4$ is H or $C_1$ to $C_4$ alkyl, or when $R_3$ and $R_4$ are attached to a single nitrogen atom, they can be taken together as $CH_2$ 4, $CH_2$ 5 or $CH_2CH_2OCH_2CH_2$;
n is 0 to 3; and
p is 0 to 3.

DETAILS OF THE INVENTION

Compounds of Formula I can be obtained by the reaction of activated carbonyl or thiocarbonyl compounds of Formula II with substituted anilines in the presence or absence of an acid acceptor or suitable condensing agent. Methods for performing this transformation are well known in the art; see, Zabicky. "The Chemistry of the Amides", Interscience, 1970.

One particularly useful method involves the chlorination of an acid derivative (II, $X_1=OH$) with thionyl chloride or another chlorinating agent followed by treatment with an aniline (III) in the presence of an acid acceptor such as an amine base, preferably triethylamine. Suitable solvents for the chlorination reaction are inert to hydrogen chloride and include benzene, toluene, and dichloromethane. Preferred temperatures for this process are from 20° to 100° C. with temperatures between 20° and 80° C. being particularly preferred. The latter reaction can be carried out in many different inert solvents such as dialkylethers, chlorinated hydrocarbons, and aromatic hydrocarbons. While temperatures at or below 25° C. are preferred, higher temperatures can also be employed. These reactions are normally run at atmospheric pressure, but can also be carried out at elevated pressures.

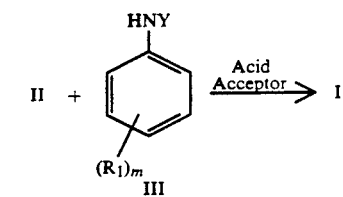

Esters of Formula II ($X_1=C_1$ to $C_6$ alkoxy) can be converted directly to compounds of Formula I in several ways. In the presence of Lewis acids such as AlMe$_3$, anilines react readily with esters of Formula II. The reaction is best carried out at room temperature to 120° C. Suitable solvents include dichloromethane, 1,2-dichloroethane, and toluene. The method described by Weinreb et al., *Organic Synthesis*, 59, 49, (1982), proceeds best with esters of lower alcohols such as methanol or ethanol.

Acids of Formula II ($X_1=OH$) can be converted directly to compounds of Formula I by use of coupling agents known in the peptide art in conjunction with anilines. Coupling agents include dicyclohexylcarbodiimide (DCC), N-hydroxysuccinimide, 2-chloro-N-methylpyridinium iodide, carbonyl diimidazole, or other agents capable of activating an acid function or acting as a dehydrating agent. These and other methods are described in Gross et al., "The Peptides," 3 Vols., Academic Press, New York, 1979 to 1981.

Compounds of Formula I can also be obtained from the cyclization of appropriate phenylhydrazines (V) with keto-acid derivatives (IV). It will be appreciated by those skilled in the art that this process applies equally to acids, esters, and anilides and further that the interconversion of these groups as discussed in the sequence (II→I) can be carried out after the cyclization reaction. The conditions for these reactions are well known in the art and described by Hill et al., *Trans. Illinois Acad. Sci.*, 33 (1940), 112 and by Vaughan, *J. Org. Chem.*, 20 (1955), 1619. The cyclization reaction is best carried out on an unsaturated keto-acid derivative (IV) in refluxing alcoholic media, in refluxing lower carboxylic acids, or in polar aprotic solvents such as dimethylformamide or dimethyl sulfoxide. Ethanol containing acetic acid or acetic acid alone are the preferred solvents although other protic or aprotic solvents and mixtures are also applicable. In some cases, phenyl hydrazones can be isolated prior to final cyclization and these can be refluxed further in order to complete the cyclization. While the unsaturated acid derivatives (IV)

are preferred, saturated compounds with a reactive group such as a halogen beta to the carbonyl can be employed in certain instances.

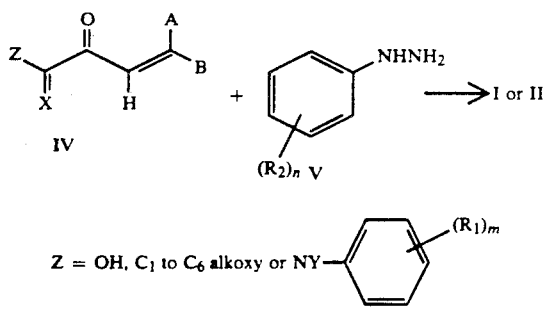

Compounds of Formula I and intermediates of Formula II can also be obtained by the dipolar cycloaddition reaction of nitrile-imines, generated from substituted phenylhydrazones of Formula VI, with appropriately substituted alkenes. The presence of an acid acceptor (generally an amine base, for example, triethylamine) is necessary for the formation of the nitrile-imine. In a typical reaction, the alkene is used in a two- to five-fold molar excess and the amine base in a three- to five-fold excess based on the hydrazone (VI). Suitable solvents include but are not restricted to benzene, toluene, 1,2-dichloroethane, chloroform, and tetrahydrofuran. The reaction can be carried out at temperatures ranging from 20° to 120° C. with the relative reactivity of the alkene (VII) governing the required temperature for a given example. The required hydrazones (VI) for the synthesis of compounds of Formula I and II can be prepared by methods known in the art or by modifications thereof; see, e.g., Shawali et al., *Tetrahedron*, 20 (1971), 2517.

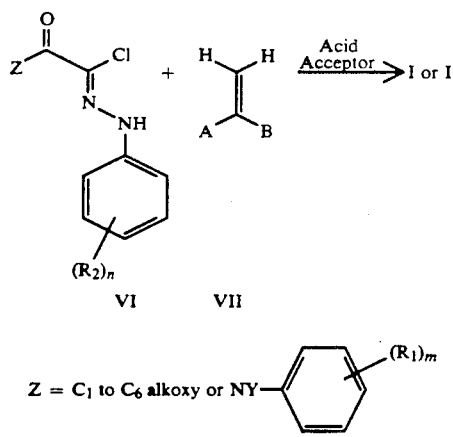

Some compounds of Formula I (Y=H) can be converted to other compounds of Formula I by alkylation, acylation, and sulphenylation reactions (Y=H). Reaction of compounds of Formula I in the presence of an acid acceptor with electrophilic agents (Y-leaving group) results in substitution on nitrogen. Strong bases such as sodium hydride, potassium t-butoxide, potassium hydride, and other bases known in the art to deprotonate amides are preferred in the process. Suitable electrophiles include, but are not restricted to alkyl halides, acyl halides, acid anhydrides, carbonates, chloroformates, disulphides, and sulphenyl halides. This reaction is normally run in the temperature range of 0°-25° C., but can be run at temperatures up to 120° C. if unreactive electrophiles are used. Solvents not deprotonated under the reactions conditions such as tetrahydrofuran, dimethylformamide, dimethoxyethane, and diethyl ether are preferred.

Compounds of Formula I (X=O) can be converted to compounds of Formula I (X=S) by means of thiating agents. Conversion of amides to thioamides is well known in the art. Phosphorous pentasulfide either alone or in combination with organic or inorganic bases is a preferred reagent to effect this conversion. When phosphorous pentasulfide is used alone, organic bases such as pyridine are the preferred solvents. When it is used in conjunction with inorganic bases such as sodium bicarbonate, the preferred solvents are ethers such as diglyme. Temperatures between 20° to 160° C. can be employed successfully with temperatures between 90° to 120° C. preferred. These and other means to convert amides to thioamides are described by Lapucha, *Synthesis* (1987), 256.

It will be appreciated by those skilled in the art that, regardless of the method of synthesis, compounds of Formula II can be converted to compounds of the instant invention by the methods described above. Many functional group transformations known to those skilled in the art can be employed to convert compounds of Formula I to new compounds of Formula I and that this will overcome any incompatibility of certain such groups with reagents and conditions disclosed above with respect to typical reaction mechanisms.

EXAMPLE 1

N-(4-Chlorophenyl)-2-[(4-chlorophenyl)amino]-2-oxoethanehydrozonoyl chloride

The compound, 4-chloroaniline (7.8 gm), was diazotized in 30 ml of 6N hydrochloric acid with sodium nitrite (4.5 gm) at 0° to 5° C. The resulting solution was added over twenty minutes by means of an insulated dropping funnel to a vigorously stirred mixture of 2,4'-dichloroacetoacetanilide (10 gm) and sodium acetate (15.1 gm) in ethanol (260 ml) held at 0° to 5° C. The suspension was stirred for 2 hours (temperature 20° C.) and filtered. The solid was dried by dissolution in dichloromethane and addition of magnesium sulfate. Filtration, evaporation of the solvent and trituration with butyl chloride provided the title compound (15.2 gm), m.p.: 180° to 181° C. NMR (CDCl$_3$) 8.5 (br, NH), 8.3 (br, NH), 7.6–7.1 (m, 8H).

EXAMPLE 2

N-(4-Chlorophenyl)-2-[4-(trifluoromethyl)phenyl]amino-2-oxoethanehydrazonoyl chloride Similarly prepared by the method of Example 1, 2-chloro-4'-trifluoromethylacetoacetanilide (8.6 gm) gave the title compound (3.8 gm), m.p.: 167° to 168.5° C. NMR (CDCl$_3$) 8.6 (br, NH), 8.3 (br, NH), 7.7–7.1 (m, 8H, ArH).

EXAMPLE 3

Methyl 1-(4-chlorophenyl)-3-[(4-chlorophenyl)aminocarbonyl]-4,5-dihydro-5-methyl-1H-pyrazole-5-carboxylate A sample of the compound of Example 1 (0.82 gm) was heated in refluxing benzene (15 ml) containing methyl methacrylate (4 ml). The resulting solution was treated dropwise with a solution of triethylamine (1.5 ml) in benzene (10 ml) and heated an additional 2 hours. The mixture was partitioned between ethyl acetate (50 ml) and 1N hydrochloric acid and the organic layer dried with magnesium sulfate. The organic residue was purified by silica gel chromatography with 20% ethyl acetate/hexanes followed by recrystallization from methanol to afford the title compound (0.62 gm); m.p.: 138° to 140° C. $^1$H NMR (CDCl$_3$) 8.4 (br, NH), 7.6–6.9 (m, ArH, 8H), 3.8 (s, CH$_3$, 3H); 3.7 (d, 1H, CH), 3.3 (d, 1H, CH), 1.7 (s, 3H, CH$_3$).

EXAMPLE 4

Methyl 1-(4-chlorophenyl)-4,5-dihydro-5-methyl-3-[[[4-(trifluoromethyl)phenyl]amino]carbonyl]-1H-pyrazole-5-carboxylate Analogous treatment of the compound of Example 2 (3.0 gm) under the conditions of Example 3 gave the title compound (2.0 gm); m.p. (MeOH): 178.5° to 180° C. NMR (CDCl$_3$) 8.5 (NH, br), 7.6–7.0 (m, 8H, ArH), 3.8 (s, CH$_3$, 3H), 3.7 (d, 1H, CH), 3.3 (d, 1H, CH), 1.7 (s, CH$_3$, 3H).

EXAMPLE 5

N,1-bis(4-chlorophenyl)-5-(4-cyanophenyl)-4,5-dihydro-1H-pyrazole-3-carboxamide

Repetition of Example 3 with 4-cyanostyrene (1.5 ml) on one-fifth the original scale gave the title compound (0.21 gm); m.p. (Ethanol): 183° to 186° C. NMR (CDCl$_3$) 8.5 (br, NH), 7.6–6.9 (m, 12H, ArH), 5.4 (dd, 1H, CH), 3.8 (dd, 1H, CH), 3.1 (dd, 1H, CH).

EXAMPLE 6

Ethyl chloro[2-(4-chlorophenyl)hydrazono]acetate

The compound, 4-chloroaniline (15.6 gm), was diazotized as described in Example 1 and repetition of that experiment with ethyl-2-chloroacetoacetate (16.5 ml) and sodium acetate (32 gm) gave the title compound (22.9 gm) as reddish needles after recrystallization from benzene: m.p.: 145° to 147.5° C. NMR (CDCl$_3$) 8.3 (1H, NH, br), 7.3–7.1 (m, 4H, ArH), 4.4 (q, 2H, OCH$_2$), 1.4 (t, 3H, CH$_3$).

EXAMPLE 7

Methyl chloro[2-(4-chlorophenyl)hydrazono]acetate

Similarly obtained by the method of Example 6 from methyl-2-chloroacetoacetate (29.5 gm), 4-chloroaniline (25 gm), and sodium acetate (51 gm) was the title compound (36.4 gm); m.p.: 149° to 150° C. NMR (CDCl$_3$) 8.3 (br, NH), 7.3 (m, 2H), 7.1 (m, 2H), 3.9 (s, 3H, CH$_3$).

EXAMPLE 8

Methyl chloro[2-(4-fluorophenyl)hydrazono]acetate

The title compound (16.4 gm) was obtained on repeating the procedure of Example 7 at 2/3 scale with 4-fluoroaniline (13.3 gm); m.p.: 110° to 113° C. NMR (CDCl$_3$) 8.34 (br, NH), 7.3–7.0 (m, 4H, ArH), 3.93 (s, CH$_3$, 3H).

EXAMPLE 9

Ethyl 1,5-bis(4-chlorophenyl)-4,5-dihydro-1H-pyrazole-3-carboxylate

The compound of Example 6 (5.0 gm) was heated in refluxing benzene (30 ml) containing 4-chlorostyrene (7.0 ml). Addition of a benzene (10 ml) solution of triethylamine(7.5 ml) was followed by one hour of continued heating. The cooled mixture was filtered, rotovapped, and dried on the vacuum pump to remove excess styrene. The residual solid was recrystallized from hexane/benzene (charcoal) to give the title compound (6.3 gm); m.p.: 128° to 130° C. NMR (CDCl$_3$) 7.3–6.9 (m, 8H, ArH), 5.4 (dd, 1H, CH), 4.3 (q, 2H, OCH$_2$), 3.8 (m, 1H, CH), 3.0 (m, 1H, CH), 1.38 (t, 3H, CH$_3$).

EXAMPLE 10

Ethyl 1,5-bis(4-Chlorophenyl)-4,5-dihydro-5-methyl-1H-pyrazole-3-carboxylate

The compound of Example 6 (1.0 gm) was converted to the title compound (0.6 gm) by adaptation of the procedure of Example 9 to 4-chloro-α-methyl styrene (2.5 ml). The product was a yellow oil. NMR (CDCl$_3$) 7.3–6.8 (m, ArH, 8H), 4.3 (q, 2H, CH$_2$), 3.3 (m, 2H, CH$_2$), 1.8 (s, 3H, CH$_3$), 1.3 (t, 3H, CH$_3$).

EXAMPLE 11

Dimethyl 1-(4-fluorophenyl)-4,5-dihydro-5-methyl-1H-pyrazole-3,5-dicarboxylate

A solution of the compound of Example 8 (5 gm) in ethyl acetate (30 ml) was treated with methyl methacrylate (10 ml) and triethylamine (6 ml). After stirring for 4 hours the reaction was partitioned between ethyl acetate (100 ml) and water (100 ml). The organic layer was washed with aqueous HCl (1N 100 ml), dried, and concentrated to leave the title compound (5 g): m.p.: 114°–118° C. NMR (CDCl$_3$) 7.26–7.0 (m, ArH, 4H) 3.88 (s, OMe, 3H), 3.77 (s, OMe, 3H), 3.5 (d, CH 1H), 3.2 (d, CH, 1H), 1.7 (s, Me, 3H).

EXAMPLE 12

1,5-bis(4-Chlorophenyl)-N-(4-fluorophenyl)-4,5-dihydro-1H-pyrazole-3-carboxamide The product of Example 9 (0.72 gm) was refluxed with 50% sodium hydroxide (1 ml) in 85% aqueous methanol (10 ml) for 2 hours. The mixture was acidified with 6N aqueous hydrochloric acid and partitioned between ethyl acetate and water. The ethyl acetate layer was dried with magnesium sulfate and concentrated to a yellow solid. The solid was suspended in benzene (20 ml) containing thionyl chloride (1.5 ml) and heated at reflux for 1.5 hour. The mixture was concentrated and azeotroped with toluene (10 ml) to give the oily acid chloride which was dissolved in tetrahydrofuran (15 ml) and treated dropwise with a benzene solution (10 ml) of triethylamine (1.0 ml) and 4-fluoroaniline (0.3 ml). The reaction mixture was stirred for 18 hours and partitioned between ethyl acetate and 1N hydrochloric acid. The organic layer was washed with sodium bicarbonate and brine. The dried organic layer (magnesium sulfate) was concentrated to leave a residue that could be purified by column chromatography or recrystallization from methanol. The title compound (0.46 g) was a yellow solid; m.p.: 194° to 195.5° C. NMR (CDCl₃) 8.5 (br, NH), 7.7–7.0 (m, 12H, ArH), 5.4 (m, 1H, CH), 3.8 (m, 1H, CH), 3.2 (m, 1H, CH).

EXAMPLE 13

1,5-Bis(4-chlorophenyl)-4,5-dihydro-N-[(4-trifluoromethyl)phenyl]-1H-pyrazole-3-carboxamide The title compound (6.3 g) was prepared by the method of Example 12 using 4-aminobenzotrifluoride (3.2 ml) and the compound of Example 9 (6.5 g). The compound was more conveniently prepared by omitting the acidification and extraction of the tetrahydrofuran solution. Simply evaporating the solvent and triturating the residue with methanol provided pure product as a powder: m.p.: 212.5°–214° C. NMR (CDCl₃) 8.6 (br, NH), 7.8–7.0 (m, ArH, 12H), 5.4 (dd, CH, 1H), 3.8 (dd, CH, 1H), 3.2 (dd, CH, 1H).

EXAMPLE 14

1,5-bis(4-Chlorophenyl)-4,5-dihydro-5-methyl-N-[(4-4-trifluoromethyl)phenyl]-1H-pyrazole-3-carboxamide Application of the procedure of Example 12 to the compound of Example 10 (0.60 g) and 4-trifluoromethylaniline (0.4 ml) gave the title compound (0.51 g) after silica gel chromatography in 20% ethyl acetate/hexanes and subsequent recrystallization from hexanes/butyl chloride; m.p.: 205° to 206° C. NMR (CDCl₃) 8.6 (br, NH), 7.8–6.9 (m, 12H, ArH), 3.4 (m, 2H, CH₂), 1.8 (s, 3H, CH₃).

EXAMPLE 15

Methyl 1-(4-fluorophenyl)-4,5-dihydro-3-[(4-iodophenyl)aminocarbonyl]-5-methyl-1H-pyrazole-5-carboxylate The compound of Example 11 (0.5 g) was dissolved in dichloromethane (5 ml) and added to a mixture of trimethylaluminum (2M in toluene, 1.68 ml) and 4-iodoaniline (0.7 g) in dichloromethane (10 ml). The mixture was stirred at room temperature for 16 hours and partitioned between 1N HCl (100 ml) and dichloromethane (100 ml). The organic layer was dried and evaporated to leave a solid. Recrystallization from ether/hexanes gave the title compound (0.73 g): m.p.: 84°–85° C. NMR (CDCl₃) 8.4 (br, NH), 7.7–6.9 (m, ArH, 12H), 3.8 (s, OMe, 3H), 3.8 (d, CH, 1H), 3.3 (d, CH, 1H), 1.7 (s, Me, 3H).

EXAMPLE 16

Potassium 4-(4-fluorophenyl)-2-oxo-3-butenoate

A solution of pyruvic acid and p-fluorobenzaldehyde (24.8 g) in methanol (20 ml) was cooled to 15° C. and treated with a solution of potassium hydroxide (16.8 g) in (50 ml) methanol. After ⅔ of the addition was complete, the cooling bath was removed and the temperature was allowed to rise to 40° C. A yellow precipitate appeared and was filtered after standing overnight. The solid was washed well with methanol and ether. The title compound (34.5 g) was used without further purification.

EXAMPLE 17

1-(3,4-Dichlorophenyl)-5-(4-fluorophenyl)-4,5-dihydro-N-[4-(trifluoromethyl)phenyl]-1H-pyrazole-3-carboxamide The compound of Example 16 (9.0 g) was treated with a solution of 3,4-dichlorophenylhydrazine hydrochloride (9.5 g) in water (100 ml). The orange solid was filtered and air dried. It was suspended in glacial acetic acid (150 ml) and refluxed for 3 hr. On cooling the pyrazoline acid crystallized (3.3 g). A second crop was also collected (1.1 g). The acid was suspended in benzene (100 ml) and treated with thionyl chloride (6 ml). The mixture was refluxed for 2 hr. and evaporated. The residue was dissolved in dry tetrahydrofuran (50 ml) and separated into five equal portions. One aliquot was added to a solution of 4-aminobenzotrifluoride (0.35 ml) and triethylamine (0.9 ml) in tetrahydrofuran (10 ml). The mixture was stirred for 30 min. and evaporated. The residue was triturated with methanol (10 ml) to give the title compound (0.9 g). m.p.: 241.5°–243° C. NMR (CDCl₃), 8.6 (m, NH), 7.8–6.7 (m, ArH, 11H), 5.4 (dd, 1H, CH), 3.8 (dd, 1H, CH), 3.2 (dd, 1H, CH).

EXAMPLE 18

4-(4-Fluorophenyl)-2-oxo-N-[4-(trifluoromethyl)phenyl]-3-butenamide

The compound of Example 16 was converted to the corresponding carboxylic acid by the general method of Stecher (J. Am. Chem. Soc., 1952, 74, 4392). The free acid (8.5 g) was treated with dichloromethylmethylether (10 ml) in 30 ml CH₂Cl₂. The mixture was heated at reflux with the evolution of HCl. Evaporation after 2 hr. gave the acid chloride which was dissolved in tetrahydrofuran (100 ml) and treated dropwise with a mixture of triethylamine (8 ml) and 4-aminobenzotrifluoride (4 ml) in tetrahydrofuran (25 ml). After 1 hr. the mixture was partitioned between 1N HCl and ethyl acetate. On standing overnight the ethyl acetate layer deposited the title compound (5 g). m.p.: 200°–201° C. NMR (CDCl₃), 9.2 (br, NH), 8.0–7.1 (m, Ar and CH₂, 10H).

EXAMPLE 19

4,5-Dihydro-4-(4-fluorophenyl)-1-phenyl-N-[4-(trifluoromethyl)phenyl]-1H-pyrazole-3-carboxamide The title compound (0.4 g) was obtained by heating the compound of Example 18 (0.6 g) and phenylhydrazine (0.2 ml) in dimethylformamide (5 ml) at reflux for 1 hr. The residue was purified by chromatography on silica gel (50 g) with hexanes/ethyl acetate (3:1) as eluent. m.p.: 183.5°–184.5° C. NMR (CDCl₃) 8.6 (br, NH), 7.8–7.0 (m, ArH, 13 H), 5.4 (m, 1H, CH), 3.8 (m, 1H, CH) 3.2 (m, 1H, CH).

EXAMPLE 20

1,5-Bis(4-chlorophenyl)-4,5-dihydro-N-methyl-N-[4-(trifluoromethyl)phenyl]-1H-pyrazole-3-carboxamide The compound of Example 13 (2.1 g) was added to a suspension of sodium hydride (60% in oil; 0.2 g) in dry tetrahydrofuran (25 ml). After 30 min. methyl iodide (0.9 g) was added in three separate portions. The mixture was stirred for 18 hr. and quenched with ammonium chloride solution. The mixture was extracted with ethyl acetate and the organic layer was dried and evaporated. The oily residue was chromatographed on silica gel with hexanes/ethyl acetate (3:1) as eluent to give the title compound (1.4 g): m.p.: 181°-183° C. NMR (CDCl₃) 7.8-6.9 (m, ArH, 10H), 6.26 (d, ArH, 2H), 5.15 (dd, CH, 1H), 3.8 (dd, CH, 1H), 3.5 (s, NMe, 3H), 3.15 (dd, CH, 1H).

EXAMPLE 21

N-acetyl-1,5-bis(4-chlorophenyl)-4,5-dihydro-N-[4-(trifluoromethyl)phenyl]-1H-pyrazole-3-carboxamide The title compound (0.8 g) was prepared by the method of Example 20 at ½ scale using acetic anhydride (0.5 ml) in place of methyl iodide. Purification by silica gel chromatography using hexanes/ethyl acetate (5:1) as eluent gave a solid which crystallized as bright yellow needles from methanol: m.p.: 158°-160° C. NMR (CDCl₃) 7.7-6.9 (m, ArH, 10H), 6.5 (d, ArH, 2H), 5.3 (dd, Ch, 1H), 3.7 (dd, CH, 1H), 3.05 (dd, CH, 1H), 2.5 (s, COMe, 3H).

EXAMPLE 22

Methyl 1-(4-chlorophenyl)-4,5-dihydro-5-methyl-3-[[[4-(trifluoromethyl)phenyl]amino]thioxomethyl]-1H-pyrazole-5-carboxylate The compound of Example 4 (0.67 g) was heated under reflux with phosphorous pentasulfide (1.1 g) and pyridine (3 ml) for 1 hr. The mixture was cooled and poured into saturated sodium bicarbonate solution (100 ml) and ethyl acetate (100 ml). The organic layer was washed with 1N hydrochloric acid (100 ml) and the aqueous layer was reextracted with ethyl acetate. The combined organic layers were dried, evaporated and chromatographed on silica gel with hexanes/ethyl acetate (1:1) to give an oil. The title compound (0.46 g) solidified on standing: m.p.: 76°-80° C. (dec.). NMR (CDCl₃) 8.1-7.0 (m, ArH, 8H), 3.8 (s, Me, 3H), 3.8 (d, CH, 1H), 3.5 (d, CH, 1H), 1.7 (s, Me, 3H).

Using the procedures of Examples 1 to 22 and the methods described herein, the following compounds of Tables 1 to 7 can be prepared.

Structures for Tables

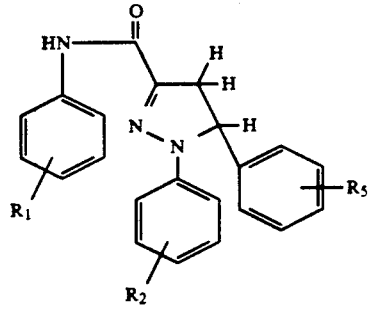

Table 1

-continued
Structures for Tables

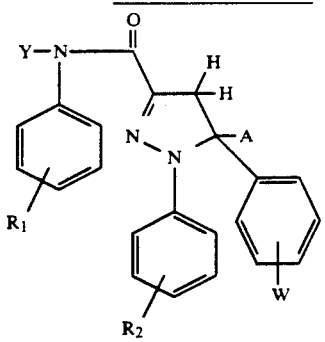

Table 2

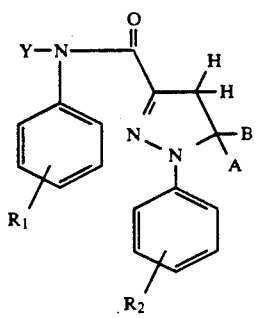

Table 3

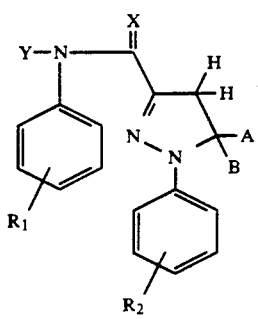

Table 4

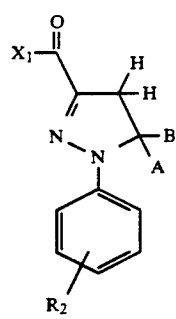

Table 5

TABLE 1

| R₁ | R₂ | R₅ | m.p. (°C.) |
|---|---|---|---|
| 4-CF₃ | 4-Cl | 4-CN | 160 to 164 |
| 4-CF₃ | 4-F | 4-CN | 188 to 190 |
| 4-CF₃ | 4-H | 4-CN | 194 to 195 |
| 4-CF₃ | 4-Br | 4-CN | |
| 4-CF₃ | 4-I | 4-CN | |
| 4-CF₃ | 4-OCF₃ | 4-CN | |
| 4-CF₃ | 4-CF₃ | 4-CN | |
| 4-CF₃ | 4-OCF₂H | 4-CN | |
| 4-CF₃ | 4-CF₂H | 4-CN | |
| 4-CF₃ | 4-Cl | 4-Cl | 212 to 214.5 |
| 4-CF₃ | 4-F | 4-Cl | 161 to 162.5 |
| 4-CF₃ | 4-H | 4-Cl | 200 to 201 |
| 4-CF₃ | 4-Br | 4-Cl | 227 to 229 |
| 4-CF₃ | 4-I | 4-Cl | |

TABLE 1-continued

| R₁ | R₂ | R₅ | m.p. (°C.) |
|---|---|---|---|
| 4-CF₃ | 4-OCF₃ | 4-Cl | |
| 4-CF₃ | 4-CF₃ | 4-Cl | 218 to 220 |
| 4-CF₃ | 4-OCF₂H | 4-Cl | 187 to 188 |
| 4-CF₃ | 4-CF₂H | 4-Cl | |
| 4-CF₃ | 4-Cl | 4-F | 213 to 214.5 |
| 4-CF₃ | 4-F | 4-F | 180.5 to 183 |
| 4-CF₃ | 4-H | 4-F | 183.5 to 184.5 |
| 4-CF₃ | 4-Br | 4-F | |
| 4-CF₃ | 4-I | 4-F | |
| 4-CF₃ | 4-OCF₃ | 4-F | 179 to 180 |
| 4-CF₃ | 4-CF₃ | 4-F | 201 to 202 |
| 4-CF₃ | 4-OCF₂H | 4-F | 176 to 178 |
| 4-CF₃ | 4-CF₂H | 4-F | |
| 4-CF₃ | 4-CN | 4-CN | 186 to 188 |
| 4-CF₃ | 4-CN | 4-Cl | |
| 4-CF₃ | 4-CN | 4-F | 221 to 222 |
| 4-CF₃ | 4-Cl | 4-H | |
| 4-CF₃ | 4-F | 4-H | 171 to 173 |
| 4-CF₃ | 4-H | 4-H | 213 to 214 |
| 4-CF₃ | 4-Br | 4-H | |
| 4-CF₃ | 4-CN | 4-H | |
| 4-CF₃ | 4-I | 4-H | |
| 4-CF₃ | 4-OCF₃ | 4-H | 176 to 178 |
| 4-CF₃ | 4-CF₃ | 4-H | |
| 4-CF₃ | 4-OCF₂H | 4-H | |
| 4-CF₃ | 4-CF₂H | 4-H | |
| 4-CF₃ | 4-Cl | 4-CH₃ | 185 to 186 |
| 4-CF₃ | 4-F | 4-CH₃ | |
| 4-CF₃ | 4-H | 4-CH₃ | |
| 4-CF₃ | 4-Br | 4-CH₃ | |
| 4-CF₃ | 4-CN | 4-CH₃ | |
| 4-CF₃ | 4-I | 4-CH₃ | |
| 4-CF₃ | 4-Cl | 3-Cl | 200 to 201 |
| 4-CF₃ | 4-F | 3-Cl | |
| 4-CF₃ | 4-H | 3-Cl | |
| 4-CF₃ | 4-Br | 3-Cl | |
| 4-CF₃ | 4-CN | 3-Cl | |
| 4-CF₃ | 4-OCF₃ | 3-Cl | |
| 4-CF₃ | 4-CF₃ | 3-Cl | |
| 4-CF₃ | 4-CF₂H | 3-Cl | |
| 4-CF₃ | 4-Cl | 3,4-di-F | 193.5 to 195 |
| 4-CF₃ | 4-F | 3,4-di-F | 171 to 173 |
| 4-CF₃ | 4-Br | 3,4-di-F | |
| 4-CF₃ | 4-H | 3,4-di-F | |
| 4-CF₃ | 4-CN | 3,4-di-F | |
| 4-CF₃ | 4-OCF₃ | 3,4-di-F | |
| 4-CF₃ | 4-OCF₂H | 3,4-di-F | |
| 4-CF₃ | 4-CF₃ | 3,4-di-F | |
| 4-CF₃ | 4-CF₂H | 3,4-di-F | |
| 4-CF₃ | 4-Cl | 3,4-di-Cl | 225 to 226 |
| 4-CF₃ | 4-F | 3,4-di-Cl | |
| 4-CF₃ | 4-Br | 3,4-di-Cl | |
| 4-CF₃ | 4-H | 3,4-di-Cl | |
| 4-CF₃ | 4-CN | 3,4-di-Cl | |
| 4-CF₃ | 4-OCF₃ | 3,4-di-Cl | |
| 4-CF₃ | 4-CF₃ | 3,4-di-Cl | |
| 4-CF₃ | 4-OCF₂H | 3,4-di-Cl | |
| 4-CF₃ | 4-CF₂H | 3,4-di-Cl | |
| 4-CF₃ | 4-Cl | 3-CN | |
| 4-CF₃ | 4-F | 3-CN | |
| 4-CF₃ | 4-Br | 3-CN | |
| 4-CF₃ | 4-H | 3-CN | |
| 4-CF₃ | 4-CN | 3-CN | 171 to 173 |
| 4-CF₃ | 4-CF₃ | 3-CN | |
| 4-CF₃ | 4-OCF₃ | 3-CN | |
| 4-CF₃ | 4-OCF₂H | 3-CN | |
| 4-CF₃ | 4-CF₂H | 3-CN | |
| 4-CF₃ | 4-Cl | 4-CO₂Me | 199 to 200 |
| 4-CF₃ | 4-F | 4-CO₂Me | 174 to 179 |
| 4-CF₃ | 4-Br | 4-CO₂Me | |
| 4-CF₃ | 4-H | 4-CO₂Me | |
| 4-CF₃ | 4-CN | 4-CO₂Me | |
| 4-CF₃ | 4-CF₃ | 4-CO₂Me | 208 to 210 |
| 4-CF₃ | 4-OCF₃ | 4-CO₂Me | |
| 4-CF₃ | 4-OCF₂H | 4-CO₂Me | |
| 4-CF₃ | 4-CF₂H | 4-CO₂Me | |
| 4-CF₃ | 4-Cl | 4-CF₃ | 194 to 196 |
| 4-CF₃ | 4-F | 4-CF₃ | |
| 4-CF₃ | 4-Br | 4-CF₃ | |
| 4-CF₃ | 4-H | 4-CF₃ | |
| 4-CF₃ | 4-CN | 4-CF₃ | 218 to 219 |
| 4-CF₃ | 4-CF₃ | 4-CF₃ | |
| 4-CF₃ | 4-OCF₃ | 4-CF₃ | |
| 4-CF₃ | 4-OCF₂H | 4-CF₃ | |
| 4-CF₃ | 4-CF₂H | 4-CF₃ | |
| 4-CF₃ | 4-Cl | 4-Br | 207 to 208 |
| 4-CF₃ | 4-F | 4-Br | |
| 4-CF₃ | 4-CN | 4-Br | 238 to 240 |
| 4-CF₃ | 4-CF₃ | 4-Br | 224 to 225 |
| 4-CF₃ | 4-H | 4-Br | |
| 4-CF₃ | 4-Cl | 3-Br | |
| 4-CF₃ | 4-F | 3-Br | |
| 4-CF₃ | 4-CF₃ | 3-Br | |
| 4-CF₃ | 4-CN | 3-Br | |
| 4-CF₃ | 4-H | 3-Br | |
| 4-OCF₃ | 4-Cl | 4-CN | |
| 4-OCF₃ | 4-F | 4-CN | |
| 4-OCF₃ | 4-Br | 4-CN | |
| 4-OCF₃ | 4-H | 4-CN | |
| 4-OCF₃ | 4-CN | 4-CN | |
| 4-OCF₃ | 4-CF₃ | 4-CN | |
| 4-OCF₃ | 4-OCF₃ | 4-CN | |
| 4-OCF₃ | 4-OCF₂H | 4-CN | |
| 4-OCF₃ | 4-CF₂H | 4-CN | |
| 4-OCF₃ | 4-Cl | 4-F | 165 to 167 |
| 4-OCF₃ | 4-F | 4-F | |
| 4-OCF₃ | 4-Br | 4-F | |
| 4-OCF₃ | 4-H | 4-F | |
| 4-OCF₃ | 4-CN | 4-F | |
| 4-OCF₃ | 4-CF₃ | 4-F | |
| 4-OCF₃ | 4-OCF₃ | 4-F | 140.5 to 142 |
| 4-OCF₃ | 4-OCF₂H | 4-F | 120 to 124 |
| 4-OCF₃ | 4-CF₂H | 4-F | |
| 4-OCF₃ | 4-Cl | 4-Cl | 170 to 172 |
| 4-OCF₃ | 4-F | 4-Cl | |
| 4-OCF₃ | 4-Br | 4-Cl | |
| 4-OCF₃ | 4-CN | 4-Cl | |
| 4-OCF₃ | 4-H | 4-Cl | |
| 4-OCF₃ | 4-CF₃ | 4-Cl | |
| 4-OCF₃ | 4-OCF₃ | 4-Cl | |
| 4-OCF₃ | 4-OCF₂H | 4-Cl | |
| 4-OCF₃ | 4-CF₂H | 4-Cl | |
| 4-OCF₃ | 4-Cl | 3-Cl | |
| 4-OCF₃ | 4-F | 3-Cl | |
| 4-OCF₃ | 4-Br | 3-Cl | |
| 4-OCF₃ | 4-H | 3-Cl | |
| 4-OCF₃ | 4-CN | 3-Cl | |
| 4-OCF₃ | 4-CF₃ | 3-Cl | |
| 4-OCF₃ | 4-OCF₃ | 3-Cl | |
| 4-OCF₃ | 4-OCF₂H | 3-Cl | |
| 4-OCF₃ | 4-CF₂H | 3-Cl | |
| 4-OCF₃ | 4-Cl | 4-H | |
| 4-OCF₃ | 4-F | 4-H | |
| 4-OCF₃ | 4-Br | 4-H | |
| 4-OCF₃ | 4-H | 4-H | |
| 4-OCF₃ | 4-CN | 4-H | |
| 4-OCF₃ | 4-CF₃ | 4-H | |
| 4-OCF₃ | 4-OCF₃ | 4-H | |
| 4-OCF₃ | 4-OCF₂H | 4-H | |
| 4-OCF₃ | 4-CF₂H | 4-H | |
| 4-OCF₃ | 4-Cl | 3,4-di-F | 134.5 to 135.5 |
| 4-OCF₃ | 4-F | 3,4-di-F | 162.5 to 164 |
| 4-OCF₃ | 4-Br | 3,4-di-F | |
| 4-OCF₃ | 4-H | 3,4-di-F | |
| 4-OCF₃ | 4-CN | 3,4-di-F | |
| 4-OCF₃ | 4-CF₃ | 3,4-di-F | |
| 4-OCF₃ | 4-OCF₃ | 3,4-di-F | |
| 4-OCF₃ | 4-OCF₂H | 3,4-di-F | |
| 4-OCF₃ | 4-CF₂H | 3,4-di-F | |
| 4-OCF₃ | 4-Cl | 4-CO₂Me | |
| 4-OCF₃ | 4-F | 4-CO₂Me | |
| 4-OCF₃ | 4-Br | 4-CO₂Me | |
| 4-OCF₃ | 4-H | 4-CO₂Me | |
| 4-OCF₃ | 4-CN | 4-CO₂Me | |
| 4-OCF₃ | 4-CF₃ | 4-CO₂Me | |
| 4-OCF₃ | 4-OCF₃ | 4-CO₂Me | |
| 4-OCF₃ | 4-OCF₂H | 4-CO₂Me | |
| 4-OCF₃ | 4-CF₂H | 4-CO₂Me | |
| 4-OCF₃ | 4-Cl | 4-CF₃ | |
| 4-OCF₃ | 4-F | 4-CF₃ | |
| 4-OCF₃ | 4-Br | 4-CF₃ | |

TABLE 1-continued

| R₁ | R₂ | R₅ | m.p. (°C.) |
|---|---|---|---|
| 4-OCF₃ | 4-H | 4-CF₃ | |
| 4-OCF₃ | 4-CN | 4-CF₃ | |
| 4-OCF₃ | 4-CF₃ | 4-CF₃ | |
| 4-OCF₃ | 4-OCF₃ | 4-CF₃ | |
| 4-OCF₃ | 4-OCF₂H | 4-CF₃ | |
| 4-OCF₃ | 4-CF₂H | 4-CF₃ | |
| 4-F | 4-Cl | 4-CN | |
| 4-F | 4-F | 4-CN | 174 to 175 |
| 4-F | 4-H | 4-CN | 204 to 207 |
| 4-F | 4-Br | 4-CN | |
| 4-F | 4-I | 4-CN | |
| 4-F | 4-CN | 4-CN | |
| 4-F | 4-Cl | 4-Cl | 194 to 195.5 |
| 4-F | 4-F | 4-Cl | 181 to 182 |
| 4-F | 4-H | 4-Cl | 201 to 202 |
| 4-F | 4-Br | 4-Cl | |
| 4-F | 4-I | 4-Cl | |
| 4-F | 4-CN | 4-Cl | |
| 4-F | 4-Cl | 4-F | 203 to 204 |
| 4-F | 4-F | 4-F | 157 to 158.5 |
| 4-F | 4-H | 4-F | |
| 4-F | 4-Br | 4-F | |
| 4-F | 4-I | 4-F | |
| 4-F | 4-CN | 4-F | 204 to 206 |
| 4-F | 4-Cl | 4-H | |
| 4-F | 4-F | 4-H | 168 to 169 |
| 4-F | 4-H | 4-H | |
| 4-F | 4-Br | 4-H | |
| 4-F | 4-I | 4-H | |
| 4-F | 4-CN | 4-H | 190 to 192 |
| 4-F | 4-Cl | 4-CH₃ | 170 to 171 |
| 4-F | 4-F | 4-CH₃ | |
| 4-F | 4-H | 4-CH₃ | |
| 4-F | 4-Br | 4-CH₃ | |
| 4-F | 4-I | 4-CH₃ | |
| 4-F | 4-CN | 4-CH₃ | |
| 4-Cl | 4-Cl | 4-CN | 180 to 183 |
| 4-Cl | 4-F | 4-CN | 169 to 170 |
| 4-Cl | 4-H | 4-CN | 178 to 179 |
| 4-Cl | 4-Br | 4-CN | |
| 4-Cl | 4-I | 4-CN | |
| 4-Cl | 4-CN | 4-CN | solid (a) |
| 4-Cl | 4-CF₃ | 4-CN | |
| 4-Cl | 4-OCF₃ | 4-CN | |
| 4-Cl | 4-OCF₂H | 4-CN | |
| 4-Cl | 4-CF₂H | 4-CN | |
| 4-Cl | 4-Cl | 4-Cl | 186 to 188 |
| 4-Cl | 4-F | 4-Cl | 137 to 139.5 |
| 4-Cl | 4-H | 4-Cl | |
| 4-Cl | 4-Br | 4-Cl | |
| 4-Cl | 4-I | 4-Cl | |
| 4-Cl | 4-CN | 4-Cl | |
| 4-Cl | 4-CF₃ | 4-Cl | 206 to 208 |
| 4-Cl | 4-OCF₃ | 4-Cl | |
| 4-Cl | 4-OCF₂H | 4-Cl | 173 to 175 |
| 4-Cl | 4-CF₂H | 4-Cl | |
| 4-Cl | 4-Cl | 4-F | 208 to 209.5 |
| 4-Cl | 4-F | 4-F | |
| 4-Cl | 4-H | 4-F | |
| 4-Cl | 4-Br | 4-F | |
| 4-Cl | 4-I | 4-F | |
| 4-Cl | 4-CN | 4-F | 215 to 218 |
| 4-Cl | 4-CF₃ | 4-F | |
| 4-Cl | 4-OCF₃ | 4-F | 181 to 183 |
| 4-Cl | 4-OCF₂H | 4-F | 175 to 176 |
| 4-Cl | 4-CF₂H | 4-F | |
| 4-Cl | 4-Cl | 4-H | |
| 4-Cl | 4-F | 4-H | 140 to 142 |
| 4-Cl | 4-H | 4-H | |
| 4-Cl | 4-Br | 4-H | |
| 4-Cl | 4-I | 4-H | |
| 4-Cl | 4-CN | 4-H | 202 to 203 |
| 4-Cl | 4-CF₃ | 4-H | 188 to 190 |
| 4-Cl | 4-OCF₃ | 4-H | |
| 4-Cl | 4-OCF₂H | 4-H | |
| 4-Cl | 4-CF₂H | 4-H | |
| 4-Cl | 4-Cl | 4-CH₃ | |
| 4-Cl | 4-F | 4-CH₃ | |
| 4-Cl | 4-H | 4-CH₃ | |
| 4-Cl | 4-Br | 4-CH₃ | |
| 4-Cl | 4-I | 4-CH₃ | |
| 4-Cl | 4-CN | 4-CH₃ | |
| 4-Cl | 4-CF₃ | 4-Cl | 206 to 208 |
| 4-Cl | 4-Cl | 3-Cl | 188 to 191 |
| 4-Cl | 4-F | 3-Cl | |
| 4-Cl | 4-H | 3-Cl | |
| 4-Cl | 4-Br | 3-Cl | |
| 4-Cl | 4-CN | 3-Cl | |
| 4-Cl | 4-OCF₃ | 3-Cl | |
| 4-Cl | 4-OCF₂H | 3-Cl | |
| 4-Cl | 4-CF₃ | 3-Cl | |
| 4-Cl | 4-CF₂H | 3-Cl | |
| 4-Cl | 4-Cl | 3,4-di-F | 148.5 to 151 |
| 4-Cl | 4-F | 3,4-di-F | 170 to 171 |
| 4-Cl | 4-Br | 3,4-di-F | |
| 4-Cl | 4-H | 3,4-di-F | |
| 4-Cl | 4-CN | 3,4-di-F | |
| 4-Cl | 4-OCF₃ | 3,4-di-F | |
| 4-Cl | 4-OCF₂H | 3,4-di-F | |
| 4-Cl | 4-CF₃ | 3,4-di-F | |
| 4-Cl | 4-CF₂H | 3,4-di-F | |
| 4-Cl | 4-Cl | 3,4-di-Cl | |
| 4-Cl | 4-F | 3,4-di-Cl | |
| 4-Cl | 4-Br | 3,4-di-Cl | |
| 4-Cl | 4-H | 3,4-di-Cl | |
| 4-Cl | 4-CN | 3,4-di-Cl | |
| 4-Cl | 4-OCF₃ | 3,4-di-Cl | |
| 4-Cl | 4-CF₃ | 3,4-di-Cl | |
| 4-Cl | 4-OCF₂H | 3,4-di-Cl | |
| 4-Cl | 4-CF₂H | 3,4-di-Cl | |
| 4-Cl | 4-Cl | 3-CN | |
| 4-Cl | 4-F | 3-CN | |
| 4-Cl | 4-Br | 3-CN | |
| 4-Cl | 4-H | 3-CN | |
| 4-Cl | 4-CN | 3-CN | |
| 4-Cl | 4-CF₃ | 3-CN | 168 to 170 |
| 4-Cl | 4-OCF₃ | 3-CN | |
| 4-Cl | 4-OCF₂H | 3-CN | |
| 4-Cl | 4-CF₂H | 3-CN | |
| 4-Cl | 4-Cl | 4-CO₂Me | 202 to 205 |
| 4-Cl | 4-F | 4-CO₂Me | 170 to 176 |
| 4-Cl | 4-Br | 4-CO₂Me | |
| 4-Cl | 4-H | 4-CO₂Me | |
| 4-Cl | 4-CN | 4-CO₂Me | |
| 4-Cl | 4-CF₃ | 4-CO₂Me | 175 to 178 |
| 4-Cl | 4-OCF₃ | 4-CO₂Me | |
| 4-Cl | 4-OCF₂H | 4-CO₂Me | |
| 4-Cl | 4-CF₂H | 4-CO₂Me | |
| 4-Cl | 4-Cl | 4-CF₃ | |
| 4-Cl | 4-F | 4-CF₃ | |
| 4-Cl | 4-Br | 4-CF₃ | |
| 4-Cl | 4-H | 4-CF₃ | |
| 4-Cl | 4-CN | 4-CF₃ | |
| 4-Cl | 4-CF₃ | 4-CF₃ | 177 to 178 |
| 4-Cl | 4-OCF₃ | 4-CF₃ | |
| 4-Cl | 4-OCF₂H | 4-CF₃ | |
| 4-Cl | 4-CF₂H | 4-CF₃ | |
| 4-Cl | 4-Cl | 4-Br | 191 to 193.5 |
| 4-Cl | 4-F | 4-Br | |
| 4-Cl | 4-CN | 4-Br | 246 to 248 |
| 4-Cl | 4-CF₃ | 4-Br | |
| 4-Cl | 4-H | 4-Br | |
| 4-Cl | 4-Cl | 3-Br | |
| 4-Cl | 4-F | 3-Br | |
| 4-Cl | 4-CF₃ | 3-Br | |
| 4-Cl | 4-CN | 3-Br | |
| 4-Cl | 4-H | 3-Br | |
| 4-Br | 4-F | 4-CN | |
| 4-Br | 4-Cl | 4-CN | 197.5 to 198.5 |
| 4-Br | 4-H | 4-CN | |
| 4-Br | 4-F | 4-Cl | |
| 4-Br | 4-Cl | 4-Cl | 190 to 192 |
| 4-Br | 4-H | 4-Cl | |
| 4-I | 4-F | 4-CN | |
| 4-I | 4-Cl | 4-CN | |
| 4-I | 4-H | 4-CN | |
| 4-I | 4-F | 4-Cl | |
| 4-I | 4-Cl | 4-Cl | 207.5 to 209 |
| 4-I | 4-H | 4-Cl | |
| 4-(4'-chlorophenoxy | 4-Cl | 4-Cl | 214 to 215.5 |
| 4-(4'-chloro- | 4-F | 4-CN | |

TABLE 1-continued

| R₁ | R₂ | R₅ | m.p. (°C.) |
|---|---|---|---|
| phenoxy | | | |
| 4-OCH₃ | 4-Cl | 4-CN | |
| 4-NO₂ | 4-Cl | 4-CN | 222 to 223 |
| 4-CO₂Et | 4-Cl | 4-CN | |
| 4-SMe | 4-Cl | 4-CN | |
| 4-SO₂Me | 4-Cl | 4-CN | |
| 4-Me | 4-Cl | 4-CN | |
| 4-CH=CH₂ | 4-Cl | 4-CN | |
| 4-C≡CH | 4-Cl | 4-CN | |
| 4-CONMe₂ | 4-Cl | 4-CN | |
| 4-SCF₃ | 4-Cl | 4-CN | |
| 4-OCH(CH₃)₂ | 4-Cl | 4-CN | |
| 4-OSO₂CH₃ | 4-Cl | 4-CN | |
| 4-OCOCH₃ | 4-Cl | 4-CN | |
| 4-NMe₂ | 4-Cl | 4-CN | |
| 4-NHCOCH₃ | 4-Cl | 4-CN | |
| 4-OCONHMe | 4-Cl | 4-CN | |
| 4-NHCONH₂ | 4-Cl | 4-CN | |
| 4-COCH₃ | 4-Cl | 4-CN | |
| 4-OCH₃ | 4-Cl | 4-Cl | 177 to 178 |
| 4-NO₂ | 4-Cl | 4-Cl | 223 to 225 |
| 4-CO₂Et | 4-Cl | 4-Cl | |
| 4-SMe | 4-Cl | 4-Cl | |
| 4-SO₂Me | 4-Cl | 4-Cl | |
| 4-Me | 4-Cl | 4-Cl | 153 to 155 |
| 4-CH=CH₂ | 4-Cl | 4-Cl | |
| 4-C≡CH | 4-Cl | 4-Cl | |
| 4-CONMe₂ | 4-Cl | 4-Cl | |
| 4-SCF₃ | 4-Cl | 4-Cl | |
| 4-OCH(CH₃)₂ | 4-Cl | 4-Cl | |
| 4-OSO₂CH₃ | 4-Cl | 4-Cl | |
| 4-OCOCH₃ | 4-Cl | 4-Cl | |
| 4-NMe₂ | 4-Cl | 4-Cl | |
| 4-NHCOCH₃ | 4-Cl | 4-Cl | |
| 4-OCONHMe | 4-Cl | 4-Cl | |
| 4-NHCONH₂ | 4-Cl | 4-Cl | |
| 4-COCH₃ | 4-Cl | 4-Cl | 193 to 195 |
| 4-OCH₃ | 4-F | 4-CN | |
| 4-NO₂ | 4-F | 4-CN | |
| 4-CO₂Et | 4-F | 4-CN | |
| 4-SMe | 4-F | 4-CN | |
| 4-SO₂Me | 4-F | 4-CN | |
| 4-Me | 4-F | 4-CN | |
| 4-CH=CH₂ | 4-F | 4-CN | |
| 4-C≡CH | 4-F | 4-CN | |
| 4-CONMe₂ | 4-F | 4-CN | |
| 4-SCF₃ | 4-F | 4-CN | |
| 4-OCH(CH₃)₂ | 4-F | 4-CN | |
| 4-OSO₂CH₃ | 4-F | 4-CN | |
| 4-OCOCH₃ | 4-F | 4-CN | |
| 4-NMe₂ | 4-F | 4-CN | |
| 4-NHCOCH₃ | 4-F | 4-CN | |
| 4-OCONHMe | 4-F | 4-CN | |
| 4-NHCONH₂ | 4-F | 4-CN | |
| 4-COCH₃ | 4-F | 4-CN | |
| 4-OCH₃ | 4-F | 4-Cl | |
| 4-NO₂ | 4-F | 4-Cl | 180 to 185 |
| 4-CO₂Et | 4-F | 4-Cl | |
| 4-SMe | 4-F | 4-Cl | |
| 4-SO₂Me | 4-F | 4-Cl | |
| 4-Me | 4-F | 4-Cl | |
| 4-CH=CH₂ | 4-F | 4-Cl | |
| 4-C≡CH | 4-F | 4-Cl | |
| 4-CONMe₂ | 4-F | 4-Cl | |
| 4-SCF₃ | 4-F | 4-Cl | |
| 4-OCH(CH₃)₂ | 4-F | 4-Cl | |
| 4-OSO₂CH₃ | 4-F | 4-Cl | |
| 4-OCOCH₃ | 4-F | 4-Cl | |
| 4-NMe₂ | 4-F | 4-Cl | |
| 4-NHCOCH₃ | 4-F | 4-Cl | |
| 4-OCONHMe | 4-F | 4-Cl | |
| 4-NHCONH₂ | 4-F | 4-Cl | |
| 4-COCH₃ | 4-F | 4-Cl | |
| 4-CF₃ | 4-F | 3-Cl, 4-CN | |
| 4-CF₃ | 4-Cl | 3-Cl, 4-CN | |
| 4-CF₃ | 4-F | 3-CN, 4-F | |
| 4-CF₃ | 4-Cl | 3-CN, 4-F | |
| 4-CF₃ | 4-F | 3-CN, 4-Cl | |
| 4-CF₃ | 4-Cl | 3-CN, 4-Cl | |
| 4-CF₃ | 4-F | 2-F, 4-CN | |
| 4-CF₃ | 4-Cl | 2-F, 4-CN | |

TABLE 1-continued

| R₁ | R₂ | R₅ | m.p. (°C.) |
|---|---|---|---|
| 4-CF₃ | 4-F | 2-F, 4-Cl | |
| 4-CF₃ | 4-Cl | 2-F, 4-Cl | |
| 4-CF₃ | 4-F | 2,4-di-F | |
| 4-CF₃ | 4-Cl | 2,4-di-F | |
| 4-CF₃ | 4-F | 3,5-di-F | |
| 4-CF₃ | 4-Cl | 3,5-di-F | |
| 4-CF₃ | 4-F | 2-Cl | |
| 4-CF₃ | 4-Cl | 2-Cl | |
| 4-CF₃ | 4-F | 3-F | |
| 4-CF₃ | 4-Cl | 3-F | |
| 4-CF₃ | 4-F | 2-F | |
| 4-CF₃ | 4-Cl | 2-F | |
| 4-CF₃ | 4-F | 2-CN | |
| 4-CF₃ | 4-Cl | 2-CN | |
| 4-CF₃ | 4-F | 3-CF₃ | |
| 4-CF₃ | 4-Cl | 3-CF₃ | |
| 4-CF₃ | 4-F | 2-CF₃ | |
| 4-CF₃ | 4-Cl | 2-CF₃ | |
| 4-CF₃ | 4-F | 3,4-di-CN | |
| 4-CF₃ | 4-Cl | 3,4-di-CN | |
| 4-CF₃ | 4-F | 3-F, 4-Cl | |
| 4-CF₃ | 4-Cl | 3-F, 4-Cl | |
| 4-CF₃ | 4-F | 3-Cl, 4-F | |
| 4-CF₃ | 4-Cl | 3-Cl, 4-F | |
| 4-CF₃ | 4-F | 3-F, 4-CN | |
| 4-CF₃ | 4-Cl | 3-F, 4-CN | |
| 4-CF₃ | 4-F | 3,5-di-Cl | |
| 4-CF₃ | 4-Cl | 3,5-di-Cl | |
| 4-CF₃ | 4-F | 3-Cl, 5-F | |
| 4-CF₃ | 4-Cl | 3-Cl, 5-F | |
| 4-CF₃ | 4-OCH₃ | 4-CN | |
| 4-CF₃ | 4-NO₂ | 4-CN | |
| 4-CF₃ | 4-CO₂Et | 4-CN | |
| 4-CF₃ | 4-SMe | 4-CN | |
| 4-CF₃ | 4-SO₂Me | 4-CN | |
| 4-CF₃ | 4-Me | 4-CN | |
| 4-CF₃ | 4-CH=CH₂ | 4-CN | |
| 4-CF₃ | 4-C≡CH | 4-CN | |
| 4-CF₃ | 4-CONMe₂ | 4-CN | |
| 4-CF₃ | 4-SCF₃ | 4-CN | |
| 4-CF₃ | 4-OCH(CH₃)₂ | 4-CN | |
| 4-CF₃ | 4-OSO₂CH₃ | 4-CN | |
| 4-CF₃ | 4-OCOCH₃ | 4-CN | |
| 4-CF₃ | 4-NMe₂ | 4-CN | |
| 4-CF₃ | 4-NHCOCH₃ | 4-CN | |
| 4-CF₃ | 4-OCONHMe | 4-CN | |
| 4-CF₃ | 4-NHCONH₂ | 4-CN | |
| 4-CF₃ | 4-COCH₃ | 4-CN | |
| 4-CF₃ | 4-OCH₃ | 4-F | |
| 4-CF₃ | 4-NO₂ | 4-F | 232 to 234 |
| 4-CF₃ | 4-CO₂Et | 4-F | |
| 4-CF₃ | 4-SMe | 4-F | |
| 4-CF₃ | 4-SO₂Me | 4-F | 242 to 244 |
| 4-CF₃ | 4-Me | 4-F | |
| 4-CF₃ | 4-CH=CH₂ | 4-F | |
| 4-CF₃ | 4-C≡CH | 4-F | |
| 4-CF₃ | 4-CONMe₂ | 4-F | |
| 4-CF₃ | 4-SCF₃ | 4-F | |
| 4-CF₃ | 4-OCH(CH₃)₂ | 4-F | |
| 4-CF₃ | 4-OSO₂CH₃ | 4-F | |
| 4-CF₃ | 4-OCOCH₃ | 4-F | |
| 4-CF₃ | 4-NMe₂ | 4-F | |
| 4-CF₃ | 4-NHCOCH₃ | 4-F | |
| 4-CF₃ | 4-OCONHMe | 4-F | |
| 4-CF₃ | 4-NHCONH₂ | 4-F | |
| 4-CF₃ | 4-COCH₃ | 4-F | |
| 4-CF₃ | 4-OCH₃ | 4-Cl | |
| 4-CF₃ | 4-NO₂ | 4-Cl | |
| 4-CF₃ | 4-CO₂Et | 4-Cl | |
| 4-CF₃ | 4-SMe | 4-Cl | |
| 4-CF₃ | 4-SO₂Me | 4-Cl | |
| 4-CF₃ | 4-Me | 4-Cl | 201.5 to 203.5 |
| 4-CF₃ | 4-CH=CH₂ | 4-Cl | |
| 4-CF₃ | 4-C≡CH | 4-Cl | |
| 4-CF₃ | 4-CONMe₂ | 4-Cl | |
| 4-CF₃ | 4-SCF₃ | 4-Cl | |
| 4-CF₃ | 4-OCH(CH₃)₂ | 4-Cl | |
| 4-CF₃ | 4-OSO₂CH₃ | 4-Cl | |
| 4-CF₃ | 4-OCOCH₃ | 4-Cl | |
| 4-CF₃ | 4-NMe₂ | 4-Cl | |
| 4-CF₃ | 4-NHCOCH₃ | 4-Cl | |

TABLE 1-continued

| R₁ | R₂ | R₅ | m.p. (°C.) |
|---|---|---|---|
| 4-CF₃ | 4-OCONHMe | 4-Cl | |
| 4-CF₃ | 4-NHCONH₂ | 4-Cl | |
| 4-CF₃ | 4-COCH₃ | 4-Cl | |
| 4-CF₃ | 4-OCH₃ | 4-CN | |
| 4-Cl | 4-NO₂ | 4-CN | |
| 4-Cl | 4-CO₂Et | 4-CN | |
| 4-Cl | 4-SMe | 4-CN | |
| 4-Cl | 4-SO₂Me | 4-CN | |
| 4-Cl | 4-Me | 4-CN | |
| 4-Cl | 4-CH=CH₂ | 4-CN | |
| 4-Cl | 4-C≡CH | 4-CN | |
| 4-Cl | 4-CONMe₂ | 4-CN | |
| 4-Cl | 4-SCF₃ | 4-CN | |
| 4-Cl | 4-OCH(CH₃)₂ | 4-CN | |
| 4-Cl | 4-OSO₂CH₃ | 4-CN | |
| 4-Cl | 4-OCOCH₃ | 4-CN | |
| 4-Cl | 4-NMe₂ | 4-CN | |
| 4-Cl | 4-NHCOCH₃ | 4-CN | |
| 4-Cl | 4-OCONHMe | 4-CN | |
| 4-Cl | 4-NHCONH₂ | 4-CN | |
| 4-Cl | 4-COCH₃ | 4-CN | |
| 4-Cl | 4-OCH₃ | 4-Cl | 188 to 189 |
| 4-Cl | 4-NO₂ | 4-Cl | |
| 4-Cl | 4-CO₂Et | 4-Cl | |
| 4-Cl | 4-SMe | 4-Cl | |
| 4-Cl | 4-SO₂Me | 4-Cl | |
| 4-Cl | 4-Me | 4-Cl | |
| 4-Cl | 4-CH=CH₂ | 4-Cl | |
| 4-Cl | 4-C≡CH | 4-Cl | |
| 4-Cl | 4-CONMe₂ | 4-Cl | |
| 4-Cl | 4-SCF₃ | 4-Cl | |
| 4-Cl | 4-OCH(CH₃)₂ | 4-Cl | |
| 4-Cl | 4-OSO₂CH₃ | 4-Cl | |
| 4-Cl | 4-OCOCH₃ | 4-Cl | |
| 4-Cl | 4-NMe₂ | 4-Cl | |
| 4-Cl | 4-NHCOCH₃ | 4-Cl | |
| 4-Cl | 4-OCONHMe | 4-Cl | |
| 4-Cl | 4-NHCONH₂ | 4-Cl | |
| 4-Cl | 4-COCH₃ | 4-Cl | |
| 4-Cl | 4-OCH₃ | 4-F | |
| 4-Cl | 4-NO₂ | 4-F | |
| 4-Cl | 4-CO₂Et | 4-F | |
| 4-Cl | 4-SMe | 4-F | |
| 4-Cl | 4-SO₂Me | 4-F | |
| 4-Cl | 4-Me | 4-F | |
| 4-Cl | 4-CH=CH₂ | 4-F | |
| 4-Cl | 4-C≡CH | 4-F | |
| 4-Cl | 4-CONMe₂ | 4-F | |
| 4-Cl | 4-SCF₃ | 4-F | |
| 4-Cl | 4-OCH(CH₃)₂ | 4-F | |
| 4-Cl | 4-OSO₂CH₃ | 4-F | |
| 4-Cl | 4-OCOCH₃ | 4-F | |
| 4-Cl | 4-NMe₂ | 4-F | |
| 4-Cl | 4-NHCOCH₃ | 4-F | |
| 4-Cl | 4-OCONHMe | 4-F | |
| 4-Cl | 4-NHCONH₂ | 4-F | |
| 4-Cl | 4-COCH₃ | 4-F | |
| 4-CF₃ | 4-Cl | 4-OCH₃ | 163 to 164 |
| 4-CF₃ | 4-Cl | 4-NO₂ | |
| 4-CF₃ | 4-Cl | 4-CO₂Et | |
| 4-CF₃ | 4-Cl | 4-SMe | |
| 4-CF₃ | 4-Cl | 4-SO₂Me | |
| 4-CF₃ | 4-Cl | 4-Me | |
| 4-CF₃ | 4-Cl | 4-CH=CH₂ | |
| 4-CF₃ | 4-Cl | 4-C≡CH | |
| 4-CF₃ | 4-Cl | 4-CONMe₂ | |
| 4-CF₃ | 4-Cl | 4-SCF₃ | |
| 4-CF₃ | 4-Cl | 4-OCH(CH₃)₂ | |
| 4-CF₃ | 4-Cl | 4-OSO₂CH₃ | |
| 4-CF₃ | 4-Cl | 4-OCOCH₃ | |
| 4-CF₃ | 4-Cl | 4-NMe₂ | |
| 4-CF₃ | 4-Cl | 4-NHCOCH₃ | |
| 4-CF₃ | 4-Cl | 4-OCONHMe | |
| 4-CF₃ | 4-Cl | 4-NHCONH₂ | |
| 4-CF₃ | 4-Cl | 4-COCH₃ | |
| 4-F | 4-F | 4-OCH₃ | |
| 4-F | 4-F | 4-NO₂ | |
| 4-F | 4-F | 4-CO₂Et | |
| 4-F | 4-F | 4-SMe | |
| 4-F | 4-F | 4-SO₂Me | |
| 4-F | 4-F | 4-Me | |
| 4-F | 4-F | 4-CH=CH₂ | |
| 4-F | 4-F | 4-C≡CH | |
| 4-F | 4-F | 4-CONMe₂ | |
| 4-F | 4-F | 4-SCF₃ | |
| 4-F | 4-F | 4-OCH(CH₃)₂ | |
| 4-F | 4-F | 4-OSO₂CH₃ | |
| 4-F | 4-F | 4-OCOCH₃ | |
| 4-F | 4-F | 4-NMe₂ | |
| 4-F | 4-F | 4-NHCOCH₃ | |
| 4-F | 4-F | 4-OCONHMe | |
| 4-F | 4-F | 4-NHCONH₂ | |
| 4-F | 4-F | 4-COCH₃ | |
| 4-Cl | 4-Cl | 4-OCH₃ | 166 to 168 |
| 4-Cl | 4-Cl | 4-NO₂ | |
| 4-Cl | 4-Cl | 4-CO₂Et | |
| 4-Cl | 4-Cl | 4-SMe | |
| 4-Cl | 4-Cl | 4-SO₂Me | |
| 4-Cl | 4-Cl | 4-Me | |
| 4-Cl | 4-Cl | 4-CH=CH₂ | |
| 4-Cl | 4-Cl | 4-C≡CH | |
| 4-Cl | 4-Cl | 4-CONMe₂ | |
| 4-Cl | 4-Cl | 4-SCF₃ | |
| 4-Cl | 4-Cl | 4-OCH(CH₃)₂ | |
| 4-Cl | 4-Cl | 4-OSO₂CH₃ | |
| 4-Cl | 4-Cl | 4-OCOCH₃ | |
| 4-Cl | 4-Cl | 4-NMe₂ | |
| 4-Cl | 4-Cl | 4-NHCOCH₃ | |
| 4-Cl | 4-Cl | 4-OCONHMe | |
| 4-Cl | 4-Cl | 4-NHCONH₂ | |
| 4-Cl | 4-Cl | 4-COCH₃ | |
| 3-F, 4-CF₃ | 4-Cl | 4-CN | |
| 3-Cl, 4-CF₃ | 4-Cl | 4-CN | |
| 2-F, 4-CF₃ | 4-Cl | 4-CN | |
| 2-Cl, 4-CF₃ | 4-Cl | 4-CN | |
| 3-F, 4-Cl | 4-Cl | 4-CN | |
| 3,4-di-F | 4-Cl | 4-CN | |
| 3-Cl, 4-F | 4-Cl | 4-CN | |
| 3,4-di-Cl | 4-Cl | 4-CN | |
| 4-F, 3-CF₃ | 4-Cl | 4-CN | |
| 4-Cl, 3-CF₃ | 4-Cl | 4-CN | |
| 5-F, 3-CF₃ | 4-F | 4-CN | |
| 5-Cl, 3-CF₃ | 4-F | 4-CN | |
| 3,5-di-F | 4-F | 4-CN | |
| 3,5-di-Cl | 4-F | 4-CN | |
| 3-F, 5-Cl | 4-F | 4-CN | |
| 3-CF₃ | 4-F | 4-CN | |
| 3-CF₃ | 4-Cl | 4-CN | |
| 3-Cl | 4-F | 4-CN | |
| 3-Cl | 4-Cl | 4-CN | |
| 3-F | 4-F | 4-CN | |
| 3-F | 4-Cl | 4-CN | |
| 4-CF₃ | 3-F | 4-CN | |
| 4-CF₃ | 3-Cl | 4-CN | |
| 4-CF₃ | 3-F, 4-Cl | 4-CN | |
| 4-CF₃ | 3-Cl, 4-F | 4-CN | |
| 4-CF₃ | 3,4-di-F | 4-CN | |
| 4-CF₃ | 3,4-di-Cl | 4-CN | |
| 4-CF₃ | 3,5-di-F | 4-CN | |
| 4-CF₃ | 3,5-di-Cl | 4-CN | |
| 4-CF₃ | 3-F, 5-Cl | 4-CN | |
| 4-CF₃ | 3,4,5-trifluoro | 4-CN | |
| 4-CF₃ | 3,4,5-trichloro | 4-CN | |
| 4-CF₃ | 2-F | 4-CN | |
| 4-CF₃ | 2-Cl | 4-CN | |
| 4-CF₃ | 2-F, 4-Cl | 4-CN | |
| 4-CF₃ | 2-Cl, 4-F | 4-CN | |
| 4-CF₃ | 2,4-di-F | 4-CN | |
| 4-CF₃ | 2,4-di-Cl | 4-CN | |
| 4-CF₃ | 3-F | 4-F | |
| 4-CF₃ | 3-Cl | 4-F | |
| 4-CF₃ | 3-F, 4-Cl | 4-F | |
| 4-CF₃ | 3-Cl, 4-F | 4-F | |
| 4-CF₃ | 3,5-di-F | 4-F | |
| 4-CF₃ | 3,5-di-Cl | 4-F | |
| 4-CF₃ | 3-F, 5-Cl | 4-F | |
| 4-CF₃ | 3,4,5-trifluoro | 4-F | |
| 4-CF₃ | 3,4,5-trichloro | 4-F | |
| 4-CF₃ | 2-F | 4-F | |
| 4-CF₃ | 2-Cl | 4-F | |
| 4-CF₃ | 2-F, 4-Cl | 4-F | |
| 4-CF₃ | 2-Cl, 4-F | 4-F | |

TABLE 1-continued

| R₁ | R₂ | R₅ | m.p. (°C.) |
|---|---|---|---|
| 4-CF₃ | 2,4-di-F | 4-F | |
| 4-CF₃ | 2,4-di-Cl | 4-F | |
| 4-CF₃ | 3-F | 4-Cl | |
| 4-CF₃ | 3-F, 4-Cl | 4-CN | |
| 4-CF₃ | 3-Cl, 4-F | 4-Cl | |
| 4-CF₃ | 3,4-di-F | 4-Cl | |
| 4-CF₃ | 3,5-di-F | 4-Cl | |
| 4-CF₃ | 3,5-di-Cl | 4-Cl | |
| 4-CF₃ | 3-F, 5-Cl | 4-Cl | |
| 4-CF₃ | 3,4,5-trifluoro | 4-Cl | |
| 4-CF₃ | 3,4,5-trichloro | 4-Cl | |
| 4-CF₃ | 2-F | 4-Cl | |
| 4-CF₃ | 2-F, 4-Cl | 4-Cl | |
| 4-CF₃ | 2-Cl, 4-F | 4-Cl | |
| 4-CF₃ | 2,4-di-F | 4-Cl | |
| 4-CF₃ | 2,4-di-Cl | 4-Cl | |
| 4-Cl | 4-CF₃ | 4-Cl | 206 to 208 |
| 4-Cl | 4-Cl | 4-Br | 191 to 193.5 |
| 4-CF₃ | 4-Cl | 4-Br | 207 to 208 |
| 4-CN | 4-Cl | 4-Cl | 247 to 249 |
| 3-CF₃ | 4-Cl | 4-Cl | 131 to 139 |
| 4-Cl | 4-Cl | 3-Cl | 188 to 191 |
| 4-Cl | 4-Cl | 2-Cl | 192 to 195 |
| 4-CF₃ | 4-OMe | 4-Cl | 204 to 205 |
| 4-F | 4-Cl | 3,4-di-Cl | 185 to 186 |
| 4-CF₃ | 3-Cl | 4-Cl | 187 to 189 |
| 4-F | 3-Cl | 4-Cl | 177 to 179 |
| 4-CF₃ | 2-Cl | 4-Cl | 125 to 126 |
| 4-F | 2-Cl | 4-Cl | 107 to 111 |
| 4-CF₃ | 4-F | 4-SCH₃ | 170 to 172.5 |
| 4-CF₃ | 4-F | 4-OCF₂H | |
| 4-CF₃ | 4-Cl | 4-OCF₂H | |
| 4-CF₃ | 4-F | 4-OCF₃ | |
| 4-CF₃ | 4-Cl | 4-OCF₃ | |
| 3,4-OCF₂CF₂O | 4-F | 4-CN | |
| 4-CF₃ | 3,4-OCF₂CF₂O | 4-CN | |
| 4-CF₃ | 4-F | 3,4-OCF₂CF₂O | |
| 3,4-OCH₂O | 4-F | 4-CN | |
| 3,4-OCH₂CH₂O | 4-F | 4-CN | |
| 4-CF₃ | 3,4-OCH₂O | 4-CN | |
| 4-N₃ | 4-F | 4-CN | |
| 4-SCN | 4-F | 4-CN | |
| 4-NHSO₂Me | 4-F | 4-CN | |
| 4-CF₃ | 4-N₃ | 4-CN | |
| 4-CF₃ | 4-SCN | 4-CN | |
| 4-CF₃ | 4-NHSO₂Me | 4-CN | |
| 4-CF₃ | 4-F | 4-N₃ | |
| 4-CF₃ | 4-F | 4-SCN | |
| 4-CF₃ | 4-F | 4-NHSO₂Me | |
| 4-Cl | 4-Cl | 4-CH₂CN | 143 to 145 |
| 4-CF₃ | 4-iPr | 4-Cl | 194 to 195 |
| 4-Cl | 4-iPr | 4-Cl | 207 to 209 |
| 4-OMe | 4-iPr | 4-Cl | 162 to 163.5 |
| 4-Cl | 4-Me | 4-Cl | 201.5 to 203.5 |
| 4-OMe | 4-Me | 4-Cl | 183 to 184.5 |
| 4-iPr | 4-Me | 4-Cl | 172 to 174 |
| 4-NO₂ | 4-iPr | 4-Cl | 242 to 244 |
| 4-iPr | 4-iPr | 4-Cl | 122 to 126 |
| 2,5-di-F | 4-CN | 4-F | 149 to 150 |
| 3,5-di-NO₂ | 4-CN | 4-F | 132 to 134 |
| 4-Et | 4-CN | 4-F | 215 to 216 |
| 3-CF₃,4-F | 4-CN | 4-F | 175 to 176 |
| 4-OC₆H₅ | 4-CN | 4-F | 226 to 227 |
| 4-tBu | 4-CN | 4-H | 126 to 128.5 |
| 4-Cl | 4-CN | 4-H | 202 to 203 |
| 4-CN | 4-CN | 4-H | 218.5 to 220.5 |
| 2,3,4-tri-Cl | 4-CN | 4-F | 155 to 158 |
| 3-CF₃ | 4-CN | 4-F | 175 to 177 |
| 3-Cl | 4-CN | 4-F | 189 to 190 |
| 2-Cl | 4-CN | 4-F | 194 to 196 |
| 3-F | 4-CN | 4-F | 184 to 185 |
| 2-F | 4-CN | 4-F | 172 to 173 |
| 2,3,4-tri-Cl | 4-CF₃ | 4-OC₆H₅ | 196 to 198 |
| 3-CF₃,4-F | 4-CF₃ | 4-OC₆H₅ | 161 to 163 |
| 4-OC₆H₅ | 4-CF₃ | 4-OC₆H₅ | 185 to 186 |
| 4-CF₃ | 4-CF₃ | 4-OC₆H₅ | 141 to 143 |
| 3-CF₃ | 4-CF₃ | 4-OC₆H₅ | 169 to 171 |
| 4-CN | 4-CF₃ | 4-OC₆H₅ | 157 to 160 |
| 3-CN | 4-CF₃ | 4-OC₆H₅ | 178 to 180 |
| 4-Cl | 4-CF₃ | 4-OC₆H₅ | 150 to 152 |
| 3-Cl | 4-CF₃ | 4-OC₆H₅ | 179 to 180 |
| 4-F | 4-CF₃ | 4-OC₆H₅ | 140 to 142 |
| 4-Cl | 3-Cl | 4-Cl | 160 to 161 |
| 3-Cl | 3-Cl | 4-Cl | 173 to 175 |
| 4-iPr | 4-Cl | 4-Cl | 190 to 191 |
| 4-OCF₂CF₂H | 4-Cl | 4-Cl | 172 to 173 |
| 3-Cl,4-Cl | 4-Cl | 4-Cl | 227 to 229 |
| 2-F,4-Cl | 4-Cl | 4-Cl | 184 to 185 |
| 2,5-di-F | 4-CN | 4-Br | 178 to 180 |
| 3,5-di-NO₂ | 4-CN | 4-Br | 259 to 264 |
| 2,3,4-tri-Cl | 4-CN | 4-Br | 239 to 241 |
| 4-Et | 4-CN | 4-Br | 226 to 228 |
| 3-CF₃,4-F | 4-CN | 4-Br | 171 to 172 |
| 4-OC₆H₅ | 4-CN | 4-Br | 216 to 217 |
| 4-C₆H₅ | 4-CN | 4-Br | 227 to 228 |
| 3-CF₃ | 4-CN | 4-Br | 129 to 132 |
| 2-CF₃ | 4-CN | 4-Br | 175 to 180 |
| 4-CN | 4-CN | 4-Br | 150 to 151 |
| 3-CN | 4-CN | 4-Br | 210 to 212 |
| 2-CN | 4-CN | 4-Br | 237 to 239 |
| 3-Cl | 4-CN | 4-Br | 180 to 182 |
| 2-Cl | 4-CN | 4-Br | 224 to 226 |
| 4-F | 4-CN | 4-Br | 208 to 209 |
| 3-F | 4-CN | 4-Br | 202 to 203 |
| 2-F | 4-CN | 4-Br | 191 to 192 |
| 3-CF₃ | 4-CF₃ | 4-F | 123 to 129 |
| 4-CN | 4-CF₃ | 4-F | 253 to 254 |
| 3-CN | 4-CF₃ | 4-F | 161 to 171 |
| 4-F | 4-CF₃ | 4-F | 168 to 176 |
| 3-F | 4-CF₃ | 4-F | 148 to 153 |
| 3-Cl | 4-Cl | 4-OMe | 167 to 169 |
| 3-CF₃ | 4-Cl | 4-OMe | 179 to 180 |
| 3-CF₃,4-F | 4-Cl | 4-OMe | 135 to 136 |
| 4-F | 4-Cl | 4-OMe | 158 to 159 |
| 4-CN | 4-Cl | 4-OMe | 222 to 224 |
| 3-CN | 4-Cl | 4-OMe | 205 to 208 |
| 4-C₆H₆ | 4-Cl | 4-Cl | 200.5 to 203 |
| 4-O-s-Bu | 4-Cl | 4-Cl | 176.5 to 178 |
| 3,4-OCH₂O— | 4-Cl | 4-Cl | 221.5 to 223 |
| 3,5-di-F | 4-Cl | 4-Cl | 200.5 to 202 |
| 2,3,4-tri-Cl | 4-CF₃ | 3-CN | 234 to 246 |
| 3-CF₃,4-F | 4-CF₃ | 3-CN | 195 to 197 |
| 4-OC₆H₅ | 4-CF₃ | 3-CN | 209 to 211 |
| 3-CF₃ | 4-CF₃ | 3-CN | 179 to 180 |
| 4-CN | 4-CF₃ | 3-CN | 182 to 184 |
| 3-CN | 4-CF₃ | 3-CN | 182 to 184 |
| 3-Cl | 4-CF₃ | 3-CN | 215 to 216 |
| 4-F | 4-CF₃ | 3-CN | 175 to 177 |
| 4-CF₃ | 4-OCF₂CF₂H | 4-Cl | 198 to 199 |
| 4-Cl | 4-OCF₂CF₂H | 4-Cl | 186 to 187 |
| 4-OCF₂CF₂H | 4-OCF₂CF₂H | 4-Cl | 137 to 138 |
| 4-iPr | 4-OCF₂CF₂H | 4-Cl | 126 to 122.5 |
| 4-CF₃ | 4-OCF₂CF₂H | 4-H | 166 to 168.5 |
| 4-Br | 4-OCF₂CF₂H | 4-H | 183.5 to 185 |
| 4-CF₃ | 2-Me,4-Cl | 4-Cl | 151 to 152 |
| 3-CF₃ | 2-Me,4-Cl | 4-Cl | 98 to 101 |
| 4-CN | 2-Me,4-Cl | 4-Cl | 168 to 169 |
| 3-CN | 2-Me,4-Cl | 4-Cl | 177 to 178 |
| 4-Cl | 2-Me,4-Cl | 4-Cl | 152 to 153 |
| 3-Cl | 2-Me,4-Cl | 4-Cl | 111 to 113 |
| 4-F | 2-Me,4-Cl | 4-Cl | 142 to 148 |
| 3-CF₃,4-F | 2-Me,4-Cl | 4-Cl | 121 to 123 |
| 2-Me,4-Cl | 2-Me,4-Cl | 4-Cl | 105 to 109 |
| 3-Cl,4-F | 2-Me,4-Cl | 4-Cl | 125 to 128 |
| 4-CN | 4-CF₃ | 4-H | 219 to 221 |
| 2-CN | 4-CF₃ | 4-H | 187 to 188 |
| 3-Cl | 4-CF₃ | 4-H | 157 to 159 |
| 2-Cl | 4-CF₃ | 4-H | 210 to 212 |
| 4-F | 4-CF₃ | 4-H | 170 to 172 |
| 2-F | 4-CF₃ | 4-H | 178 to 179 |
| 3-CF₃ | 4-F | 4-H | 151 to 152 |
| 4-CN | 4-F | 4-H | 204 to 206 |
| 3-CN | 4-F | 4-H | 195 to 196 |
| 3-CL | 4-F | 4-H | 170 to 172 |
| 3-F | 4-F | 4-H | 143 to 144 |
| 3-CF₃,4-F | 4-F | 4-H | 178 to 180 |
| 3-Cl,4-F | 4-F | 4-H | 187 to 189 |
| 4-NHCOMe | 4-F | 4-Cl | 278 to 280 |
| 4-OEt | 4-F | 4-Cl | 199 to 200.5 |
| 4-C₆H₅ | 4-F | 4-Cl | 188 to 191 |
| 3-Cl, 4-Br | 4-F | 4-Cl | 211 to 212.5 |
| 2,4-di-F | 4-F | 4-Cl | 137 to 140 |

TABLE 1-continued

| R1 | R2 | R5 | m.p. (°C.) |
|---|---|---|---|
| 4-OMe | 4-CN | 4-OMe | 190 to 191 |
| 4-t-Bu | 4-CN | 4-OMe | 127 to 129 |
| 4-NO2 | 4-CN | 4-OMe | 230 to 232 |
| 4-CN | 4-CN | 4-OMe | 221 to 223 |
| 4-Cl | 4-CN | 4-OMe | 194 to 196 |
| 4-CF3 | 4-CN | 4-OMe | 189 to 191 |
| 4-CF3 | 4-CF3 | 4-C6H5 | 183 to 184 |
| 4-CN | 4-CF3 | 4-C6H5 | 229 to 231 |
| 4-Cl | 4-CF3 | 4-C6H5 | 224 to 226 |
| 4-F | 4-CF3 | 4-C6H5 | 206 to 208 |
| 4-t-Bu | 4-CF3 | 4-C6H5 | 206 to 208 |
| 3-F,4-CF3 | 4-CF3 | 4-C6H5 | 166 to 167 |
| 2-OMe | 4-Cl | 2-Cl | 158 to 160 |
| 3-OMe | 4-Cl | 2-Cl | 168 to 169 |
| 4-OMe | 4-Cl | 2-Cl | 153 to 155 |
| 2-Cl | 4-Cl | 2-Cl | 182 to 184 |
| 3-Cl | 4-Cl | 2-Cl | 197 to 198 |
| 4-CF3 | 4-CF3 | 4-CONEt2 | 195 to 196 |
| 4-CN | 4-CF3 | 4-CONEt2 | 238 to 241 |
| 4-Cl | 4-CF3 | 4-CONEt2 | 219 to 223 |
| 4-F | 4-CF3 | 4-CONEt2 | 163 to 165 |
| 4-CF3 | 4-CO2Me | 4-F | 172 to 176 |
| 4-CN | 4-CO2Me | 4-F | 193 to 195 |
| 4-Cl | 4-CO2Me | 4-F | 191 to 193 |
| 4-F | 4-CO2Me | 4-F | 188 to 189 |
| 4-CF3 | 4-CO2Me | 4-Cl | 237 to 238 |
| 4-CN | 4-CO2Me | 4-Cl | 261 to 263 |
| 4-Cl | 4-CO2Me | 4-Cl | 216 to 218 |
| 4-t-Bu | 4-CO2Me | 4-Cl | 183 to 185 |
| 2-CN | 4-Cl | 2-Cl | 186 to 187 |
| 3-CN | 4-Cl | 2-Cl | 200 to 202 |
| 4-CN | 4-Cl | 2-Cl | 232 to 234 |
| 4-Cl | 4-Cl | 2-Cl | 190 to 192 |
| 4-t-Bu | 4-Cl | 2-Cl | 195 to 197 |
| 4-CH2C6H5 | 4-Cl | 2-Cl | 154 to 157 |
| 4-F | 4-Cl | 2-Cl | 148 to 150 |
| 4-CF3 | 4-Cl | 2-Cl | 189 to 190 |
| 3-OMe | 2-Cl | 4-F | 128 to 130 |
| 4-OMe | 2-Cl | 4-F | 154 to 155 |
| 4-Cl | 2-Cl | 4-F | 165 to 166 |
| 3-SO2NH2 | 2-Cl | 4-F | 98 to 101 |
| 4-SO2NH2 | 2-Cl | 4-F | 195 to 197 |
| 3-CN | 2-Cl | 4-F | 153 to 154 |
| 4-CN | 2-Cl | 4-F | 160 to 163 |
| 4-t-Bu | 2-Cl | 4-F | 92 to 94 |
| 2-OMe | 3-Cl | 4-F | 153 to 155 |
| 3-OMe | 3-Cl | 4-F | 146 to 147 |
| 4-OMe | 3-Cl | 4-F | 200 to 201 |
| 2-Cl | 3-Cl | 4-F | 137 to 139 |
| 3-Cl | 3-Cl | 4-F | 151 to 152 |
| 4-Cl | 3-Cl | 4-F | 192 to 194 |
| 4-SO2NH2 | 3-Cl | 4-F | 273 to 278 |
| 2-CN | 3-Cl | 4-F | 153 to 155 |
| 3-CN | 3-Cl | 4-F | 195 to 196 |
| 4-CN | 3-Cl | 4-F | 219 to 220 |
| 4-t-Bu | 3-Cl | 4-F | 176 to 177 |
| 4-CH2C6H5 | 3-Cl | 4-F | 159 to 163 |
| 4-CF3 | 4-t-Bu | 4-C6H5 | 202 to 204 |
| 4-Cl | 4-t-Bu | 4-C6H5 | solid (b) |
| 4-Cl | 4-t-Bu | 4-t-Bu | 164 to 166 |
| 4-CF3 | 4-t-Bu | 4-t-Bu | 161 to 164 |
| 4-NO2 | 4-t-Bu | 4-t-Bu | 202 to 205 |
| 4-CN | 4-t-Bu | 4-t-Bu | 234 to 237 |
| 4-OMe | 4-t-Bu | 4-t-Bu | 194 to 196 |
| 4-OMe | 4-CN | 4-CN | 209 to 211 |
| 3,4,5-tri-Cl | 4-Cl | 4-F | 190 to 192 |
| 4-SCH3 | 4-Cl | 4-F | 183 to 185 |
| 4-CO2Et | 4-Cl | 4-F | 183 to 184 |
| 4-CF3 | 3,4-di-Cl | 4-F | 241 to 243 |
| 4-OCF3 | 3,4-di-Cl | 4-F | 219 to 221 |
| 4-C6H5 | 3,4-di-Cl | 4-F | 193 to 194 |
| 4-SO2NH2 | 3,4-di-Cl | 4-F | 261 to 264 |
| 4-OEt | 3,4-di-Cl | 4-F | 226 to 227 |
| 4-CF3 | 4-CF3 | 4-COCF3 | 164 to 166 |
| 4-CN | 4-CF3 | 4-COCF3 | 110 to 113 |
| 4-Cl | 4-CF3 | 4-COCF3 | 122 to 125 |
| 4-F | 4-CF3 | 4-COCF3 | 74 to 76 |
| 4-t-Bu | 4-CF3 | 4-COCF3 | 95 to 98 |
| 4-CO2Me | 4-CF3 | 4-COCF3 | 104 to 108 |
| 4-SO2NH2 | 4-Cl | 2-Cl | 276 to 283 |
| 4-F | 3-Cl | 4-F | 167 to 168 |
| 4-CF3 | 3-Cl | 4-F | 181 to 183 |
| 3-SO2NH2 | 4-Cl | 2-Cl | 186 to 189 |
| 3-OMe | 2-Cl | 4-F | 101 to 105 |
| 4-OMe | 2-Cl | 4-F | 101 to 105 |
| 2-SO2NH2 | 4-Cl | 2-Cl | 242 to 246 |
| 3-OMe | 2-CN | 4-F | 167 to 168 |
| 4-OMe | 2-CN | 4-F | 202 to 205 |
| 2-Cl | 2-CN | 4-F | 141 to 142 |
| 3-Cl | 2-CN | 4-F | 173 to 174 |
| 4-Cl | 2-CN | 4-F | 181 to 182 |
| 3-SO2NH2 | 2-CN | 4-F | 149 to 153 |
| 4-SO2NH2 | 2-CN | 4-F | 170 to 174 |
| 2-CN | 2-CN | 4-F | 159 to 161 |
| 3-CN | 2-CN | 4-F | 184 to 186 |
| 4-CN | 2-CN | 4-F | 258 to 259 |
| 4-t-Bu | 2-CN | 4-F | 206 to 207 |
| 4-CF3 | 2-CN | 4-F | 206 to 207 |
| 2-OMe | 4-Cl | 3-Cl | 131 to 133 |
| 3-OMe | 4-Cl | 3-Cl | 149 to 150 |
| 4-OMe | 4-Cl | 3-Cl | 201 to 202 |
| 2-Cl | 4-Cl | 3-Cl | 171 to 173 |
| 3-Cl | 4-Cl | 3-Cl | 143 to 146 |
| 2-SO2NH2 | 4-Cl | 3-Cl | 205 to 207 |
| 4-SO2NH2 | 4-Cl | 3-Cl | 275 to 280 |
| 2-CN | 4-Cl | 3-Cl | 146 to 149 |
| 3-CN | 4-Cl | 3-Cl | 155 to 157 |
| 4-t-Bu | 4-Cl | 3-Cl | 106 to 107 |
| 4-CH2C6H5 | 4-Cl | 3-Cl | 119 to 125 |
| 4-CN | 4-Cl | 3-Cl | 179 to 185 |
| 4-CO2-n-Pr | 4-Cl | 3-Cl | 166 to 168 |
| 3,5-di-Cl | 4-Cl | 3-Cl | 184 to 187 |
| 4-CO2-n-Pr | 4-Cl | 4-F | 183.5 to 184.5 |
| 4-CF3 | 4-CF3 | 4-CO2H | 261 to 265 |
| 4-CN | 4-CF3 | 4-CO2H | 137 to 141 |
| 4-Cl | 4-CF3 | 4-CO2H | 228 to 230 |
| 4-F | 4-CF3 | 4-CO2H | 154 to 160 |
| 4-t-Bu | 4-CF3 | 4-CO2H | 146 to 153 |
| 4-CF3 | 4-CF3 | 4-C2H5 | 131 to 133 |
| 4-CF3 | 4-NH2 | 4-F | 195 to 197 |
| 3-SO2NH2 | 4-Cl | 3-Cl | 130 to 138 |
| 4-CN | 2-OMe | 4-F | 173 to 176 |
| 2-CH2C6H5 | 2-OMe | 4-F | 117 to 121 |
| 4-CF3 | 2-OMe | 4-F | 154 to 159 |
| 2-OMe | 2-OMe | 4-F | 107 to 111 |
| 4-OMe | 2-OMe | 4-F | 109 to 111 |
| 2-Cl | 2-OMe | 4-F | 90 to 97 |
| 4-Cl | 2-OMe | 4-F | 155 to 157 |
| 4-SO2NH2 | 2-OMe | 4-F | 141 to 144 |
| 2-CN | 2-OMe | 4-F | 179 to 181 |
| 3-OMe | 2-OMe | 4-F | oil (c) |
| 3-Cl | 2-OMe | 4-F | oil (d) |
| 3-OMe | 4-Cl | 2-OMe | 112 to 114 |
| 4-t-Bu | 2-OMe | 4-F | 76 to 83 |
| 3-CN | 2-OMe | 4-F | 80 to 81 |
| 4-OMe | 4-Cl | 2-OMe | 149 to 153 |
| 2-Cl | 4-Cl | 2-OMe | 130 to 132 |
| 3-Cl | 4-Cl | 2-OMe | 139 to 141 |
| 4-Cl | 4-Cl | 2-OMe | 155 to 157 |
| 2-SO2NH2 | 4-Cl | 2-OMe | 123 to 127 |
| 4-SO2NH2 | 4-Cl | 2-OMe | 248 to 256 |
| 2-OMe | 4-Cl | 2-OMe | 124 to 126 |
| 2-CN | 4-Cl | 2-OMe | 163 to 165 |
| 3-CN | 4-Cl | 2-OMe | 154 to 160 |
| 4-CN | 4-Cl | 2-OMe | 153 to 159 |
| 2-CH2C6H5 | 4-Cl | 2-OMe | 148 to 150 |
| 4-CF3 | 4-Cl | 2-OMe | 172 to 173 |
| 3-SO2NH2 | 4-Cl | 2-OMe | 118 to 123 |
| 4-t-Bu | 4-Cl | 2-OMe | 87 to 92 |
| 2-SO2NH2 | 3-Cl | 4-F | 114 to 121 |
| 3-SO2NH2 | 3-Cl | 4-F | 118 to 123 |
| 2-SO2NH2 | 2-OMe | 4-F | oil (e) |
| 3-SO2NH2 | 2-OMe | 4-F | oil (f) |
| 4-OMe | 2-CH2C6H5 | 4-F | 153 to 154 |
| 4-Br | 4-F | 3,4-di-F | 175.5 to 177.5 |
| 4-CN | 4-CN | 4-CN | 173 to 176 |
| 4-t-Bu | 4-CN | 4-CN | 143 to 142 |
| 4-OMe | 4-Cl | 4-OMe | 174 to 175 |
| 4-NO2 | 4-Cl | 4-OMe | 238 to 239 |
| 4-Br | 4-OCF3 | 4-F | 187.5 to 189 |
| 4-OCF2CF2H | 4-Cl | 3,4-di-F | 145 to 146 |
| 3,4,5-tri-Cl | 4-Cl | 4-Cl | >250° |

TABLE 1-continued

| R₁ | R₂ | R₅ | m.p. (°C.) |
|---|---|---|---|
| 4-CN | 2-CH₂C₆H₅ | 4-F | 156 to 161 |
| 4-t-Bu | 2-CH₂C₆H₅ | 4-F | 182 to 184 |
| 4-CF₃ | 2-CH₂C₆H₅ | 4-F | 85 to 87 |
| 4-CF₃ | 3,4-di-F | 4-F | 193.5 to 195 |
| 4-OCF₃ | 3,4-di-F | 4-F | 205 to 206 |
| 4-SMe | 3,4-di-F | 4-F | 208.5 to 210 |
| 4-Br | 3,4-di-F | 4-F | 195 to 196 |
| 4-SO₂NH₂ | 3,4-di-F | 4-F | >250° |
| 4-C₆H₅ | 3,4-di-F | 4-F | >140° |
| 4-Cl | 3,4-di-F | 4-F | 172 to 174 |
| 4-OEt | 3,4-di-F | 4-F | 220.5 to 221.5 |
| 4-F | 4-Cl | 4-NO₂ | 167 to 176 |
| 4-Cl | 4-Cl | 4-t-Bu | 195 to 197 |
| 4-OMe | 4-Cl | 4-t-Bu | 173 to 175 |
| 4-CN | 4-Cl | 4-t-Bu | 151 to 155 |
| 4-CF₃ | 4-Cl | 4-t-Bu | 150 to 153 |
| 4-t-Bu | 4-Cl | 4-t-Bu | 201 to 202 |
| 4-NO₂ | 4-Cl | 4-t-Bu | 246 to 252 |
| 4-Cl | 4-Cl | 4-C₆H₅ | 211 to 213 |
| 4-OMe | 4-Cl | 4-C₆H₅ | 206 to 208 |
| 4-CN | 4-Cl | 4-C₆H₅ | 220 to 222 |
| 4-CF₃ | 4-Cl | 4-C₆H₅ | 195 to 197 |
| 4-t-Bu | 4-Cl | 4-C₆H₅ | 211 to 213 |
| 4-NO₂ | 4-Cl | 4-C₆H₅ | 220 to 225 |
| 4-CN | 4-CF₃ | 4-Br | 255 to 257 |
| 4-Cl | 4-CF₃ | 4-Br | 206 to 207 |
| 4-F | 4-CF₃ | 4-Br | 209 to 210 |
| 4-NO₂ | 4-CF | 4-Br | 239 to 242 |
| 4-CN | 4-F | 4-CO₂Me | 164 to 168 |
| 4-F | 4-F | 4-CO₂Me | 164 to 167 |
| 4-t-Bu | 4-F | 4-CO₂Me | 198 to 202 |
| 3-CF₃,4-F | 4-F | 4-CO₂Me | 113 to 118 |
| 4-CN | 4-CF₃ | 4-CO₂Me | 191 to 192 |
| 4-F | 4-CF₃ | 4-CO₂Me | 156 to 157 |
| 4-CO₂Me | 4-CF₃ | 4-CO₂Me | 170 to 172 |
| 4-CF₃ | 4-NO₂ | 4-Cl | 240 to 242 |
| 4-CF₃ | 4-CF₃ | 4-CONH(p-C₆H₄-CF₃) | >275 |
| 4-Cl | 4-CF₃ | 4-CONH(p-C₆H₄-Cl) | 276 to 279 |
| 4-F | 4-Cl | 4-CO₂Me | 195 to 197 |
| 4-CF₃ | 4-NH₂ | 4-Cl | 155 to 160 |
| 4-C₆H₄S(p-C₆H₄Cl) | 3-CN | 4-F | 205 to 209 |
| 2-CN,2-CF₃ | 3-CN | 4-F | 210 to 215 |
| 2-OCH₃ | 3-OCH₃ | 4-F | 75 to 78 |
| 3-OCH₃ | 3-OCH₃ | 4-F | 87 to 90 |
| 4-OCH₃ | 3-OCH₃ | 4-F | 174 to 176 |
| 2-Cl | 3-OCH₃ | 4-F | 143 to 145 |
| 3-Cl | 3-OCH₃ | 4-F | 141 to 143 |
| 4-Cl | 3-OCH₃ | 4-F | 163 to 165 |
| 2-SO₂NH₂ | 3-OCH₃ | 4-F | 100 to 105 |
| 3-SO₂NH₂ | 3-OCH₃ | 4-F | 105 to 110 |
| 4-SO₂NH₂ | 3-OCH₃ | 4-F | 225 to 257 |
| 2-CN | 3-OCH₃ | 4-F | |
| 4-t-Bu | 3-OCH₃ | 4-F | 136 to 138 |
| 2-CH₂C₆H₅ | 3-OCH₃ | 4-F | 149 to 150 |
| 4-CF₃ | 3-OCH₃ | 4-F | 166 to 170 |
| 4-OCH₃ | 4-Cl | 3-CN | 107 to 109 |
| 3-Cl | 4-Cl | 3-CN | 96 to 99 |
| 4-SO₂NH₂ | 4-Cl | 3-CN | 102 to 105 |
| 2-SO₂NH₂ | 4-Cl | 3-CN | 134 to 138 |
| 4-SO₂NH₂ | 4-Cl | 3-CN | 135 to 142 |
| 4-SO₂NH₂ | 4-Cl | 3-CN | 229 to 231 |
| 4-CN | 4-Cl | 3-CN | 195 to 198 |
| 4-t-Bu | 4-Cl | 3-CN | 122 to 126 |
| 4-CF₃ | 4-Cl | 3-CN | 188 to 190 |
| 4-CN | 3-OCH₃ | 4-F | 127 to 135 |
| 2-OCH₃ | 4-Cl | 2-CN | 196 to 198 |
| 2-Cl | 4-Cl | 2-CN | 201 to 202 |
| 3-Cl | 4-Cl | 2-CN | 198 to 200 |
| 4-Cl | 4-Cl | 2-CN | 150 to 153 |
| 2-SO₂NH₂ | 4-Cl | 2-CN | 181 to 185 |
| 3-SO₂NH₂ | 4-Cl | 2-CN | 125 to 130 |
| 4-SO₂NH₂ | 4-Cl | 2-CN | 258 to 260 |
| 2-CN | 4-Cl | 2-CN | 190 to 192 |
| 3-CN | 4-Cl | 2-CN | 186 to 189 |
| 4-CN | 4-Cl | 2-CN | 237 to 241 |
| 4-t-Bu | 4-Cl | 2-CN | 203 to 205 |
| 2-CH₂C₆H₅ | 4-Cl | 2-CN | 186 to 188 |
| 4-CF₃ | 4-Cl | 2-CN | 194 to 196 |
| 4-F | 4-Cl | 2-CN | 200 to 202 |
| 4-Br | 4-OCHF₂ | 4-F | 181 to 182.5 |

H¹NMR spectra (δ):
(a) 8.55 (NH)
(b) 8.5 (NH)
(c) 8.50 (NH)
(d) 8.55 (NH)
(e) 10.35 (NH)
(f) 8.75 (NH)

TABLE 2

| R₁ | R₂ | W | A | Y | m.p. (°C.) |
|---|---|---|---|---|---|
| 4-CF₃ | 4-F | 4-CN | CH₃ | H | |
| 4-CF₃ | 4-F | 4-CN | CH₂CH₃ | H | |
| 4-CF₃ | 4-F | 4-CN | CO₂CH₃ | H | |
| 4-CF₃ | 4-F | 4-CN | CO₂CH₂CH₃ | H | |
| 4-CF₃ | 4-F | 4-CN | COCH₃ | H | |
| 4-CF₃ | 4-F | 4-CN | COCF₃ | H | |
| 4-CF₃ | 4-F | 4-Cl | CH₃ | H | |
| 4-CF₃ | 4-F | 4-CF₃ | CH₃ | H | |
| 4-CF₃ | 4-F | 4-F | CH₃ | H | |
| 4-CF₃ | 4-F | 3,4-di-F | CH₃ | H | |
| 4-CF₃ | 4-F | 3-Cl | CH₃ | H | |
| 4-CF₃ | 4-F | 4-CO₂Me | CH₃ | H | |
| 4-CF₃ | 4-F | 3-CN | CH₃ | H | |
| 4-CF₃ | 4-Cl | 4-Cl | CH₃ | H | 205 to 206 |
| 4-CF₃ | 4-Cl | 4-F | CH₃ | H | 195 to 197 |
| 4-CF₃ | 4-Cl | 4-CF₃ | CH₃ | H | |
| 4-CF₃ | 4-Cl | 3,4-di-F | CH₃ | H | |
| 4-CF₃ | 4-Cl | 3-Cl | CH₃ | H | |
| 4-CF₃ | 4-Cl | 4-CO₂Me | CH₃ | H | |
| 4-CF₃ | 4-Cl | 3-CN | CH₃ | H | |
| 4-CF₃ | 4-CF₃ | 4-Cl | CH₃ | H | 136 to 139 |
| 4-CF₃ | 4-CF₃ | 4-F | CH₃ | H | 149 to 150 |
| 4-CF₃ | 4-CF₃ | 4-CF₃ | CH₃ | H | |
| 4-CF₃ | 4-CF₃ | 3,4-di-F | CH₃ | H | |
| 4-CF₃ | 4-CF₃ | 3-Cl | CH₃ | H | |
| 4-CF₃ | 4-CF₃ | 4-CO₂Me | CH₃ | H | |
| 4-CF₃ | 4-CF₃ | 3-CN | CH₃ | H | |
| 4-CF₃ | 4-OCF₃ | 4-Cl | CH₃ | H | 136 to 139 |
| 4-CF₃ | 4-OCF₃ | 4-F | CH₃ | H | 149 to 150 |
| 4-CF₃ | 4-OCF₃ | 4-CF₃ | CH₃ | H | |
| 4-CF₃ | 4-OCF₃ | 4-CO₂Me | CH₃ | H | |

TABLE 2-continued

| R₁ | R₂ | W | A | Y | m.p. (°C.) |
|---|---|---|---|---|---|
| 4-CF₃ | 4-OCF₃ | 3-Cl | CH₃ | H | |
| 4-CF₃ | 4-OCF₃ | 3,4-di-F | CH₃ | H | |
| 4-CF₃ | 4-OCF₃ | 4-CN | CH₃ | H | |
| 4-CF₃ | 4-OCF₃ | 3-CN | CH₃ | H | |
| 4-CF₃ | 4-OCF₂H | 4-Cl | CH₃ | H | |
| 4-CF₃ | 4-OCF₂H | 4-F | CH₃ | H | |
| 4-CF₃ | 4-OCF₂H | 4-CF₃ | CH₃ | H | |
| 4-CF₃ | 4-OCF₂H | 4-CO₂Me | CH₃ | H | |
| 4-CF₃ | 4-OCF₂H | 3-Cl | CH₃ | H | |
| 4-CF₃ | 4-OCF₂H | 3,4-di-F | CH₃ | H | |
| 4-CF₃ | 4-OCF₂H | 4-CN | CH₃ | H | |
| 4-CF₃ | 4-OCF₂H | 3-CN | CH₃ | H | |
| 4-CF₃ | 4-CN | 4-Cl | CH₃ | H | |
| 4-CF₃ | 4-CN | 4-F | CH₃ | H | |
| 4-CF₃ | 4-CN | 4-CF₃ | CH₃ | H | |
| 4-CF₃ | 4-CN | 4-CO₂Me | CH₃ | H | |
| 4-CF₃ | 4-CN | 3-Cl | CH₃ | H | |
| 4-CF₃ | 4-CN | 3,4-di-F | CH₃ | H | |
| 4-CF₃ | 4-CN | 4-CN | CH₃ | H | |
| 4-CF₃ | 4-CN | 3-CN | CH₃ | H | |
| 4-CF₃ | 4-H | 4-Cl | CH₃ | H | |
| 4-CF₃ | 4-H | 4-F | CH₃ | H | |
| 4-CF₃ | 4-H | 4-CF₃ | CH₃ | H | |
| 4-CF₃ | 4-H | 4-CO₂Me | CH₃ | H | |
| 4-CF₃ | 4-H | 3-Cl | CH₃ | H | |
| 4-CF₃ | 4-H | 3,4-di-F | CH₃ | H | |
| 4-CF₃ | 4-H | 4-CN | CH₃ | H | |
| 4-CF₃ | 4-H | 3-CN | CH₃ | H | |
| 4-CF₃ | 4-Br | 4-Cl | CH₃ | H | |
| 4-CF₃ | 4-Br | 4-F | CH₃ | H | |
| 4-CF₃ | 4-Br | 4-CF₃ | CH₃ | H | |
| 4-CF₃ | 4-Br | 4-CO₂Me | CH₃ | H | |
| 4-CF₃ | 4-Br | 3-Cl | CH₃ | H | |
| 4-CF₃ | 4-Br | 3,4-di-F | CH₃ | H | |
| 4-CF₃ | 4-Br | 4-CN | CH₃ | H | |
| 4-OCF₃ | 4-F | 4-Cl | CH₃ | H | |
| 4-OCF₃ | 4-F | 4-OCF₃ | CH₃ | H | |
| 4-OCF₃ | 4-F | 4-F | CH₃ | H | |
| 4-OCF₃ | 4-F | 3,4-di-F | CH₃ | H | |
| 4-OCF₃ | 4-F | 3-Cl | CH₃ | H | |
| 4-OCF₃ | 4-F | 4-CO₂Me | CH₃ | H | |
| 4-OCF₃ | 4-F | 3-CN | CH₃ | H | |
| 4-OCF₃ | 4-Cl | 4-Cl | CH₃ | H | |
| 4-OCF₃ | 4-Cl | 4-F | CH₃ | H | |
| 4-OCF₃ | 4-Cl | 4-CF₃ | CH₃ | H | |
| 4-OCF₃ | 4-Cl | 3,4-di-F | CH₃ | H | |
| 4-OCF₃ | 4-Cl | 3-Cl | CH₃ | H | |
| 4-OCF₃ | 4-Cl | 4-CO₂Me | CH₃ | H | |
| 4-OCF₃ | 4-Cl | 3-CN | CH₃ | H | |
| 4-OCF₃ | 4-CF₃ | 4-Cl | CH₃ | H | |
| 4-OCF₃ | 4-CF₃ | 4-F | CH₃ | H | |
| 4-OCF₃ | 4-CF₃ | 4-CF₃ | CH₃ | H | |
| 4-OCF₃ | 4-CF₃ | 3,4-di-F | CH₃ | H | |
| 4-OCF₃ | 4-CF₃ | 3-Cl | CH₃ | H | |
| 4-OCF₃ | 4-CF₃ | 4-CO₂Me | CH₃ | H | |
| 4-OCF₃ | 4-CF₃ | 3-CN | CH₃ | H | |
| 4-OCF₃ | 4-OCF₃ | 4-Cl | CH₃ | H | |
| 4-OCF₃ | 4-OCF₃ | 4-F | CH₃ | H | |
| 4-OCF₃ | 4-OCF₃ | 4-CF₃ | CH₃ | H | |
| 4-OCF₃ | 4-OCF₃ | 4-CO₂Me | CH₃ | H | |
| 4-OCF₃ | 4-OCF₃ | 3-Cl | CH₃ | H | |
| 4-OCF₃ | 4-OCF₃ | 3,4-di-F | CH₃ | H | |
| 4-OCF₃ | 4-OCF₃ | 4-CN | CH₃ | H | |
| 4-OCF₃ | 4-OCF₃ | 3-CN | CH₃ | H | |
| 4-OCF₃ | 4-OCF₂H | 4-Cl | CH₃ | H | |
| 4-OCF₃ | 4-OCF₂H | 4-F | CH₃ | H | |
| 4-OCF₃ | 4-OCF₂H | 4-CF₃ | CH₃ | H | |
| 4-OCF₃ | 4-OCF₂H | 4-CO₂Me | CH₃ | H | |
| 4-OCF₃ | 4-OCF₂H | 3-Cl | CH₃ | H | |
| 4-OCF₃ | 4-OCF₂H | 3,4-di-F | CH₃ | H | |
| 4-OCF₃ | 4-OCF₂H | 4-CN | CH₃ | H | |
| 4-OCF₃ | 4-OCF₂H | 3-CN | CH₃ | H | |
| 4-OCF₃ | 4-CN | 4-Cl | CH₃ | H | |
| 4-OCF₃ | 4-CN | 4-F | CH₃ | H | |
| 4-OCF₃ | 4-CN | 4-CF₃ | CH₃ | H | |
| 4-OCF₃ | 4-CN | 4-CO₂Me | CH₃ | H | |
| 4-OCF₃ | 4-CN | 3-Cl | CH₃ | H | |
| 4-OCF₃ | 4-CN | 3,4-di-F | CH₃ | H | |
| 4-OCF₃ | 4-CN | 4-CN | CH₃ | H | |
| 4-OCF₃ | 4-CN | 3-CN | CH₃ | H | |
| 4-OCF₃ | 4-H | 4-Cl | CH₃ | H | |

TABLE 2-continued

| R₁ | R₂ | W | A | Y | m.p. (°C.) |
|---|---|---|---|---|---|
| 4-OCF₃ | 4-H | 4-F | CH₃ | H | |
| 4-OCF₃ | 4-H | 4-CF₃ | CH₃ | H | |
| 4-OCF₃ | 4-H | 4-CO₂Me | CH₃ | H | |
| 4-OCF₃ | 4-H | 3-Cl | CH₃ | H | |
| 4-OCF₃ | 4-H | 3,4-di-F | CH₃ | H | |
| 4-OCF₃ | 4-H | 4-CN | CH₃ | H | |
| 4-OCF₃ | 4-H | 3-CN | CH₃ | H | |
| 4-OCF₃ | 4-Br | 4-Cl | CH₃ | H | |
| 4-OCF₃ | 4-Br | 4-F | CH₃ | H | |
| 4-OCF₃ | 4-Br | 4-CF₃ | CH₃ | H | |
| 4-OCF₃ | 4-Br | 4-CO₂Me | CH₃ | H | |
| 4-OCF₃ | 4-Br | 3-Cl | CH₃ | H | |
| 4-OCF₃ | 4-Br | 3,4-di-F | CH₃ | H | |
| 4-OCF₃ | 4-Br | 4-CN | CH₃ | H | |
| 4-Cl | 4-F | 4-Cl | CH₃ | H | 195 to 197.5 |
| 4-Cl | 4-F | 4-CF₃ | CH₃ | H | |
| 4-Cl | 4-F | 4-F | CH₃ | H | |
| 4-Cl | 4-F | 3,4-di-F | CH₃ | H | |
| 4-Cl | 4-F | 3-Cl | CH₃ | H | |
| 4-Cl | 4-F | 4-CO₂Me | CH₃ | H | |
| 4-Cl | 4-F | 3-CN | CH₃ | H | |
| 4-Cl | 4-Cl | 4-Cl | CH₃ | H | 189 to 190 |
| 4-Cl | 4-Cl | 4-F | CH₃ | H | |
| 4-Cl | 4-Cl | 4-CF₃ | CH₃ | H | |
| 4-Cl | 4-Cl | 3,4-di-F | CH₃ | H | |
| 4-Cl | 4-Cl | 3-Cl | CH₃ | H | |
| 4-Cl | 4-Cl | 4-CO₂Me | CH₃ | H | |
| 4-Cl | 4-Cl | 3-CN | CH₃ | H | |
| 4-Cl | 4-CF₃ | 4-Cl | CH₃ | H | 132 to 134 |
| 4-Cl | 4-CF₃ | 4-F | CH₃ | H | 108 to 111 |
| 4-Cl | 4-CF₃ | 4-CF₃ | CH₃ | H | |
| 4-Cl | 4-CF₃ | 3,4-di-F | CH₃ | H | |
| 4-Cl | 4-CF₃ | 3-Cl | CH₃ | H | |
| 4-Cl | 4-CF₃ | 4-CO₂Me | CH₃ | H | |
| 4-Cl | 4-CF₃ | 3-CN | CH₃ | H | |
| 4-Cl | 4-OCF₃ | 4-Cl | CH₃ | H | |
| 4-Cl | 4-OCF₃ | 4-F | CH₃ | H | |
| 4-Cl | 4-OCF₃ | 4-CF₃ | CH₃ | H | |
| 4-Cl | 4-OCF₃ | 3,4-di-F | CH₃ | H | |
| 4-Cl | 4-OCF₃ | 3-Cl | CH₃ | H | |
| 4-Cl | 4-OCF₃ | 4-CO₂Me | CH₃ | H | |
| 4-Cl | 4-OCF₃ | 3-CN | CH₃ | H | |
| 4-Cl | 4-OCF₂H | 4-Cl | CH₃ | H | |
| 4-Cl | 4-OCF₂H | 4-F | CH₃ | H | |
| 4-Cl | 4-OCF₂H | 4-CF₃ | CH₃ | H | |
| 4-Cl | 4-OCF₂H | 4-CO₂Me | CH₃ | H | |
| 4-Cl | 4-OCF₂H | 3-Cl | CH₃ | H | |
| 4-Cl | 4-OCF₂H | 3,4-di-F | CH₃ | H | |
| 4-Cl | 4-OCF₂H | 4-CN | CH₃ | H | |
| 4-Cl | 4-OCF₂H | 3-CN | CH₃ | H | |
| 4-Cl | 4-CN | 4-Cl | CH₃ | H | |
| 4-Cl | 4-CN | 4-F | CH₃ | H | |
| 4-Cl | 4-CN | 4-CF₃ | CH₃ | H | |
| 4-Cl | 4-CN | 4-CO₂Me | CH₃ | H | |
| 4-Cl | 4-CN | 3-Cl | CH₃ | H | |
| 4-Cl | 4-CN | 3,4-di-F | CH₃ | H | |
| 4-Cl | 4-CN | 4-CN | CH₃ | H | |
| 4-Cl | 4-CN | 3-CN | CH₃ | H | |
| 4-Cl | 4-H | 4-Cl | CH₃ | H | |
| 4-Cl | 4-H | 4-F | CH₃ | H | |
| 4-Cl | 4-H | 4-CF₃ | CH₃ | H | |
| 4-Cl | 4-H | 4-CO₂Me | CH₃ | H | |
| 4-Cl | 4-H | 3-Cl | CH₃ | H | |
| 4-Cl | 4-H | 3,4-di-F | CH₃ | H | |
| 4-Cl | 4-H | 4-CN | CH₃ | H | |
| 4-Cl | 4-H | 3-CN | CH₃ | H | |
| 4-Cl | 4-Br | 4-Cl | CH₃ | H | |
| 4-Cl | 4-Br | 4-F | CH₃ | H | |
| 4-Cl | 4-Br | 4-CF₃ | CH₃ | H | |
| 4-Cl | 4-Br | 4-CO₂Me | CH₃ | H | |
| 4-Cl | 4-Br | 3-Cl | CH₃ | H | |
| 4-Cl | 4-Br | 3,4-di-F | CH₃ | H | |
| 4-Cl | 4-Br | 4-CN | CH₃ | H | |
| 4-Cl | 4-Br | 3-CN | CH₃ | H | |
| 4-Br | 4-F | 4-Cl | CH₃ | H | |
| 4-Br | 4-F | 4-CF₃ | CH₃ | H | |
| 4-Br | 4-F | 4-F | CH₃ | H | |
| 4-Br | 4-F | 3,4-di-F | CH₃ | H | |
| 4-Br | 4-F | 3-Cl | CH₃ | H | |
| 4-Br | 4-F | 4-CO₂Me | CH₃ | H | |
| 4-Br | 4-F | 3-CN | CH₃ | H | |

TABLE 2-continued

| R₁ | R₂ | W | A | Y | m.p. (°C.) |
|---|---|---|---|---|---|
| 4-Br | 4-Cl | 4-Cl | CH₃ | H | |
| 4-Br | 4-Cl | 4-F | CH₃ | H | |
| 4-Br | 4-Cl | 4-CF₃ | CH₃ | H | |
| 4-Br | 4-Cl | 3,4-di-F | CH₃ | H | |
| 4-Br | 4-Cl | 3-Cl | CH₃ | H | |
| 4-Br | 4-Cl | 4-CO₂Me | CH₃ | H | |
| 4-Br | 4-Cl | 3-CN | CH₃ | H | |
| 4-Br | 4-CF₃ | 4-Cl | CH₃ | H | |
| 4-Br | 4-CF₃ | 4-F | CH₃ | H | |
| 4-Br | 4-CF₃ | 4-CF₃ | CH₃ | H | |
| 4-Br | 4-CF₃ | 3,4-di-F | CH₃ | H | |
| 4-Br | 4-CF₃ | 3-Cl | CH₃ | H | |
| 4-Br | 4-CF₃ | 4-CO₂Me | CH₃ | H | |
| 4-Br | 4-CF₃ | 3-CN | CH₃ | H | |
| 4-Br | 4-OCF₃ | 4-Cl | CH₃ | H | |
| 4-Br | 4-OCF₃ | 4-F | CH₃ | H | |
| 4-Br | 4-OCF₃ | 4-CF₃ | CH₃ | H | |
| 4-Br | 4-OCF₃ | 4-CO₂Me | CH₃ | H | |
| 4-Br | 4-OCF₃ | 3-Cl | CH₃ | H | |
| 4-Br | 4-OCF₃ | 3,4-di-F | CH₃ | H | |
| 4-Br | 4-OCF₃ | 4-CN | CH₃ | H | |
| 4-Br | 4-OCF₃ | 3-CN | CH₃ | H | |
| 4-Br | 4-OCF₂H | 4-Cl | CH₃ | H | |
| 4-Br | 4-OCF₂H | 4-F | CH₃ | H | |
| 4-Br | 4-OCF₂H | 4-CF₃ | CH₃ | H | |
| 4-Br | 4-OCF₂H | 4-CO₂Me | CH₃ | H | |
| 4-Br | 4-OCF₂H | 3-Cl | CH₃ | H | |
| 4-Br | 4-OCF₂H | 3,4-di-F | CH₃ | H | |
| 4-Br | 4-OCF₂H | 4-CN | CH₃ | H | |
| 4-Br | 4-OCF₂H | 3-CN | CH₃ | H | |
| 4-Br | 4-CN | 4-Cl | CH₃ | H | |
| 4-Br | 4-CN | 4-F | CH₃ | H | |
| 4-Br | 4-CN | 4-CF₃ | CH₃ | H | |
| 4-Br | 4-CN | 4-CO₂Me | CH₃ | H | |
| 4-Br | 4-CN | 3-Cl | CH₃ | H | |
| 4-Br | 4-CN | 3,4-di-F | CH₃ | H | |
| 4-Br | 4-CN | 4-CN | CH₃ | H | |
| 4-Br | 4-CN | 3-CN | CH₃ | H | |
| 4-Br | 4-H | 4-Cl | CH₃ | H | |
| 4-Br | 4-H | 4-F | CH₃ | H | |
| 4-Br | 4-H | 4-CF₃ | CH₃ | H | |
| 4-Br | 4-H | 4-CO₂Me | CH₃ | H | |
| 4-Br | 4-H | 3-Cl | CH₃ | H | |
| 4-Br | 4-H | 3,4-di-F | CH₃ | H | |
| 4-Br | 4-H | 4-CN | CH₃ | H | |
| 4-Br | 4-H | 3-CN | CH₃ | H | |
| 4-Br | 4-Br | 4-Cl | CH₃ | H | |
| 4-Br | 4-Br | 4-F | CH₃ | H | |
| 4-Br | 4-Br | 4-CF₃ | CH₃ | H | |
| 4-Br | 4-Br | 4-CO₂Me | CH₃ | H | |
| 4-Br | 4-Br | 3-Cl | CH₃ | H | |
| 4-Br | 4-Br | 3,4-di-F | CH₃ | H | |
| 4-Br | 4-Br | 4-CN | CH₃ | H | |
| 4-CF₃ | 4-F | 4-CN | H | CH₂CH₃ | |
| 4-CF₃ | 4-F | 4-CN | H | CO₂Me | |
| 4-CF₃ | 4-F | 4-CN | H | CO₂Et | |
| 4-CF₃ | 4-F | 4-CN | H | COCF₃ | |
| 4-CF₃ | 4-F | 4-CN | H | COCH₂Cl | |
| 4-CF₃ | 4-F | 4-CN | H | COCO₂Me | |
| 4-CF₃ | 4-F | 4-CN | H | —SCCl₃ | |
| 4-CF₃ | 4-F | 4-CN | H | —SC₆H₅ | |
| 4-CF₃ | 4-Cl | 4-F | H | —CO₂Et | |
| 4-CF₃ | 4-Cl | 4-F | H | —CH₂CH₃ | |
| 4-CF₃ | 4-Cl | 4-F | H | —COCH₂Cl | |
| 4-CF₃ | 4-Cl | 4-F | H | —COCH₂CH₃ | |
| 4-CF₃ | 4-Cl | 4-F | H | —S—CCl₃ | |
| 4-CF₃ | 4-Cl | 4-F | H | —S—C₆H₅ | |
| 4-CF₃ | 4-Cl | 4-F | H | propyl | |
| 4-CF₃ | 4-Cl | 4-F | H | butyl | |
| 4-CF₃ | 4-F | 4-Cl | CH₃ | H | |
| 4-CF₃ | 4-F | 4-F | CH₃ | H | |
| 4-CF₃ | 4-Cl | 4-CN | CH₃ | H | |
| 4-CF₃ | 4-Cl | 4-F | CH₃ | H | |
| 4-CF₃ | 4-Cl | 4-Cl | CH₃ | H | 205° to 206 |
| 4-CF₃ | 4-H | 4-CN | CH₃ | H | |
| 4-CF₃ | 4-H | 4-F | CH₃ | H | |
| 4-CF₃ | 4-H | 4-Cl | CH₃ | H | |
| 4-F | 4-F | 4-F | CH₃ | H | |
| 4-F | 4-F | 4-CN | CH₃ | H | |
| 4-F | 4-F | 4-Cl | CH₃ | H | |
| 4-F | 4-Cl | 4-CN | CH₃ | H | |

TABLE 2-continued

| R₁ | R₂ | W | A | Y | m.p. (°C.) |
|---|---|---|---|---|---|
| 4-F | 4-Cl | 4-F | CH₃ | H | |
| 4-F | 4-Cl | 4-Cl | CH₃ | H | |
| 4-F | 4-H | 4-CN | CH₃ | H | |
| 4-F | 4-H | 4-F | CH₃ | H | |
| 4-I | 4-H | 4-Cl | CH₃ | H | |
| 4-Cl | 4-F | 4-CN | CH₃ | H | |
| 4-Cl | 4-Cl | 4-CN | CH₃ | H | |
| 4-CF₃ | 4-Cl | 4-F | H | CH₃ | 164 to 167 |
| 4-CF₃ | 4-Cl | 4-Cl | H | CH₃ | 181 to 183 |
| 4-CF₃ | 4-Cl | 4-CN | H | CH₃ | |
| 4-CF₃ | 4-Cl | 3-CN | H | CH₃ | |
| 4-CF₃ | 4-Cl | 4-CO₂Me | H | CH₃ | |
| 4-CF₃ | 4-Cl | 3,4-di-F | H | CH₃ | |
| 4-CF₃ | 4-Cl | 3-Cl | H | CH₃ | |
| 4-CF₃ | 4-F | 4-F | H | CH₃ | |
| 4-CF₃ | 4-F | 4-Cl | H | CH₃ | |
| 4-CF₃ | 4-F | 4-CN | H | CH₃ | |
| 4-CF₃ | 4-F | 4-CO₂Me | H | CH₃ | |
| 4-CF₃ | 4-F | 3-Cl | H | CH₃ | |
| 4-CF₃ | 4-F | 3-CN | H | CH₃ | |
| 4-CF₃ | 4-F | 3,4-di-F | H | CH₃ | |
| 4-CF₃ | 4-CF₃ | 4-F | H | CH₃ | |
| 4-CF₃ | 4-CF₃ | 4-Cl | H | CH₃ | |
| 4-CF₃ | 4-CF₃ | 4-CN | H | CH₃ | |
| 4-CF₃ | 4-CF₃ | 4-CO₂Me | H | CH₃ | |
| 4-CF₃ | 4-CF₃ | 3-Cl | H | CH₃ | |
| 4-CF₃ | 4-CF₃ | 3-CN | H | CH₃ | |
| 4-CF₃ | 4-CF₃ | 3,4-di-F | H | CH₃ | |
| 4-CF₃ | 4-H | 4-F | H | CH₃ | |
| 4-CF₃ | 4-H | 4-Cl | H | CH₃ | |
| 4-CF₃ | 4-H | 4-CN | H | CH₃ | |
| 4-CF₃ | 4-H | 4-CO₂Me | H | CH₃ | |
| 4-CF₃ | 4-H | 3-Cl | H | CH₃ | |
| 4-CF₃ | 4-H | 3-CN | H | CH₃ | |
| 4-CF₃ | 4-H | 3,4-di-F | H | CH₃ | |
| 4-CF₃ | 4-CN | 4-F | H | CH₃ | |
| 4-CF₃ | 4-CN | 4-Cl | H | CH₃ | |
| 4-CF₃ | 4-CN | 4-CN | H | CH₃ | |
| 4-CF₃ | 4-CN | 4-CO₂Me | H | CH₃ | |
| 4-CF₃ | 4-CN | 3-Cl | H | CH₃ | |
| 4-CF₃ | 4-CN | 3-CN | H | CH₃ | |
| 4-CF₃ | 4-CN | 3,4-di-F | H | CH₃ | |
| 4-OCF₃ | 4-Cl | 4-F | H | CH₃ | |
| 4-OCF₃ | 4-Cl | 4-Cl | H | CH₃ | |
| 4-OCF₃ | 4-Cl | 4-CN | H | CH₃ | |
| 4-OCF₃ | 4-Cl | 3-CN | H | CH₃ | |
| 4-OCF₃ | 4-Cl | 4-CO₂Me | H | CH₃ | |
| 4-OCF₃ | 4-Cl | 3,4-di-F | H | CH₃ | |
| 4-OCF₃ | 4-Cl | 3-Cl | H | CH₃ | |
| 4-OCF₃ | 4-F | 4-F | H | CH₃ | |
| 4-OCF₃ | 4-F | 4-Cl | H | CH₃ | |
| 4-OCF₃ | 4-F | 4-CN | H | CH₃ | |
| 4-OCF₃ | 4-F | 4-CO₂Me | H | CH₃ | |
| 4-OCF₃ | 4-F | 3-Cl | H | CH₃ | |
| 4-OCF₃ | 4-F | 3-CN | H | CH₃ | |
| 4-OCF₃ | 4-F | 3,4-di-F | H | CH₃ | |
| 4-OCF₃ | 4-CF₃ | 4-F | H | CH₃ | |
| 4-OCF₃ | 4-CF₃ | 4-Cl | H | CH₃ | |
| 4-OCF₃ | 4-CF₃ | 4-CN | H | CH₃ | |
| 4-OCF₃ | 4-CF₃ | 4-CO₂Me | H | CH₃ | |
| 4-OCF₃ | 4-CF₃ | 3-Cl | H | CH₃ | |
| 4-OCF₃ | 4-CF₃ | 3-CN | H | CH₃ | |
| 4-OCF₃ | 4-CF₃ | 3,4-di-F | H | CH₃ | |
| 4-OCF₃ | 4-H | 4-F | H | CH₃ | |
| 4-OCF₃ | 4-H | 4-Cl | H | CH₃ | |
| 4-OCF₃ | 4-H | 4-CN | H | CH₃ | |
| 4-OCF₃ | 4-H | 4-CO₂Me | H | CH₃ | |
| 4-OCF₃ | 4-H | 3-Cl | H | CH₃ | |
| 4-OCF₃ | 4-H | 3-CN | H | CH₃ | |
| 4-OCF₃ | 4-H | 3,4-di-F | H | CH₃ | |
| 4-OCF₃ | 4-CN | 4-F | H | CH₃ | |
| 4-OCF₃ | 4-CN | 4-Cl | H | CH₃ | |
| 4-OCF₃ | 4-CN | 4-CN | H | CH₃ | |
| 4-OCF₃ | 4-CN | 4-CO₂Me | H | CH₃ | |
| 4-OCF₃ | 4-CN | 3-Cl | H | CH₃ | |
| 4-OCF₃ | 4-CN | 3-CN | H | CH₃ | |
| 4-OCF₃ | 4-CN | 3,4-di-F | H | CH₃ | |
| 4-Cl | 4-Cl | 4-F | H | CH₃ | |
| 4-Cl | 4-Cl | 4-Cl | H | CH₃ | |
| 4-Cl | 4-Cl | 4-CN | H | CH₃ | |
| 4-Cl | 4-Cl | 3-CN | H | CH₃ | |

TABLE 2-continued

| R₁ | R₂ | W | A | Y | m.p. (°C.) |
|---|---|---|---|---|---|
| 4-Cl | 4-Cl | 4-CO₂Me | H | CH₃ | |
| 4-Cl | 4-Cl | 3,4-di-F | H | CH₃ | |
| 4-Cl | 4-Cl | 3-Cl | H | CH₃ | |
| 4-Cl | 4-F | 4-F | H | CH₃ | |
| 4-Cl | 4-F | 4-Cl | H | CH₃ | |
| 4-Cl | 4-F | 4-CN | H | CH₃ | |
| 4-Cl | 4-F | 4-CO₂Me | H | CH₃ | |
| 4-Cl | 4-F | 3-Cl | H | CH₃ | |
| 4-Cl | 4-F | 3-CN | H | CH₃ | |
| 4-Cl | 4-F | 3,4-di-F | H | CH₃ | |
| 4-Cl | 4-CF₃ | 4-F | H | CH₃ | |
| 4-Cl | 4-CF₃ | 4-Cl | H | CH₃ | |
| 4-Cl | 4-CF₃ | 4-CN | H | CH₃ | |
| 4-Cl | 4-CF₃ | 4-CO₂Me | H | CH₃ | |
| 4-Cl | 4-CF₃ | 3-Cl | H | CH₃ | |
| 4-Cl | 4-CF₃ | 3-CN | H | CH₃ | |
| 4-Cl | 4-CF₃ | 3,4-di-F | H | CH₃ | |
| 4-Cl | 4-H | 4-F | H | CH₃ | |
| 4-Cl | 4-H | 4-Cl | H | CH₃ | |
| 4-Cl | 4-H | 4-CN | H | CH₃ | |
| 4-Cl | 4-H | 4-CO₂Me | H | CH₃ | |
| 4-Cl | 4-H | 3-Cl | H | CH₃ | |
| 4-Cl | 4-H | 3-CN | H | CH₃ | |
| 4-Cl | 4-H | 3,4-di-F | H | CH₃ | |
| 4-Cl | 4-CN | 4-F | H | CH₃ | |
| 4-Cl | 4-CN | 4-Cl | H | CH₃ | |
| 4-Cl | 4-CN | 4-CN | H | CH₃ | |
| 4-Cl | 4-CN | 4-CO₂Me | H | CH₃ | |
| 4-Cl | 4-CN | 3-Cl | H | CH₃ | |
| 4-Cl | 4-CN | 3-CN | H | CH₃ | |
| 4-Cl | 4-CN | 3,4-di-F | H | CH₃ | |
| 4-CF₃ | 4-F | 4-Cl | H | COCF₃ | |
| 4-CF₃ | 4-F | 4-F | H | COCF₃ | |
| 4-CF₃ | 4-Cl | 4-CN | H | COCF₃ | |
| 4-CF₃ | 4-Cl | 4-F | H | COCF₃ | |
| 4-CF₃ | 4-Cl | 4-Cl | H | COCF₃ | |
| 4-F | 4-F | 4-F | H | COCF₃ | |
| 4-F | 4-F | 4-CN | H | COCF₃ | |
| 4-F | 4-F | 4-Cl | H | COCF₃ | |
| 4-F | 4-Cl | 4-CN | H | COCF₃ | |
| 4-F | 4-Cl | 4-F | H | COCF₃ | |
| 4-F | 4-Cl | 4-Cl | H | COCF₃ | |
| 4-Cl | 4-F | 4-CN | H | COCF₃ | |
| 4-Cl | 4-Cl | 4-CN | H | COCF₃ | |
| 4-Cl | 4-F | 4-Cl | H | COCF₃ | |
| 4-CF₃ | 4-F | 4-Cl | H | CO₂Me | |
| 4-CF₃ | 4-F | 4-CN | H | CO₂Me | |
| 4-CF₃ | 4-F | 4-F | H | CO₂Me | |
| 4-CF₃ | 4-Cl | 4-CN | H | CO₂Me | |
| 4-CF₃ | 4-Cl | 4-F | H | CO₂Me | 75 to 78 |
| 4-CF₃ | 4-Cl | 4-Cl | H | CO₂Me | 120 to 124 |
| 4-CF₃ | 4-CF₃ | 4-CN | H | CO₂Me | |
| 4-CF₃ | 4-CF₃ | 4-F | H | CO₂Me | |
| 4-CF₃ | 4-CF₃ | 4-Cl | H | CO₂Me | |
| 4-CF₃ | 4-OCF₃ | 4-CN | H | CO₂Me | |
| 4-CF₃ | 4-OCF₃ | 4-Cl | H | CO₂Me | |
| 4-CF₃ | 4-H | 4-CN | H | CO₂Me | |
| 4-CF₃ | 4-H | 4-F | H | CO₂Me | |
| 4-CF₃ | 4-H | 4-Cl | H | CO₂Me | |
| 4-OCF₃ | 4-F | 4-F | H | CO₂Me | |
| 4-OCF₃ | 4-F | 4-Cl | H | CO₂Me | |
| 4-OCF₃ | 4-Cl | 4-F | H | CO₂Me | |
| 4-OCF₃ | 4-Cl | 4-Cl | H | CO₂Me | |
| 4-OCF₃ | CF₃ | 4-F | H | CO₂Me | |
| 4-OCF₃ | CF₃ | 4-Cl | H | CO₂Me | |
| 4-F | 4-F | 4-F | H | CO₂Me | |
| 4-F | 4-F | 4-CN | H | CO₂Me | |
| 4-F | 4-F | 4-Cl | H | CO₂Me | |
| 4-F | 4-Cl | 4-CN | H | CO₂Me | |
| 4-F | 4-Cl | 4-F | H | CO₂Me | |
| 4-F | 4-Cl | 4-Cl | H | CO₂Me | |
| 4-Cl | 4-F | 4-CN | H | CO₂Me | |
| 4-Cl | 4-Cl | 4-CN | H | CO₂Me | |
| 4-Cl | 4-F | 4-Cl | H | CO₂Me | |
| 4-CF₃ | 4-F | 4-Cl | H | CHO | |
| 4-CF₃ | 4-F | 4-F | H | CHO | |
| 4-CF₃ | 4-Cl | 4-CN | H | CHO | |
| 4-CF₃ | 4-Cl | 4-F | H | CHO | |
| 4-CF₃ | 4-Cl | 4-Cl | H | CHO | |
| 4-F | 4-F | 4-F | H | CHO | |
| 4-F | 4-F | 4-CN | H | CHO | |

TABLE 2-continued

| R$_1$ | R$_2$ | W | A | Y | m.p. (°C.) |
|---|---|---|---|---|---|
| 4-F | 4-F | 4-Cl | H | CHO | |
| 4-F | 4-Cl | 4-CN | H | CHO | |
| 4-F | 4-Cl | 4-F | H | CHO | |
| 4-F | 4-Cl | 4-Cl | H | CHO | |
| 4-Cl | 4-F | 4-CN | H | CHO | |
| 4-Cl | 4-Cl | 4-CN | H | CHO | |
| 4-Cl | 4-F | 4-Cl | H | CHO | |
| 4-CF$_3$ | 4-F | 4-Cl | H | COCH$_3$ | |
| 4-CF$_3$ | 4-F | 4-F | H | COCH$_3$ | |
| 4-CF$_3$ | 4-Cl | 4-CN | H | COCH$_3$ | |
| 4-CF$_3$ | 4-Cl | 4-F | H | COCH$_3$ | 153 to 155 |
| 4-CF$_3$ | 4-Cl | 4-Cl | H | COCH$_3$ | 158 to 160 |
| 4-CF$_3$ | 4-CF$_3$ | 4-F | H | COCH$_3$ | |
| 4-CF$_3$ | 4-CF$_3$ | 4-Cl | H | COCH$_3$ | |
| 4-CF$_3$ | 4-CF$_3$ | 4-CN | H | COCH$_3$ | |
| 4-CF$_3$ | 4-CN | 4-F | H | COCH$_3$ | |
| 4-CF$_3$ | 4-CN | 4-Cl | H | COCH$_3$ | |
| 4-CF$_3$ | 4-CN | 4-CN | H | COCH$_3$ | |
| 4-CF$_3$ | 4-H | 4-F | H | COCH$_3$ | |
| 4-CF$_3$ | 4-H | 4-Cl | H | COCH$_3$ | |
| 4-CF$_3$ | 4-H | 4-CN | H | COCH$_3$ | |
| 4-OCF$_3$ | 4-F | 4-F | H | COCH$_3$ | |
| 4-OCF$_3$ | 4-F | 4-Cl | H | COCH$_3$ | |
| 4-OCF$_3$ | 4-F | 4-CN | H | COCH$_3$ | |
| 4-OCF$_3$ | 4-Cl | 4-F | H | COCH$_3$ | |
| 4-OCF$_3$ | 4-Cl | 4-Cl | H | COCH$_3$ | |
| 4-OCF$_3$ | 4-Cl | 4-CN | H | COCH$_3$ | |
| 4-OCF$_3$ | 4-CF$_3$ | 4-F | H | COCH$_3$ | |
| 4-OCF$_3$ | 4-CF$_3$ | 4-Cl | H | COCH$_3$ | |
| 4-OCF$_3$ | 4-CF$_3$ | 4-CN | H | COCH$_3$ | |
| 4-OCF$_3$ | 4-H | 4-F | H | COCH$_3$ | |
| 4-OCF$_3$ | 4-H | 4-Cl | H | COCH$_3$ | |
| 4-OCF$_3$ | 4-H | 4-CN | H | COCH$_3$ | |
| 4-OCF$_3$ | 4-CN | 4-F | H | COCH$_3$ | |
| 4-OCF$_3$ | 4-CN | 4-Cl | H | COCH$_3$ | |
| 4-OCF$_3$ | 4-CN | 4-CN | H | COCH$_3$ | |
| 4-F | 4-F | 4-F | H | COCH$_3$ | |
| 4-F | 4-F | 4-CN | H | COCH$_3$ | |
| 4-F | 4-F | 4-Cl | H | COCH$_3$ | |
| 4-F | 4-Cl | 4-CN | H | COCH$_3$ | |
| 4-F | 4-Cl | 4-F | H | COCH$_3$ | |
| 4-F | 4-Cl | 4-Cl | H | COCH$_3$ | |
| 4-Cl | 4-F | 4-CN | H | COCH$_3$ | |
| 4-Cl | 4-Cl | 4-CN | H | COCH$_3$ | |
| 4-Cl | 4-F | 4-Cl | H | COCH$_3$ | |
| 4-CF$_3$ | 4-Cl | 4-Cl | H | CH$_2$CH$_3$ | |
| 4-CF$_3$ | 4-Cl | 4-Cl | H | CH$_2$CO$_2$Me | |
| 4-CF$_3$ | 4-Cl | 4-Cl | H | CO$_2$Me | |
| 2,5-di-F | 4-Cl | 4-Cl | CH$_3$ | H | 158 to 159.5 |
| 3,5-di-NO$_2$ | 4-Cl | 4-Cl | CH$_3$ | H | 252.5 to 255 |
| 2,3,4-tri-Cl | 4-Cl | 4-Cl | CH$_3$ | H | 242 to 246 |
| 4-Et | 4-Cl | 4-Cl | CH$_3$ | H | 180 to 181 |
| 3-CF$_3$,4-F | 4-Cl | 4-Cl | CH$_3$ | H | 165 to 166 |
| 4-C$_6$H$_{11}$ | 4-Cl | 4-Cl | CH$_3$ | H | 181 to 182 |
| 3-CN | 4-Cl | 4-Cl | CH$_3$ | H | 112 to 116 |
| 2-CN | 4-Cl | 4-Cl | CH$_3$ | H | 143 to 148 |
| 2-Cl | 4-Cl | 4-Cl | CH$_3$ | H | 157 to 159 |
| 4-F | 4-Cl | 4-Cl | CH$_3$ | H | 141.5 to 142.5 |
| 3-F | 4-Cl | 4-Cl | CH$_3$ | H | 149 to 150 |
| 2-F | 4-Cl | 4-Cl | CH$_3$ | H | 129 to 135 |
| 2,3,4-tri-Cl | 3-CF$_3$ | 4-Cl | CH$_3$ | H | 191 to 192 |
| 3-CF$_3$,4-F | 3-CF$_3$ | 4-Cl | CH$_3$ | H | 188 to 189 |
| 4-OC$_6$H$_5$ | 3-CF$_3$ | 4-Cl | CH$_3$ | H | 110 to 114 |
| 4-CF$_3$ | 3-CF$_3$ | 4-Cl | CH$_3$ | H | 211 to 213 |
| 3-CF$_3$ | 3-CF$_3$ | 4-Cl | CH$_3$ | H | 146 to 148 |
| 4-CN | 3-CF$_3$ | 4-Cl | CH$_3$ | H | 161 to 163 |
| 3-CN | 3-CF$_3$ | 4-Cl | CH$_3$ | H | 189 to 191 |
| 4-Cl | 3-CF$_3$ | 4-Cl | CH$_3$ | H | 178 to 181 |
| 3-Cl | 3-CF$_3$ | 4-Cl | CH$_3$ | H | 122 to 125 |
| 4-F | 3-CF$_3$ | 4-Cl | CH$_3$ | H | 184 to 186 |
| 4-CF$_3$ | 2-Me,4-Cl | 4-Cl | CH$_3$ | H | oil (a) |
| 3-CF$_3$ | 2-Me,4-Cl | 4-Cl | CH$_3$ | H | oil (b) |
| 4-CN | 2-Me,4-Cl | 4-Cl | CH$_3$ | H | oil (c) |
| 3-CN | 2-Me,4-Cl | 4-Cl | CH$_3$ | H | 80 to 82 |
| 4-Cl | 2-Me,4-Cl | 4-Cl | CH$_3$ | H | 82 to 84 |
| 3-Cl | 2-Me,4-Cl | 4-Cl | CH$_3$ | H | 68 to 70 |
| 4-F | 2-Me,4-Cl | 4-Cl | CH$_3$ | H | 82 to 84 |
| 3-CF$_3$,4-F | 2-Me,4-Cl | 4-Cl | CH$_3$ | H | oil (d) |
| 4-CN | 4-CF$_3$ | 4-F | CH$_3$ | H | 94 to 96 |
| 4-F | 4-CF$_3$ | 4-F | CH$_3$ | H | 98 to 100 |
| 4-CF$_3$ | 4-F | 4-H | H | COCH$_3$ | 156 to 158 |

TABLE 2-continued

| $R_1$ | $R_2$ | W | A | Y | m.p. (°C.) |
|---|---|---|---|---|---|
| 4-CF$_3$ | 4-Cl | 4-F | H | COCH$_2$CH$_3$ | 132 to 134 |
| 4-CF$_3$ | 4-OCF$_2$H | 4-F | H | CH$_3$ | oil (e) |

H$^1$NMR spectra (δ):
(a) 8.60(NH)
(b) 8.52(NH)
(c) 8.60(NH)
(d) 8.54(NH)
(e) 3.5(NMe)

TABLE 3

| $R_1$ | $R_2$ | B | A | Y | m.p. (°C.) |
|---|---|---|---|---|---|
| 4-CF$_3$ | 4-F | CH$_3$ | CO$_2$Me | H | 163 to 164 |
| 4-CF$_3$ | 4-H | CH$_3$ | CO$_2$Me | H | |
| 4-CF$_3$ | 4-Cl | CH$_3$ | CO$_2$Me | H | 178.5 to 180 |
| 4-CF$_3$ | 4-Br | CH$_3$ | CO$_2$Me | H | 186 to 188 |
| 4-CF$_3$ | 4-I | CH$_3$ | CO$_2$Me | H | |
| 4-CF$_3$ | 4-CN | CH$_3$ | CO$_2$Me | H | 198 to 203 |
| 4-CF$_3$ | 4-OCF$_2$H | CH$_3$ | CO$_2$Me | H | |
| 4-CF$_3$ | 4-OCF$_3$ | CH$_3$ | CO$_2$Me | H | |
| 4-CF$_3$ | 4-CF$_3$ | CH$_3$ | CO$_2$Me | H | 198 to 199 |
| 4-F | 4-F | CH$_3$ | CO$_2$Me | H | |
| 4-F | 4-H | CH$_3$ | CO$_2$Me | H | |
| 4-F | 4-Cl | CH$_3$ | CO$_2$Me | H | |
| 4-F | 4-Br | CH$_3$ | CO$_2$Me | H | |
| 4-F | 4-I | CH$_3$ | CO$_2$Me | H | |
| 4-F | 4-CN | CH$_3$ | CO$_2$Me | H | |
| 4-Cl | 4-F | CH$_3$ | CO$_2$Me | H | |
| 4-Cl | 4-H | CH$_3$ | CO$_2$Me | H | |
| 4-Cl | 4-Cl | CH$_3$ | CO$_2$Me | H | 138 to 140 |
| 4-Cl | 4-Br | CH$_3$ | CO$_2$Me | H | 132 to 136 |
| 4-Cl | 4-I | CH$_3$ | CO$_2$Me | H | |
| 4-Cl | 4-CN | CH$_3$ | CO$_2$Me | H | 187 to 192 |
| 4-Cl | 4-CF$_3$ | CH$_3$ | CO$_2$Me | H | |
| 4-Cl | 4-OCF$_3$ | CH$_3$ | CO$_2$Me | H | 162 to 165 |
| 4-OCF$_3$ | 4-CF$_3$ | CH$_3$ | CO$_2$Me | H | |
| 4-OCF$_3$ | 4-OCF$_3$ | CH$_3$ | CO$_2$Me | H | |
| 4-OCF$_3$ | 4-Cl | CH$_3$ | CO$_2$Me | H | |
| 4-OCF$_3$ | 4-Br | CH$_3$ | CO$_2$Me | H | gum (oo) |
| 4-OCF$_3$ | 4-H | CH$_3$ | CO$_2$Me | H | |
| 4-OCF$_3$ | 4-CN | CH$_3$ | CO$_2$Me | H | |
| 4-OCF$_3$ | 4-F | CH$_3$ | CO$_2$Me | H | |
| 4-CF$_3$ | 4-F | CH$_3$ | CO$_2$Et | H | |
| 4-CF$_3$ | 4-H | CH$_3$ | CO$_2$Et | H | |
| 4-CF$_3$ | 4-Cl | CH$_3$ | CO$_2$Et | H | |
| 4-CF$_3$ | 4-Br | CH$_3$ | CO$_2$Et | H | |
| 4-CF$_3$ | 4-I | CH$_3$ | CO$_2$Et | H | |
| 4-CF$_3$ | 4-CN | CH$_3$ | CO$_2$Et | H | |
| 4-F | 4-F | CH$_3$ | CO$_2$Et | H | |
| 4-F | 4-H | CH$_3$ | CO$_2$Et | H | |
| 4-F | 4-Cl | CH$_3$ | CO$_2$Et | H | |
| 4-F | 4-Br | CH$_3$ | CO$_2$Et | H | |
| 4-F | 4-I | CH$_3$ | CO$_2$Et | H | |
| 4-F | 4-CN | CH$_3$ | CO$_2$Et | H | |
| 4-Cl | 4-F | CH$_3$ | CO$_2$Et | H | 112.5 to 114 |
| 4-Cl | 4-H | CH$_3$ | CO$_2$Et | H | |
| 4-Cl | 4-Cl | CH$_3$ | CO$_2$Et | H | |
| 4-Cl | 4-Br | CH$_3$ | CO$_2$Et | H | |
| 4-Cl | 4-I | CH$_3$ | CO$_2$Et | H | |
| 4-Cl | 4-CN | CH$_3$ | CO$_2$Et | H | |
| 4-CF$_3$ | 4-F | CH$_3$ | CONMe$_2$ | H | |
| 4-CF$_3$ | 4-H | CH$_3$ | CONMe$_2$ | H | |
| 4-CF$_3$ | 4-Cl | CH$_3$ | CONMe$_2$ | H | |
| 4-CF$_3$ | 4-Br | CH$_3$ | CONMe$_2$ | H | |
| 4-CF$_3$ | 4-I | CH$_3$ | CONMe$_2$ | H | |
| 4-CF$_3$ | 4-CN | CH$_3$ | CONMe$_2$ | H | |
| 4-F | 4-F | CH$_3$ | CONMe$_2$ | H | |
| 4-F | 4-H | CH$_3$ | CONMe$_2$ | H | |
| 4-F | 4-Cl | CH$_3$ | CONMe$_2$ | H | |
| 4-F | 4-Br | CH$_3$ | CONMe$_2$ | H | |
| 4-F | 4-I | CH$_3$ | CONMe$_2$ | H | |
| 4-F | 4-CN | CH$_3$ | CONMe$_2$ | H | |
| 4-Cl | 4-F | CH$_3$ | CONMe$_2$ | H | |
| 4-Cl | 4-H | CH$_3$ | CONMe$_2$ | H | |
| 4-Cl | 4-Cl | CH$_3$ | CONMe$_2$ | H | |
| 4-Cl | 4-Br | CH$_3$ | CONMe$_2$ | H | |
| 4-Cl | 4-I | CH$_3$ | CONMe$_2$ | H | |
| 4-Cl | 4-CN | CH$_3$ | CONMe$_2$ | H | |
| 4-CF$_3$ | 4-OCH$_3$ | CH$_3$ | CO$_2$Me | H | |
| 4-CF$_3$ | 4-NO$_2$ | CH$_3$ | CO$_2$Me | H | |

TABLE 3-continued

| R$_1$ | R$_2$ | B | A | Y | m.p. (°C.) |
|---|---|---|---|---|---|
| 4-CF$_3$ | 4-CO$_2$Et | CH$_3$ | CO$_2$Me | H | |
| 4-CF$_3$ | 4-SMe | CH$_3$ | CO$_2$Me | H | |
| 4-CF$_3$ | 4-SO$_2$Me | CH$_3$ | CO$_2$Me | H | |
| 4-CF$_3$ | 4-Me | CH$_3$ | CO$_2$Me | H | |
| 4-CF$_3$ | 4-CH=CH$_2$ | CH$_3$ | CO$_2$Me | H | |
| 4-CF$_3$ | 4-C≡CH | CH$_3$ | CO$_2$Me | H | |
| 4-CF$_3$ | 4-CONMe$_2$ | CH$_3$ | CO$_2$Me | H | |
| 4-CF$_3$ | 4-SCF$_3$ | CH$_3$ | CO$_2$Me | H | |
| 4-CF$_3$ | 4-OCH(CH$_3$)$_2$ | CH$_3$ | CO$_2$Me | H | |
| 4-CH$_3$ | 4-OSO$_2$CH$_3$ | CH$_3$ | CO$_2$Me | H | |
| 4-CF$_3$ | 4-OCOCH$_3$ | CH$_3$ | CO$_2$Me | H | |
| 4-CF$_3$ | 4-NMe$_2$ | CH$_3$ | CO$_2$Me | H | |
| 4-CF$_3$ | 4-NHCOCH$_3$ | CH$_3$ | CO$_2$Me | H | |
| 4-CF$_3$ | 4-OCONHMe | CH$_3$ | CO$_2$Me | H | |
| 4-CF$_3$ | 4-NHCONH$_2$ | CH$_3$ | CO$_2$Me | H | |
| 4-CF$_3$ | 4-COCH$_3$ | CH$_3$ | CO$_2$Me | H | |
| 4-F | 4-OCH$_3$ | CH$_3$ | CO$_2$Me | H | |
| 4-F | 4-NO$_2$ | CH$_3$ | CO$_2$Me | H | |
| 4-F | 4-CO$_2$Et | CH$_3$ | CO$_2$Me | H | |
| 4-F | 4-SMe | CH$_3$ | CO$_2$Me | H | |
| 4-F | 4-SO$_2$Me | CH$_3$ | CO$_2$Me | H | |
| 4-F | 4-Me | CH$_3$ | CO$_2$Me | H | |
| 4-F | 4-CH=CH$_2$ | CH$_3$ | CO$_2$Me | H | |
| 4-F | 4-C≡CH | CH$_3$ | CO$_2$Me | H | |
| 4-F | 4-CONMe$_2$ | CH$_3$ | CO$_2$Me | H | |
| 4-F | 4-SCF$_3$ | CH$_3$ | CO$_2$Me | H | |
| 4-F | 4-OCH(CH$_3$)$_2$ | CH$_3$ | CO$_2$Me | H | |
| 4-F | 4-OSO$_2$CH$_3$ | CH$_3$ | CO$_2$Me | H | |
| 4-F | 4-OCOCH$_3$ | CH$_3$ | CO$_2$Me | H | |
| 4-F | 4-NMe$_2$ | CH$_3$ | CO$_2$Me | H | |
| 4-F | 4-NHCOCH$_3$ | CH$_3$ | CO$_2$Me | H | |
| 4-F | 4-OCONHMe | CH$_3$ | CO$_2$Me | H | |
| 4-F | 4-NHCONH$_2$ | CH$_3$ | CO$_2$Me | H | |
| 4-F | 4-COCH$_3$ | CH$_3$ | CO$_2$Me | H | |
| 4-OCH$_3$ | 4-F | CH$_3$ | CO$_2$Me | H | |
| 4-NO$_2$ | 4-F | CH$_3$ | CO$_2$Me | H | |
| 4-CO$_2$Et | 4-F | CH$_3$ | CO$_2$Me | H | |
| 4-SMe | 4-F | CH$_3$ | CO$_2$Me | H | |
| 4-SO$_2$Me | 4-F | CH$_3$ | CO$_2$Me | H | |
| 4-Me | 4-F | CH$_3$ | CO$_2$Me | H | |
| 4-CH=CH$_2$ | 4-F | CH$_3$ | CO$_2$Me | H | |
| 4-C≡CH | 4-F | CH$_3$ | CO$_2$Me | H | |
| 4-CONMe$_2$ | 4-F | CH$_3$ | CO$_2$Me | H | |
| 4-SCF$_3$ | 4-F | CH$_3$ | CO$_2$Me | H | |
| 4-OCH(CH$_3$)$_2$ | 4-F | CH$_3$ | CO$_2$Me | H | |
| 4-OSO$_2$CH$_3$ | 4-F | CH$_3$ | CO$_2$Me | H | |
| 4-OCOCH$_3$ | 4-F | CH$_3$ | CO$_2$Me | H | |
| 4-NMe$_2$ | 4-F | CH$_3$ | CO$_2$Me | H | |
| 4-NHCOCH$_3$ | 4-F | CH$_3$ | CO$_2$Me | H | |
| 4-OCONHMe | 4-F | CH$_3$ | CO$_2$Me | H | |
| 4-NHCONH$_2$ | 4-F | CH$_3$ | CO$_2$Me | H | |
| 4-COCH$_3$ | 4-F | CH$_3$ | CO$_2$Me | H | |
| 4-OCH$_3$ | 4-Cl | CH$_3$ | CO$_2$Me | H | |
| 4-NO$_2$ | 4-Cl | CH$_3$ | CO$_2$Me | H | |
| 4-CO$_2$Et | 4-Cl | CH$_3$ | CO$_2$Me | H | |
| 4-SMe | 4-Cl | CH$_3$ | CO$_2$Me | H | |
| 4-SO$_2$Me | 4-Cl | CH$_3$ | CO$_2$Me | H | |
| 4-Me | 4-Cl | CH$_3$ | CO$_2$Me | H | |
| 4-CH=CH$_2$ | 4-Cl | CH$_3$ | CO$_2$Me | H | |
| 4-C≡CH | 4-Cl | CH$_3$ | CO$_2$Me | H | |
| 4-CONMe$_2$ | 4-Cl | CH$_3$ | CO$_2$Me | H | |
| 4-SCF$_3$ | 4-Cl | CH$_3$ | CO$_2$Me | H | |
| 4-OCH(CH$_3$)$_2$ | 4-Cl | CH$_3$ | CO$_2$Me | H | |
| 4-OSO$_2$CH$_3$ | 4-Cl | CH$_3$ | CO$_2$Me | H | |
| 4-OCOCH$_3$ | 4-Cl | CH$_3$ | CO$_2$Me | H | |
| 4-NMe$_2$ | 4-Cl | CH$_3$ | CO$_2$Me | H | |
| 4-NHCOCH$_3$ | 4-Cl | CH$_3$ | CO$_2$Me | H | |
| 4-OCONHMe | 4-Cl | CH$_3$ | CO$_2$Me | H | |
| 4-NHCONH$_2$ | 4-Cl | CH$_3$ | CO$_2$Me | H | |
| 4-COCH$_3$ | 4-Cl | CH$_3$ | CO$_2$Me | H | |
| 4-CF$_3$ | 4-F | CH$_3$ | CO$_2$H | H | |
| 4-CF$_3$ | 4-F | CH$_3$ | COCH$_3$ | H | |
| 4-CF$_3$ | 4-F | CH$_3$ | COCH$_2$CH$_3$ | H | |
| 4-CF$_3$ | 4-F | CH$_3$ | CO$_2$CH$_2$CH$_2$CH$_3$ | H | |
| 4-CF$_3$ | 4-F | CH$_3$ | CO$_2$CH(CH$_3$)$_2$ | H | |
| 4-CF$_3$ | 4-F | CH$_3$ | CO$_2$C$_6$H$_5$ | H | |
| 4-CF$_3$ | 4-F | CH$_3$ | COC$_6$H$_5$ | H | |
| 4-CF$_3$ | 4-F | CH$_2$CH$_3$ | CO$_2$Me | H | |
| 4-CF$_3$ | 4-F | CH$_2$CH$_3$ | CO$_2$Et | H | |
| 4-CF$_3$ | 4-F | CH$_2$CH$_3$ | COCH$_3$ | H | |
| 4-CF$_3$ | 4-F | C$_6$H$_5$ | CO$_2$Me | H | |

TABLE 3-continued

| $R_1$ | $R_2$ | B | A | Y | m.p. (°C.) |
|---|---|---|---|---|---|
| 4-CF$_3$ | 4-F | C$_6$H$_5$ | CO$_2$Et | H | |
| 4-CF$_3$ | 4-F | H | CO$_2$Me | H | |
| 4-CF$_3$ | 4-F | H | COCH$_3$ | H | |
| 4-CF$_3$ | 4-F | H | CO$_2$Et | H | |
| 4-CF$_3$ | 4-F | H | CONMe$_2$ | H | |
| 4-CF$_3$ | 4-F | CH$_2$CH$_3$ | CONMe$_2$ | H | |
| 4-CF$_3$ | 4-Cl | H | CO$_2$Et | H | |
| 4-CF$_3$ | 4-Cl | H | CO$_2$Me | H | 200 to 204 |
| 4-F | 4-Cl | H | CO$_2$Me | H | |
| 4-Cl | 4-Cl | H | CO$_2$Me | H | |
| 4-Cl | 4-CF$_3$ | H | CO$_2$Me | H | 162 to 164.5 |
| 4-F | 4-F | H | CO$_2$Me | H | |
| 4-Cl | 4-F | H | CO$_2$Me | H | 147 to 148 |
| 4-Cl | 4-F | CH$_3$ | CO$_2$C$_6$H$_5$ | H | 161 to 163.5 |
| 4-Cl | 4-CF$_3$ | CH$_2$CO$_2$Me | CO$_2$Me | H | 138 to 142 |
| 4-CF$_3$ | 4-F | CH$_2$CO$_2$Me | CO$_2$Me | H | 155 to 156 |
| 4-CF$_3$ | 4-Cl | CH$_2$CO$_2$Me | CO$_2$Me | H | |
| 4-CF$_3$ | 4-Cl | CH$_2$CN | CO$_2$Me | H | |
| 4-Br | 4-Cl | H | CO$_2$Me | H | 174 to 177 |
| 4-Cl | 4-Cl | H | COCH$_2$CH$_3$ | H | 198 to 199 |
| 4-CF$_3$ | 4-F | CH$_3$ | CO$_2$Me | CHO | |
| 4-CF$_3$ | 4-H | CH$_3$ | CO$_2$Me | CHO | |
| 4-CF$_3$ | 4-Cl | CH$_3$ | CO$_2$Me | CHO | |
| 4-CF$_3$ | 4-Br | CH$_3$ | CO$_2$Me | CHO | |
| 4-CF$_3$ | 4-I | CH$_3$ | CO$_2$Me | CHO | |
| 4-CF$_3$ | 4-CN | CH$_3$ | CO$_2$Me | CHO | |
| 4-F | 4-F | CH$_3$ | CO$_2$Me | CHO | |
| 4-F | 4-H | CH$_3$ | CO$_2$Me | CHO | |
| 4-F | 4-Cl | CH$_3$ | CO$_2$Me | CHO | |
| 4-F | 4-Br | CH$_3$ | CO$_2$Me | CHO | |
| 4-F | 4-I | CH$_3$ | CO$_2$Me | CHO | |
| 4-F | 4-CN | CH$_3$ | CO$_2$Me | CHO | |
| 4-Cl | 4-F | CH$_3$ | CO$_2$Me | CHO | |
| 4-Cl | 4-H | CH$_3$ | CO$_2$Me | CHO | |
| 4-Cl | 4-Cl | CH$_3$ | CO$_2$Me | CHO | |
| 4-Cl | 4-Br | CH$_3$ | CO$_2$Me | CHO | |
| 4-Cl | 4-I | CH$_3$ | CO$_2$Me | CHO | |
| 4-Cl | 4-CN | CH$_3$ | CO$_2$Me | CHO | |
| 4-CF$_3$ | 4-F | CH$_3$ | CO$_2$Me | COCH$_3$ | |
| 4-CF$_3$ | 4-H | CH$_3$ | CO$_2$Me | COCH$_3$ | |
| 4-CF$_3$ | 4-Cl | CH$_3$ | CO$_2$Me | COCH$_3$ | |
| 4-CF$_3$ | 4-Br | CH$_3$ | CO$_2$Me | COCH$_3$ | |
| 4-CF$_3$ | 4-I | CH$_3$ | CO$_2$Me | COCH$_3$ | |
| 4-CF$_3$ | 4-CN | CH$_3$ | CO$_2$Me | COCH$_3$ | |
| 4-F | 4-F | CH$_3$ | CO$_2$Me | COCH$_3$ | |
| 4-F | 4-H | CH$_3$ | CO$_2$Me | COCH$_3$ | |
| 4-F | 4-Cl | CH$_3$ | CO$_2$Me | COCH$_3$ | |
| 4-F | 4-Br | CH$_3$ | CO$_2$Me | COCH$_3$ | |
| 4-F | 4-I | CH$_3$ | CO$_2$Me | COCH$_3$ | |
| 4-F | 4-CN | CH$_3$ | CO$_2$Me | COCH$_3$ | |
| 4-Cl | 4-F | CH$_3$ | CO$_2$Me | COCH$_3$ | |
| 4-Cl | 4-H | CH$_3$ | CO$_2$Me | COCH$_3$ | |
| 4-Cl | 4-Cl | CH$_3$ | CO$_2$Me | COCH$_3$ | |
| 4-Cl | 4-Br | CH$_3$ | CO$_2$Me | COCH$_3$ | |
| 4-Cl | 4-I | CH$_3$ | CO$_2$Me | COCH$_3$ | |
| 4-Cl | 4-CN | CH$_3$ | CO$_2$Me | COCH$_3$ | |
| 4-CF$_3$ | 4-F | CH$_3$ | CO$_2$Me | CO$_2$Me | |
| 4-CF$_3$ | 4-H | CH$_3$ | CO$_2$Me | CO$_2$Me | |
| 4-CF$_3$ | 4-Cl | CH$_3$ | CO$_2$Me | CO$_2$Me | |
| 4-CF$_3$ | 4-Br | CH$_3$ | CO$_2$Me | CO$_2$Me | |
| 4-CF$_3$ | 4-I | CH$_3$ | CO$_2$Me | CO$_2$Me | |
| 4-CF$_3$ | 4-CN | CH$_3$ | CO$_2$Me | CO$_2$Me | |
| 4-F | 4-F | CH$_3$ | CO$_2$Me | CO$_2$Me | |
| 4-F | 4-H | CH$_3$ | CO$_2$Me | CO$_2$Me | |
| 4-F | 4-Cl | CH$_3$ | CO$_2$Me | CO$_2$Me | |
| 4-F | 4-Br | CH$_3$ | CO$_2$Me | CO$_2$Me | |
| 4-F | 4-I | CH$_3$ | CO$_2$Me | CO$_2$Me | |
| 4-F | 4-CN | CH$_3$ | CO$_2$Me | CO$_2$Me | |
| 4-Cl | 4-F | CH$_3$ | CO$_2$Me | CO$_2$Me | |
| 4-Cl | 4-H | CH$_3$ | CO$_2$Me | CO$_2$Me | |
| 4-Cl | 4-Cl | CH$_3$ | CO$_2$Me | CO$_2$Me | |
| 4-Cl | 4-Br | CH$_3$ | CO$_2$Me | CO$_2$Me | |
| 4-Cl | 4-I | CH$_3$ | CO$_2$Me | CO$_2$Me | |
| 4-Cl | 4-CN | CH$_3$ | CO$_2$Me | CO$_2$Me | |
| 4-CF$_3$ | 4-Cl | CH$_3$ | CO$_2$Me | CH$_3$ | oil (a) |
| 4-CF$_3$ | 4-F | CH$_3$ | CO$_2$Me | CH$_3$ | 91 to 95 |
| 4-CF$_3$ | 4-CN | CH$_3$ | CO$_2$Me | CH$_3$ | 145 to 149 |
| 4-CF$_3$ | 4-CF$_3$ | CH$_3$ | CO$_2$Me | CH$_3$ | 114 to 116 |
| 4-CF$_3$ | 4-Br | CH$_3$ | CO$_2$Me | CH$_3$ | 126 to 130 |
| 4-CF$_3$ | 4-OCF$_3$ | CH$_3$ | CO$_2$Me | CH$_3$ | 78 to 82 |
| 4-CF$_3$ | 4-H | CH$_3$ | CO$_2$Me | CH$_3$ | |

TABLE 3-continued

| $R_1$ | $R_2$ | B | A | Y | m.p. (°C.) |
|---|---|---|---|---|---|
| 4-CF$_3$ | 4-Cl | CH$_3$ | CO$_2$Me | CH$_2$CH$_3$ | |
| 4-CF$_3$ | 4-F | CH$_3$ | CO$_2$Me | CH$_2$CH$_3$ | |
| 4-CF$_3$ | 4-CN | CH$_3$ | CO$_2$Me | CH$_2$CH$_3$ | |
| 4-CF$_3$ | 4-CF$_3$ | CH$_3$ | CO$_2$Me | CH$_2$CH$_3$ | |
| 4-CF$_3$ | 4-Br | CH$_3$ | CO$_2$Me | CH$_2$CH$_3$ | |
| 4-CF$_3$ | 4-OCF$_3$ | CH$_3$ | CO$_2$Me | CH$_2$CH$_3$ | |
| 4-CF$_3$ | 4-H | CH$_3$ | CO$_2$Me | CH$_2$CH$_3$ | |
| 4-CF$_3$ | 4-Cl | CH$_3$ | CO$_2$Me | CH$_2$CH$_2$CH$_3$ | |
| 4-CF$_3$ | 4-F | CH$_3$ | CO$_2$Me | CH$_2$CH$_2$CH$_3$ | oil (b) |
| 4-CF$_3$ | 4-CF$_3$ | CH$_3$ | CO$_2$Me | CH$_2$CH$_2$CH$_3$ | oil (c) |
| 4-CF$_3$ | 4-OCF$_3$ | CH$_3$ | CO$_2$Me | CH$_2$CH$_2$CH$_3$ | oil (d) |
| 4-CF$_3$ | 4-CN | CH$_3$ | CO$_2$Me | CH$_2$CH$_2$CH$_3$ | |
| 4-CF$_3$ | 4-Br | CH$_3$ | CO$_2$Me | CH$_2$CH$_2$CH$_3$ | |
| 4-OCF$_3$ | 4-Cl | CH$_3$ | CO$_2$Me | CH$_3$ | |
| 4-OCF$_3$ | 4-F | CH$_3$ | CO$_2$Me | CH$_3$ | |
| 4-OCF$_3$ | 4-CF$_3$ | CH$_3$ | CO$_2$Me | CH$_3$ | |
| 4-OCF$_3$ | 4-CN | CH$_3$ | CO$_2$Me | CH$_3$ | |
| 4-OCF$_3$ | 4-Br | CH$_3$ | CO$_2$Me | CH$_3$ | |
| 4-OCF$_3$ | 4-OCF$_3$ | CH$_3$ | CO$_2$Me | CH$_3$ | |
| 4-Cl | 4-Cl | CH$_3$ | CO$_2$Me | CH$_3$ | |
| 4-Cl | 4-F | CH$_3$ | CO$_2$Me | CH$_3$ | |
| 4-Cl | 4-CF$_3$ | CH$_3$ | CO$_2$Me | CH$_3$ | |
| 4-Cl | 4-CN | CH$_3$ | CO$_2$Me | CH$_3$ | |
| 4-Cl | 4-Br | CH$_3$ | CO$_2$Me | CH$_3$ | |
| 4-Cl | 4-OCF$_3$ | CH$_3$ | CO$_2$Me | CH$_3$ | |
| 4-Br | 4-Cl | CH$_3$ | CO$_2$Me | CH$_3$ | 141 to 142 |
| 4-Br | 4-F | CH$_3$ | CO$_2$Me | CH$_3$ | 151 to 154 |
| 4-Br | 4-CF$_3$ | CH$_3$ | CO$_2$Me | CH$_3$ | |
| 4-Br | 4-CN | CH$_3$ | CO$_2$Me | CH$_3$ | |
| 4-Br | 4-Br | CH$_3$ | CO$_2$Me | CH$_3$ | |
| 4-Br | 4-OCF$_3$ | CH$_3$ | CO$_2$Me | CH$_3$ | oil (e) |
| 4-CF$_3$ | 4-Cl | H | H | H | 167 to 168 |
| 4-CF$_3$ | 4-F | H | H | H | |
| 4-CF$_3$ | 4-CF$_3$ | H | H | H | |
| 4-CF$_3$ | 4-CN | H | H | H | |
| 4-CF$_3$ | 4-H | H | H | H | |
| 4-CF$_3$ | 4-OCF$_3$ | H | H | H | |
| 4-CF$_3$ | 4-Cl | H | H | CH$_3$ | |
| 4-CF$_3$ | 4-Cl | H | H | COCH$_3$ | |
| 4-CF$_3$ | 4-Cl | H | H | CO$_2$CH$_3$ | |
| 4-OCF$_3$ | 4-Cl | H | H | H | |
| 4-OCF$_3$ | 4-CF$_3$ | H | H | H | |
| 4-OCF$_3$ | 4-CN | H | H | H | |
| 4-Cl | 4-Cl | H | H | H | |
| 4-Cl | 4-CF$_3$ | H | H | H | |
| 4-Cl | 4-CN | H | H | H | |
| 4-CF$_3$ | 4-Cl | 4-F-Benzyl | H | H | |
| 4-CF$_3$ | 4-Cl | 4-Cl-Benzyl | H | H | |
| 4-CF$_3$ | 4-Cl | 4-CN-Benzyl | H | H | |
| 4-CF$_3$ | 4-F | 4-F-Benzyl | H | H | |
| 4-CF$_3$ | 4-F | 4-Cl-Benzyl | H | H | |
| 4-CF$_3$ | 4-F | 4-CN-Benzyl | H | H | |
| 4-CF$_3$ | 4-CF$_3$ | 4-F-Benzyl | H | H | |
| 4-CF$_3$ | 4-CF$_3$ | 4-Cl-Benzyl | H | H | |
| 4-CF$_3$ | 4-CF$_3$ | 4-CN-Benzyl | H | H | |
| 4-CF$_3$ | 4-Cl | CH$_2$CH$_2$CH$_3$ | CH$_3$ | H | |
| 4-CF$_3$ | 4-F | CH$_2$CH$_2$CH$_3$ | CH$_3$ | H | 122 to 125 |
| 4-CF$_3$ | 4-CF$_3$ | CH$_2$CH$_2$CH$_3$ | CH$_3$ | H | |
| 4-CF$_3$ | 4-Cl | CH$_2$CH$_2$CH$_2$CH$_3$ | CH$_3$ | H | |
| 4-CF$_3$ | 4-F | CH$_2$CH$_2$CH$_2$CH$_3$ | CH$_3$ | H | |
| 4-CF$_3$ | 4-CF$_3$ | CH$_2$CH$_3$ | CH$_3$ | H | |
| 4-CF$_3$ | 4-Cl | CH$_2$CH$_2$CN | H | H | |
| 4-CF$_3$ | 4-Cl | CH$_2$CH$_2$CH$_2$CN | H | H | |
| 4-CF$_3$ | 4-Cl | CH$_2$CH$_2$CN | CH$_3$ | H | |
| 4-CN | 4-Cl | H | CO$_2$Me | H | 192 to 197 |
| 4-Cl | 4-Cl | H | CO$_2$Me | H | 166 to 168 |
| 2-F, 4-Cl | 4-Cl | H | CO$_2$Me | H | 160 to 170 |
| 4-Cl | 4-CN | H | CO$_2$Me | H | 187 to 190 |
| 4-CN | 4-CN | H | CO$_2$Me | H | 182 to 185 |
| 4-CN | 4-CN | CH$_3$ | CO$_2$Me | H | 205 to 215 |
| 2-F, 4-Cl | 4-CN | CH$_3$ | CO$_2$Me | H | 195 to 197 |
| 4-CN | 4-Cl | CH$_3$ | CONHMe | H | >250 |
| 4-Cl | 4-Cl | H | CONHMe | H | >250 |
| 4-F | 4-CN | CH$_3$ | CN | CONH-n-Bu | 200 to 202 |
| 2-F, 4-Cl | 4-CN | H | CONH-n-Bu | H | 205 to 210 |
| 4-CN | 2-F, 4-Cl | CH$_3$ | CO$_2$Me | H | oil (f) |
| 4-CN | 4-F | CH$_3$ | CHO | H | 116 to 121 |
| 4-F | 4-F | CH$_3$ | CHO | H | 122 to 125 |
| 2,4-di-Cl | 4-F | CH$_3$ | CHO | H | 104 to 113 |
| 4-CF$_3$ | 4-F | i-Pr | CHO | H | 128 to 132 |
| 4-CN | 4-F | i-Pr | CHO | H | 182 to 185 |

TABLE 3-continued

| R₁ | R₂ | B | A | Y | m.p. (°C.) |
|---|---|---|---|---|---|
| 4-F | 4-F | i-Pr | CHO | H | 124 to 129 |
| 2-F, 4-Cl | 4-F | i-Pr | CHO | H | 108 to 115 |
| 4-CF₃ | 4-CF₃ | i-Pr | CHO | H | 133 to 138 |
| 4-CN | 4-CF₃ | i-Pr | CHO | H | foam (g) |
| 4-CF₃ | 4-Cl | i-Pr | CHO | H | 145 to 149 |
| 4-CN | 4-Cl | i-Pr | CHO | H | 160 to 164 |
| 4-CF₃ | 4-CN | CH₃ | CO₂Me | CH₃ | 129 to 130 |
| 4-Br | 4-CF₃ | CH₃ | CO₂Me | H | 128 to 182 |
| 4-Br | 4-CN | CH₃ | CO₂Me | H | 170 to 173 |
| 4-Br | 4-Cl | CH₃ | CO₂Me | H | 147 to 148 |
| 4-Br | 4-Cl | CH₃ | CONHC₆H₄(p-Br) | H | glass (h) |
| 4-Br | 4-F | CH₃ | CO₂Me | H | 153 to 157 |
| 2,4-di-Cl | 4-Cl | i-Pr | CHO | H | glass (i) |
| 4-CF₃ | 4-CF₃ | Me | CONHC₆H₄(p-CF₃) | H | foam (j) |
| 4-CN | 4-CN | i-Pr | CHO | H | oil (k) |
| 4-F | 4-CN | i-Pr | CHO | H | oil (l) |
| 4-CF₃ | 4-F | n-Bu | CO₂Me | CH₃ | oil (m) |
| 4-CF₃ | 4-Cl | n-Bu | CO₂Me | CH₃ | oil (n) |
| 4-CF₃ | 4-CF₃ | n-Bu | CO₂Me | CH₃ | oil (o) |
| 4-I | 4-F | CH₃ | CO₂Me | H | 84 to 85 |
| 4-OCF₃ | 2-F, 4-Cl | CH₃ | CO₂Me | H | 110 to 115 |
| 4-OCF₃ | 2,4-di-Cl | CH₃ | CO₂Me | H | 89 to 92 |
| 4-CF₃ | 2,4-di-Cl | CH₂C₆H₅ | CO₂Me | H | oil (p) |
| 4-F | 2,4-di-Cl | CH₂C₆H₅ | CO₂Me | H | oil (q) |
| 4-CF₃ | 2,4-di-Cl | CH₃ | CO₂Me | H | 145 to 146 |
| 4-Br | 2,4-di-Cl | CH₂C₆H₅ | CO₂Me | H | oil (r) |
| 4-CF₃ | 2,4-di-Cl | CH₂C₆H₅ | CO₂n-Bu | H | oil (s) |
| 4-CF₃ | 2-F, 4-Cl | CH₃ | CO₂n-Bu | H | 129 to 131 |
| 4-CF₃ | 2-F, 4-Cl | CH₃ | CO₂Me | H | 156 to 160 |
| 4-OCF₃ | 2-F, 4-Cl | CH₃ | CO₂n-Bu | H | 123 to 124 |
| 4-CF₃ | 2,4-di-Cl | CH₃ | CO₂n-Bu | CH₃ | oil (t) |
| 4-CF₃ | 4-F | CH₃ | CO₂n-Bu | H | 132 to 140 |
| 4-OCF₃ | 4-F | CH₃ | CO₂n-Bu | H | 109 to 111 |
| 4-CO₂Me | 4-F | CH₃ | CO₂n-Bu | H | 112 to 114 |
| 4-Br | 4-F | CH₃ | CO₂n-Bu | H | 137 to 139 |
| 4-CF₃ | 4-F | CH₃ | CO₂n-Bu | CH₃ | oil (u) |
| 4-CN | 4-F | CH₃ | CO₂n-Bu | CH | 151 to 153 |
| 4-OCF₃ | 4-F | n-Bu | CO₂Me | H | 84 to 87 |
| 4-Br | 4-F | n-Bu | CO₂Me | H | 125 to 128 |
| 4-Br | 4-OCF₃ | CH₃ | CO₂Me | H | oil (v) |
| 4-I | 4-F | n-Bu | CO₂Me | H | 153 to 155 |
| 4-CN | 4-F | n-Bu | CO₂Me | H | 168 to 170 |
| 4-SMe | 4-F | n-Bu | CO₂Me | H | 113 to 115 |
| 4-CF₃ | 4-F | n-Bu | CO₂Me | H | 124 to 126 |
| 4-CN | 4-OCF₃ | CH₃ | CO₂Me | H | 146 to 149 |
| 4-Br | 4-Cl | CH₂C₆H₅ | CO₂Me | H | 185 to 187 |
| 4-F | 4-Cl | CH₂C₆H₅ | CO₂Me | H | 180 to 181 |
| 4-OCF₃ | 4-Cl | CH₂C₆H₅ | CO₂Me | H | 151 to 155 |
| 4-Br | 4-Br | CH₃ | CO₂Me | CH₃ | 144 to 149 |
| 4-CN | 4-Br | CH₃ | CO₂Me | CH₃ | foam (w) |
| 4-Br | 4-Br | CH₃ | CO₂Me | H | 80 to 83 |
| 4-CF₃ | 4-Cl | CH₃ | CO₂-t-Bu | CH₃ | 131 to 132 |
| 4-CF₃ | 4-Br | CH₃ | CONHC₆H₅(p-CF₃) | H | foam (x) |
| 4-Br | 4-Br | CH₃ | CONHC₆H₅(p-Br) | H | glass (y) |
| 4-OCF₃ | 4-Br | CH₃ | CONHC₆H₅(p-CF₃) | H | foam (z) |
| 4-CN | 4-Cl | allyl | CO₂Me | H | 172 to 175.5 |
| 4-SMe | 4-Cl | allyl | CO₂Me | H | 105 to 108.5 |
| 4-CF₃ | 4-Cl | allyl | CO₂Me | H | oil (aa) |
| 4-CF₃ | 4-Cl | allyl | CO₂Me | CH₃ | oil (bb) |
| 4-CF₃ | 4-Cl | allyl | CO₂Me | n-Pr | oil (cc) |
| 4-Br | 4-Cl | allyl | CO₂Me | CH₃ | 125 |
| 4-CF₃ | 4-F | CH₃ | CO₂Me | n-Pr | oil (dd) |
| 4-CF₃ | 4-Cl | CH₃ | CO₂Me | n-Pr | solid (ee) |
| 4-Br | 4-Cl | allyl | CO₂Me | H | oil (ff) |
| 4-I | 4-Cl | CH₃ | CO₂Me | H | |
| 4-OCF₃ | 4-OCF₃ | CH₃ | CO₂-t-Bu | H | oil (gg) |
| 4-CF₃ | 4-OCF₃ | CH₃ | CO₂-t-Bu | H | oil (hh) |
| 4-CF₃ | 4-Br | CH₃ | CO₂-t-Bu | CH₃ | oil (ii) |
| 4-Br | 4-Br | CH₃ | CO₂-t-Bu | H | oil (jj) |
| 4-OCF₃ | 4-Br | CH₃ | CO₂-t-Bu | H | oil (kk) |
| 4-Br | 4-OCF₃ | CH₃ | CO₂-t-Bu | H | oil (ll) |
| 4-CF₃ | 4-Br | CH₃ | CO₂-t-Bu | H | oil (mm) |
| 4-OCF₃ | 4-Br | CH₃ | CO₂-t-Bu | H | oil (nn) |
| 4-Cl | 4-Cl | CH₃ | CHO | H | 203 to 205 |
| 4-CF₃ | 4-F | CH₃ | CHO | H | 178 to 180 |

Infrared spectra $\nu_{CO}(CM^{-1})$:

| | | | | |
|---|---|---|---|---|
| (a) | 1740, 1640 | (b) | 1740, 1635 | |
| (c) | 1745, 1640 | (d) | 1745, 1640 | |
| (e) | 1740, 1640 | (f) | 1745, 1680 | |
| (g) | 1735, 1680 | (h) | 1670, 1660 | |

TABLE 3-continued

| $R_1$ | $R_2$ | B | A | Y | m.p. (°C.) |
|---|---|---|---|---|---|
| | (i) | 1730, 1680 | (j) | | 1705, 1685 |
| | (k) | 1730, 1670 | (l) | | 1730, 1665 |
| | (m) | 1740, 1640 | (n) | | 1740, 1640 |
| | (o) | 1745, 1642 | (p) | | 1740, 1675 |
| | (q) | 1735, 1670 | (r) | | 1735, 1670 |
| | (s) | 1735, 1675 | (t) | | 1740, 1645 |
| | (u) | 1740, 1640 | (v) | | 1740, 1665 |
| | (w) | 1740, 1675 | (x) | | 1690, 1670 |
| | (y) | 1680, 1660 | (z) | | 1675, 1665 |
| | (aa) | 1740, 1680 | (bb) | | 1740, 1640 |
| | (cc) | 1740, 1640 | (dd) | | 1740, 1635 |
| | (ee) | 1740, 1630 | (ff) | | 1740, 1670 |
| | (gg) | 1740, 1675 | (hh) | | 1740, 1675 |
| | (ii) | 1740, 1640 | (jj) | | 1730, 1670 |
| | (kk) | 1740, 1670 | (ll) | | 1740, 1670 |
| | (mm) | 1740, 1670 | (nn) | | 1740, 1670 |
| | | | (oo) | | 1740, 1665 |

TABLE 4

| $R_1$ | $R_2$ | A | -B | Y | X | m.p. (°C.) |
|---|---|---|---|---|---|---|
| 4-$CF_3$ | 4-Cl | 4-F-phenyl | H | H | S | 169 to 171 |
| 4-$CF_3$ | 4-Cl | 4-F-phenyl | $CH_3$ | H | S | |
| 4-$CF_3$ | 4-Cl | 4-F-phenyl | H | $CH_3$ | S | |
| 4-$CF_3$ | 4-Cl | 4-F-phenyl | $CH_3$ | $CH_3$ | S | |
| 4-$CF_3$ | 4-Cl | 4-Cl-phenyl | H | H | S | |
| 4-$CF_3$ | 4-CN | 4-Cl-phenyl | H | H | S | |
| 4-$CF_3$ | 4-F | 4-F-phenyl | H | H | S | |
| 4-$CF_3$ | 4-F | 4-Cl-phenyl | H | H | S | |
| 4-$CF_3$ | 4-F | 4-CN-phenyl | H | H | S | |
| 4-$CF_3$ | 4-$CF_3$ | 4-F-phenyl | H | H | S | |
| 4-$CF_3$ | 4-$CF_3$ | 4-Cl-phenyl | H | H | S | |
| 4-$CF_3$ | 4-$CF_3$ | 4-CN-phenyl | H | H | S | |
| 4-$CF_3$ | 4-$OCF_3$ | 4-F-phenyl | H | H | S | |
| 4-$CF_3$ | 4-$OCF_3$ | 4-Cl-phenyl | H | H | S | |
| 4-$CF_3$ | 4-$OCF_3$ | 4-CN-phenyl | H | H | S | |
| 4-$CF_3$ | 4-H | 4-F-phenyl | H | H | S | |
| 4-$CF_3$ | 4-H | 4-Cl-phenyl | H | H | S | |
| 4-$CF_3$ | 4-H | 4-CN-phenyl | H | H | S | |
| 4-$CF_3$ | 4-CN | 4-F-phenyl | H | H | S | |
| 4-$CF_3$ | 4-CN | 4-Cl-phenyl | H | H | S | |
| 4-$CF_3$ | 4-CN | 4-CN-phenyl | H | H | S | |
| 4-$OCF_3$ | 4-Cl | 4-F-phenyl | H | H | S | |
| 4-$OCF_3$ | 4-Cl | 4-Cl-phenyl | H | H | S | |
| 4-$OCF_3$ | 4-F | 4-F-phenyl | H | H | S | |
| 4-$OCF_3$ | 4-I | 4-Cl-phenyl | H | H | S | |
| 4-$OCF_3$ | 4-$CF_3$ | 4-F-phenyl | H | H | S | |
| 4-$OCF_3$ | 4-$CF_3$ | 4-Cl-phenyl | H | H | S | |
| 4-$OCF_3$ | 4-$OCF_3$ | 4-F-phenyl | H | H | S | |
| 4-$OCF_3$ | 4-$OCF_3$ | 4-Cl-phenyl | H | H | S | |
| 4-Cl | 4-Cl | 4-F-phenyl | H | H | S | |
| 4-Cl | 4-Cl | 4-Cl-phenyl | H | H | S | |
| 4-Cl | 4-F | 4-F-phenyl | H | H | S | |
| 4-Cl | 4-F | 4-Cl-phenyl | H | H | S | |
| 4-Cl | 4-$CF_3$ | 4-F-phenyl | H | H | S | |
| 4-Cl | 4-$CF_3$ | 4-Cl-phenyl | H | H | S | |
| 4-$CF_3$ | 4-Cl | $CO_2Me$ | $CH_3$ | H | S | 76 to 80 |
| 4-$CF_3$ | 4-Cl | $CO_2Me$ | $CH_3$ | $CH_3$ | S | oil (a) |
| 4-$CF_3$ | 4-F | $CO_2Me$ | $CH_3$ | H | S | 120 |
| 4-$CF_3$ | 4-$CF_3$ | $CO_2Me$ | $CH_3$ | H | S | |
| 4-$CF_3$ | 4-$OCF_3$ | $CO_2Me$ | $CH_3$ | H | S | |
| 4-$CF_3$ | 4-Br | $CO_2Me$ | $CH_3$ | H | S | |
| 4-$CF_3$ | 4-CN | $CO_2Me$ | $CH_3$ | H | S | |
| 4-$CF_3$ | 4-H | $CO_2Me$ | $CH_3$ | H | S | |
| 4-$OCF_3$ | 4-Cl | $CO_2Me$ | $CH_3$ | H | S | |
| 4-$OCF_3$ | 4-F | $CO_2Me$ | $CH_3$ | H | S | |
| 4-$OCF_3$ | 4-$CF_3$ | $CO_2Me$ | $CH_3$ | H | S | |
| 4-$OCF_3$ | 4-$OCF_3$ | $CO_2Me$ | $CH_3$ | H | S | |
| 4-Cl | 4-Cl | $CO_2Me$ | $CH_3$ | H | S | |
| 4-Cl | 4-F | $CO_2Me$ | $CH_3$ | H | S | |
| 4-Cl | 4-$CF_3$ | $CO_2Me$ | $CH_3$ | H | S | |
| 4-Cl | 4-$OCF_3$ | $CO_2Me$ | $CH_3$ | H | S | |

TABLE 5

| $R_2$ | A | B | $X_1$ | Physical Properties |
|---|---|---|---|---|
| 4-F | 4-Cl-phenyl | H | OH | solid |
| 4-F | 4-Cl-phenyl | H | Cl | |
| 4-F | 4-F-phenyl | H | OH | |
| 4-F | 4-F-phenyl | H | Cl | |
| 4-F | 4-CN-phenyl | H | OH | $v_{CO} = 1680$ cm$^{-1}$ |
| 4-F | 4-CN-phenyl | H | Cl | |
| 4-Cl | 4-Cl-phenyl | H | OH | |
| 4-Cl | 4-Cl-phenyl | H | Cl | |
| 4-Cl | 4-F-phenyl | H | OH | m.p.: 188 to 191° C. |
| 4-Cl | 4-F-phenyl | H | Cl | $v_{CO} = 1720$ cm$^{-1}$ |
| 4-Cl | 4-CN-phenyl | H | OH | |
| 4-Cl | 4-CN-phenyl | Cl | | |
| 4-Cl | 3,4-di-F-phenyl | H | OH | m.p.: 216 to 217° C. |
| 4-Cl | 3,4-di-F-phenyl | H | Cl | |
| 4-Cl | 3-Cl-phenyl | H | OH | |
| 4-Cl | 3-Cl-phenyl | H | Cl | |
| 4-$CF_3$ | 4-Cl-phenyl | H | OH | |
| 4-$CF_3$ | 4-Cl-phenyl | H | Cl | |
| 4-$CF_3$ | 4-F-phenyl | H | OH | |
| 4-$CF_3$ | 4-F-phenyl | H | Cl | |
| 4-Cl | $CO_2Me$ | $CH_3$ | OH | |
| 4-F | $CO_2Me$ | $CH_3$ | OH | |
| 4-Cl | 4-Cl-phenyl | $CH_3$ | OH | |
| 4-Cl | 4-Cl-phenyl | $CH_3$ | Cl | |
| 4-Cl | 4-F-phenyl | $CH_3$ | OH | |
| 4-Cl | 4-F-phenyl | $CH_3$ | Cl | |
| 4-Cl | 4-Cl-phenyl | H | OMe | m.p.: 103 to 106 |
| 4-Cl | 4-Cl-phenyl | H | OEt | m.p.: 128 to 130° C. |
| 4-Cl | 4-F-phenyl | H | OMe | m.p.: 121 to 123° C. |
| 4-Cl | 4-CN-phenyl | H | OMe | m.p.: 134 to 135.5° C. |
| 4-Cl | 4-$CF_3$-phenyl | H | OMe | NMR: 3.8 (OMe) |
| 4-Cl | 3,4-di-Cl-phenyl | H | OMe | m.p.: 128 to 129° C. |
| 4-Cl | 3,4-di-F-phenyl | H | OMe | m.p.: 154 to 156° C. |
| 4-Cl | 3-Cl-phenyl | H | OMe | NMR: 3.8 (OMe) |
| 4-Cl | 4-Cl-phenyl | $CH_3$ | OMe | NMR: 3.8 (OMe) |
| 4-Cl | 4-F-phenyl | $CH_3$ | OMe | |
| 4-F | 4-Cl-phenyl | H | OMe | NMR: 3.8 (OMe) |
| 4-F | 4-F-phenyl | H | OMe | m.p.: 88 to 90.5° C. |
| 4-F | 4-CN-phenyl | H | OMe | m.p.: 144.5 to 145.5° C. |
| 4-F | 3,4-di-F-phenyl | H | OMe | m.p.: 120 to 121.5° C. |

Formulation and Use

The compounds of this invention will generally be used in formulation with a carrier comprising a liquid or solid diluent or an organic solvent. Useful formulations of the compounds of Formula I can be prepared in conventional ways. They include dusts, granules, pellets, solutions, suspensions, emulsions, wettable powders, emulsifiable concentrates, dry flowables and the like. Many of these can be applied directly. Sprayable formulations can be extended in suitable media and used at spray volumes of from about one to several hundred liters per hectare. High strength compositions are primarily used as intermediates for further formulation. The formulations, broadly, contain about 1% to 99% by weight of active ingredient(s) and at least one of a) about 0.1% to 20% surfactant(s) and b) about 5% to 99% solid or liquid diluent(s). More specifically, they will contain these ingredients in the following approximate proportions:

|  | Percent by Weight | | |
| --- | --- | --- | --- |
|  | Active Ingredient | Diluent(s) | Surfactant(s) |
| Wettable Powders | 25–90 | 0–74 | 1–10 |
| Oil Suspensions, Emulsions, Solutions, (including Emulsifiable Concentrates) | 1–50 | 40–95 | 0–35 |
| Dusts | 1–25 | 70–99 | 0–5 |
| Granules and Pellets | 1–95 | 5–99 | 0–15 |
| High Strength Compositions | 90–99 | 0–10 | 0–2 |

Lower or higher levels of active ingredient can, of course, be present depending on the intended use and the physical properties of the compound. Higher ratios of surfactant to active ingredient are sometimes desirable, and are achieved by incorporation into the formulation or by tank mixing.

Typical solid diluents are described in Watkins, et al., "Handbook of Insecticide Dust Diluents and Carriers", 2nd Ed., Dorland Books, Caldwell, N.J. The more absorptive diluents are preferred for wettable powders and the denser ones for dusts. Typical liquid diluents and solvents are described in Marsden, "Solvents Guide," 2nd Ed., Interscience, New York, 1950. Solubility under 0.1% is preferred for suspension concentrates; solution concentrates are preferably stable against phase separation at 0° C. "McCutcheon's Detergents and Emulsifiers Annual", Allured Publ. Corp., Ridgewood, N.J., as well as Sisely and Wood, "Encyclopedia of Surface Active Agents", Chemical Publ. Co., Inc., New York, 1964, list surfactants and recommended uses. All formulations can contain minor amounts of additives to reduce foam, caking, corrosion, microbiological growth, etc. Preferably, ingredients should be approved by the U.S. Environmental Protection Agency for the use intended.

The methods of making such compositions are well known. Solutions are prepared by simply mixing the ingredients. Fine solid compositions are made by blending and, usually, grinding as in a hammer or fluid energy mill. Suspensions are prepared by wet milling (see, for example, U.S. Pat. No. 3,060,084). Granules and pellets can be made by spraying the active material upon preformed granular carriers or by agglomeration techniques. See Browning, "Agglomeration", *Chemical Engineering*, Dec. 4, 1967, pages 147 and following, and "Perry's Chemical Engineer's Handbook", 4th Ed., McGraw-Hill, New York, 1963, pages 8 to 59 and following.

Many of the compounds of the invention are most efficacious when applied in the form of an emulsifiable concentrate mixed with a spray oil or spray oil concentrate. Although any oil can be used as a spray oil, spray oils usually have these characteristics: they are not phytotoxic to the crop sprayed, and they have appropriate viscosity. Petroleum based oils are commonly used for spraying. In some areas, crop oils are preferred such as the following:

| Common Crop Oils Used as Spray Oils | |
| --- | --- |
| Corn Oil | Linseed Oil |
| Cottonseed Oil | Soybean Oil |
| Coconut Oil | Sunflower Oil |
| Rapeseed Oil | Olive Oil |
| Peanut Oil | Palm Oil |
| Safflower Oil | Sesame Oil |
| Mustardseed Oil | Caster Oil |

The following oils also meet the criteria for a spray oil: mineral, fish and cod liver oil.

Spray oil concentrates comprise a spray oil together with one or more additional ingredients such as emulsifiers and wetting agents. A number of useful spray oil and spray oil concentrates can be found in "A Guide to Agricultural Spray Adjuvants Used in the United States" by Thomson, Thomson Publications, California, 1986.

Examples of useful formulations of compounds of the present invention are as follows:

EXAMPLE 23

Emulsifiable Concentrate

| | |
| --- | --- |
| N,5-bis(4-chlorophenyl)-1-(4-fluorophenyl)-4,5-dihydro-1H-pyrazole-3-carboxamide | 20% |
| blend of oil soluble sulfonates and polyoxyethylene ethers | 10% |
| isophorone | 70% |

The ingredients are combined and stirred with gentle warming to speed solution. A fine screen filter is included in packaging operation to insure the absence of any extraneous undissolved material in the product.

EXAMPLE 24

Wettable Powder

| | |
| --- | --- |
| Methyl 1-(4-chlorophenyl)-4,5-dihydro-5-methyl-3-[[4-(trifluoromethyl)phenyl]aminocarbonyl]-1H-pyrazole-5-carboxylate | 30% |
| sodium alkylnaphthalenesulfonate | 2% |
| sodium ligninsulfonate | 2% |
| synthetic amorphous silica | 3% |
| kaolinite | 63% |

The active ingredient is mixed with the inert materials in a blender. After grinding in a hammermill, the material is re-blended and sifted through a 50 mesh screen.

EXAMPLE 25

Dust

| | |
| --- | --- |
| Wettable powder of Example 24 | 10% |
| pyrophyllite (powder) | 90% |

The wettable powder and the pyrophyllite diluent are thoroughly blended and then packaged. The product is suitable for use as a dust.

EXAMPLE 26

Granule

| | |
| --- | --- |
| 1,5-bis(4-chlorophenyl)-4,5-dihydro-N-[4-(trifluoro- | 10% |

| methyl)phenyl]-1H-pyrazole-3-carboxamide attapulgite granules (low volative matter, 0.71/0.30 mm; U.S.S. No. 25-50 sieves) | 90% |
| --- | --- |

The active ingredient is dissolved in a volatile solvent such as acetone and sprayed upon dedusted and pre-warmed attapulgite granules in a double cone blender. The acetone is then driven off by heating. The granules are then allowed to cool and are packaged.

EXAMPLE 27

Granule

| Wettable powder of Example 24 | 15% |
| --- | --- |
| gypsum | 69% |
| potassium sulfate | 16% |

The ingredients are blended in a rotating mixer and water sprayed on to accomplish granulation. When most of the material has reached the desired range of 0.1 to 0.42 mm (U.S.S. No. 18 to 40 sieves), the granules are removed, dried, and screened. Oversize material is crushed to produce additional material in the desired range. These granules contain 4.5% active ingredient.

EXAMPLE 28

Solution

| N,5-bis(4-chlorophenyl)-1-(4-fluorophenyl)-4,5-dihydro-1H-pyrazole-3-carboxamide | 25% |
| --- | --- |
| N-methyl-pyrrolidone | 75% |

The ingredients are combined and stirred to produce a solution suitable for direct, low volume application.

EXAMPLE 29

Aqueous Suspension

| Methyl 1-(4-chlorophenyl-4,5-dihydro-5-methyl-3-[[4-(trifluoromethyl)phenyl]aminocarbonyl]-1H-pyrazole-5-carboxylate | 40% |
| --- | --- |
| polyacrylic acid thickener | 0.3% |
| dodecyclophenol polyethylene glycol ether | 0.5% |
| disodium phosphate | 1.0% |
| monosodium phosphate | 0.5% |
| polyvinyl alcohol | 1.0% |
| water | 56.7% |

The ingredients are blended and ground together in a sand mill to produce particles essentially all under 5 microns in size.

EXAMPLE 30

Oil Suspension

| Methyl 1-(4-chlorophenyl)-4,5-dihydro-5-methyl-3-[[4-(trifluoromethyl)phenyl]aminocarbonyl]-1H-pyrazole-5-carboxylate | 35.0% |
| --- | --- |
| blend of polyalcohol carboxylic esters and oil soluble petroleum sulfonates | 6.0% |
| xylene range solvent | 59.0% |

The ingredients are combined and ground together in a sand mill to produce particles essentially all below 5 microns. The product can be used directly, extended with oils, or emulsified in water.

EXAMPLE 31

Bait Granules

| Methyl 1-(4-chlorophenyl)-4,5-dihydro-5-methyl-3-[[4-(trifluoromethyl)phenyl]aminocarbonyl]-1H-pyrazole-5-carboxylate | 3.0% |
| --- | --- |
| blend of polyethoxylated nonylphenols and sodium dodecylbenzene sulfonates | 9.0% |
| ground up corn cobs | 88.0% |

The active ingredient and surfactant blend are dissolved in a suitable solvent such as acetone and sprayed onto the ground corn cobs. The granules are then dried and packaged.

Compounds of Formula I can also be mixed with one or more other insecticides, fungicides, nematocides, bactericides, acaricides, or other biologically active compounds to form a multi-component pesticide giving an even broader spectrum of effective agricultural protection. Examples of other agricultural protectants with which compounds of the present invention can be mixed or formulated are:

Insecticides:
3-hydroxy-N-methylcrotonamide(dimethylphosphate)ester (monocrotophos)
methylcarbamic acid, ester with 2,3-dihydro-2,2-dimethyl-7-benzofuranol (carbofuran)
O-[2,4,5-trichloro-α-(chloromethyl)benzyl]phosphoric acid, O', O'-dimethyl ester (tetrachlorvinphos)
2-mercaptosuccinic acid, diethyl ester, S-ester with thionophosphoric acid, dimethyl ester (malathion)
phosphorothioic acid, O,O-dimethyl, O-p-nitrophenyl ester (methyl parathion)
methylcarbamic acid, ester with α-naphthol (carbaryl)
methyl O-(methylcarbamoyl)thiolacetohydroxamate (methomyl)
N'-(4-chloro-o-tolyl)-N,N-dimethylformamidine (chlordimeform)
O,O-diethyl-O-(2-isopropyl-4-methyl-6-pyrimidyl-phosphorothioate (diazinon)
octachlorocamphene (toxaphene)
O-ethyl O-p-nitrophenyl phenylphosphonothioate (EPN)
(S)-α-cyano-m-phenoxybenzyl(1R, 3R)-3-(2,2-dibromovinyl)-2,2-dimethylcyclopropanecarboxylate (deltamethrin)
Methyl N',N'-dimethyl-N-[(methylcarbamoyl)oxy]-1-thiooxamimidate (oxamyl)
cyano(3-phenoxyphenyl)-methyl-4-chloro-α-(1-methylethyl)benzeneacetate (fenvalerate)
(3-phenoxyphenyl)methyl(±)-cis,trans-3-(2,2-dichloroethenyl)-2,2-dimethylcyclopropanecarboxylate (permethrin)
α-cyano-3-phenoxybenzyl 3-(2,2-dichlorovinyl)-2,2-dimethylcyclopropane carboxylate (cypermethrin)

O-ethyl-S-(p-chlorophenyl)ethylphosphonodithioate (profenofos)

phosphorothiolothionic acid, O-ethyl-O-[4-(methylthio)phenyl]-S-n-propyl ester (sulprofos).

Additional insecticides are listed hereafter by their common names: triflumuron, diflubenzuron, methoprene, buprofezin, thiodicarb, acephate, azinphos-methyl, chlorpyrifos, dimethoate, fonophos, isofenphos, methidathion, methamidiphos, monocrotophos, phosmet, phosphamidon, phosalone, pirimicarb, phorate, profenofos, terbufos, trichlorfon, methoxychlor, bifenthrin, biphenate, cyfluthrin, fenpropathrin, fluvalinate, flucythrinate, tralomethrin, metaldehyde and rotenone.

Fungicides:
methyl 2-benzimidazolecarbamate (carbendazim)
tetramethylthiuram disulfide (thiuram)
n-dodecylguanidine acetate (dodine)
manganese ethylenebisdithiocarbamate (maneb)
1,4-dichloro-2,5-dimethoxybenzene (chloroneb)
methyl 1-(butylcarbamoyl)-2-benzimidazolecarbamate (benomyl)
1-[2-(2,4-dichlorophenyl)-4-propyl-1,3-dioxolan-2-ylmethyl]-1H-1,2,4-triazole (propiconazole)
2-cyano-N-ethylcarbamoyl-2-methoxyiminoacetamide (cymoxanil)
1-(4-chlorophenoxy)-3,3-dimethyl-1-(1H-1,2,4-triazol-1-yl)-2-butanone (triadimefon)
N-(trichloromethylthio)tetrahydrophthalimide (captan)
N-(trichloromethylthio)phthalimide (folpet)
1-[[[bis(4-fluorophenyl)][methyl]silyl]methyl]-1H-1,2,4-triazole.

Nematocides:
S-methyl 1-(dimethylcarbamoyl)-N-(methylcarbamoyloxy)thioformimidate
S-methyl 1-carbamoyl-N-(methylcarbamoyloxy)thioformimidate
N-isopropylphosphoramidic acid, O-ethyl O'-[4-(methylthio)-m-tolyl]diester (fenamiphos).

Bactericides:
tribasic copper sulfate
streptomycin sulfate.

Acaricides:
senecioic acid, ester with 2-sec-butyl-4,6-dinitrophenol (binapacryl)
6-methyl-1,3-dithiolo[4,5-$\beta$]quinoxalin-2-one (oxythioquinox)
ethyl 4,4'-dichlorobenzilate (chlorobenzilate)
1,1-bis(p-chlorophenyl)-2,2,2-trichloroethanol (dicofol)
bis(pentachloro-2,4-cyclopentadien-1-yl) (dienochlor)
tricyclohexyltin hydroxide (cyhexatin)
trans-5-(4-chlorophenyl)-N-cyclohexyl-4-methyl-2-oxothiazolidine-3-carboxamide (hexythiazox)
amitraz
propargite
fenbutatin-oxide
bisclofentezin.

Biological
Bacillus thuringiensis
Avermectin B.

Utility

The compounds of the present invention exhibit activity against a wide spectrum of foliar and soil inhabiting insects. Those skilled in the art will recognize that not all compounds are equally effective against all insects, but the compounds of this invention display activity against economically important pest species, such as grasshoppers and cockroaches; thrips; hemipterans: plant bugs (Miridae), such as tarnished plant bug, lace bugs (Tingidae), seed bugs (Lygaeidae) such as cinch bugs, stink bugs (Pentatomidae), leaf-footed bugs (Coreidae), such as squash bug, and red bugs and stainers (Pyrrhocoridae) such as cotton stainer; also homopterans such as whiteflies, leafhoppers, spittlebugs and planthoppers such as aster leafhopper, potato leafhopper and rice planthoppers, psyllids such as pear psylla, scales (coccids and diaspidids) and mealybugs; coleopterans including weevils, such as boll weevil and rice water weevil, grain borers, chrysomellid beetles, such as Colorado potato beetle, flea beetles and other leaf beetles, coccinellid beetles such as Mexican bean beetle, and soil insects such as southern corn rootworm and wireworm; lepidopterous larvae including noctuids such as fall armyworm, beet armyworm, other Spodoptera spp., *Heliothis virescens*, *Heliothis zea*, cabbage looper, green cloverworm, velvetbean caterpillar, cotton leafworm, black cutworm, and other noctuid cutworms and including pyralids such as European corn borer, navel orangeworm, and stalk/stem borers and including tortricids like codling moth and grape berry moth as well as pink bollworm and diamondback moth; and dipterans such as leafminers, soil maggots, midges, tephritid fruit flies. The specific species, for which control is exemplified below, are: fall armyworm, *Spodoptera frugiperda*; tobacco budworm, *Heliothis virescens*; boll weevil, *Anthonomus grandis*; European corn borer, *Ostrinia nubilalis*; southern corn rootworm, *Diabrotica undecimpunctata howardi*; and aster leafhopper, *Macrosteles fascifrons*. The pest control afforded by the compounds of the present invention is not limited, however, to these species.

APPLICATION

Insects are controlled and agricultural crops are protected by applying one or more of the Formula I compounds of this invention, in an effective amount, to the locus of infestation, to the area to be protected, or directly on the pests to be controlled. A preferred method of application is by spraying with spray equipment that distributes the compound on the foliage, in the soil, or to the plant part that is infested or needs to be protected. Alternatively, granular formulations of these compounds can be applied to soil or foliage or, optionally, incorporated into the soil. Either aerial or ground application can be used.

The pyrazoline compound(s) of this invention can be applied directly, but most often application will be of a formulation comprising one or more compounds of this invention, in an agriculturally suitable carrier or diluent. A most preferred method of application involves spraying a water dispersion or refined oil solution of the compounds. Combinations with spray oils and spray oil concentrates often enhance the efficacy of the compounds of Formula I.

The rate of application of the Formula I compounds required for effective control will depend on such factors as the species of insect to be controlled, the pest's life stage, its size, its location, the host crop, time of year of application, ambient moisture, temperature conditions, and the like. In general, application rates of 0.05 to 2 kg of active ingredient per hectare are sufficient to provide effective control in large scale field operations under normal circumstances, but as little as 0.01 kg/hectare may be sufficient or as much as 8 kg/hectare may be required, depending upon the factors listed above. The addition of a compound such as piperonyl butoxide, can enhance the insecticidal activity of the compounds of Formula I.

The following Examples demonstrate the control efficacy of compounds of Formula I on specific insect pests wherein Compounds 1 through 476 and Compounds 1A through 132A are described in Tables 6 and 7, respectively.

Structures for Biological Tables

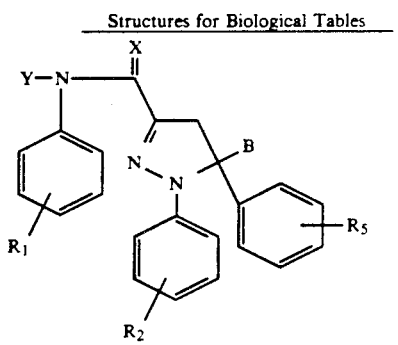

Table 6

-continued
Structures for Biological Tables

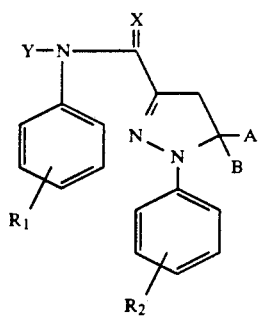

Table 7

TABLE 6

| Compound # | $R_2$ | $R_5$ | $R_1$ | B | Y | X |
|---|---|---|---|---|---|---|
| 1 | 4-F | 4-Cl | 4-Cl | H | H | O |
| 2 | 4-Cl | 4-OMe | H | H | H | O |
| 3 | 4-CF$_3$ | 4-Cl | 4-Cl | H | H | O |
| 4 | 4-Cl | 4-Cl | 4-Cl | H | H | O |
| 5 | 4-Cl | 4-Cl | 4-CF$_3$ | H | H | O |
| 6 | 4-Cl | 4-CN | 4-Cl | H | H | O |
| 7 | 4-Cl | 4-Br | 4-Cl | H | H | O |
| 8 | 4-Cl | 4-Br | 4-CF$_3$ | H | H | O |
| 9 | 4-Cl | 4-OMe | 4-Cl | H | H | O |
| 10 | 4-Cl | 4-Cl | 4-COOEt | H | H | O |
| 11 | 4-Cl | 4-Cl | 4-I | H | H | O |
| 12 | 4-Cl | 4-Cl | 4-F | H | H | O |
| 13 | 4-Cl | 4-Cl | 4-OC$_6$H$_4$p-Cl | H | H | O |
| 14 | 4-Cl | 4-Cl | 4-CN | H | H | O |
| 15 | 4-Cl | 4-Cl | 3-CF$_3$ | H | H | O |
| 16 | 4-Cl | 4-Cl | 4-CF$_3$ | Me | H | O |
| 17 | 4-Cl | 3-Cl | 4-Cl | H | H | O |
| 18 | 4-Cl | 3-Cl | 4-CF$_3$ | H | H | O |
| 19 | 4-Cl | 2-Cl | 4-Cl | H | H | O |
| 20 | 4-Cl | 2-Cl | 4-CF$_3$ | H | H | O |
| 21 | 4-OMe | 4-Cl | 4-CF$_3$ | H | H | O |
| 22 | 4-OMe | 4-Cl | 4-Cl | H | H | O |
| 23 | 4-Cl | 4-CN | 4-CF$_3$ | H | H | O |
| 24 | 4-Cl | 4-Me | 4-CF$_3$ | H | H | O |
| 25 | 4-Cl | 4-Me | 4-F | H | H | O |
| 26 | 4-Cl | 4-CF$_3$ | 4-CF$_3$ | H | H | O |
| 27 | 4-Cl | 4-CF$_3$ | 4-F | H | H | O |
| 28 | 4-Cl | 3,4-di-Cl | 4-CF$_3$ | H | H | O |
| 29 | 4-Cl | 3,4-di-Cl | 4-F | H | H | O |
| 30 | 4-Cl | 4-F | 4-CF$_3$ | H | H | O |
| 31 | 4-Cl | 4-F | 4-F | H | H | O |
| 32 | 4-F | 4-Cl | 4-CF$_3$ | H | H | O |
| 33 | 4-F | 4-Cl | 4-F | H | H | O |
| 34 | H | 4-Cl | 4-CF$_3$ | H | H | O |
| 35 | H | 4-Cl | 4-F | H | H | O |
| 36 | 3-Cl | 4-Cl | 4-CF$_3$ | H | H | O |
| 37 | 3-Cl | 4-Cl | 4-F | H | H | O |
| 38 | 2-Cl | 4-Cl | 4-CF$_3$ | H | H | O |
| 39 | 2-Cl | 4-Cl | 4-F | H | H | O |
| 40 | 4-F | 4-SMe | 4-CF$_3$ | H | H | O |
| 41 | 4-F | 4-F | 4-CF$_3$ | H | H | O |
| 42 | 4-F | 4-F | 4-F | H | H | O |
| 43 | 4-F | 4-CN | 4-CF$_3$ | H | H | O |
| 44 | 4-F | 4-CN | 4-F | H | H | O |
| 45 | 4-F | 4-CN | 4-Cl | H | H | O |
| 46 | H | 4-CN | 4-CF$_3$ | H | H | O |
| 47 | H | 4-CN | 4-F | H | H | O |
| 48 | H | 4-CN | 4-Cl | H | H | O |
| 49 | 4-Cl | 4-CH$_2$CN | 4-Cl | H | H | O |

TABLE 6-continued

| Compound # | R₂ | R₅ | R₁ | B | Y | X |
|---|---|---|---|---|---|---|
| 50 | 4-F | H | 4-Cl | H | H | O |
| 51 | 4-Cl | 4-Cl | 4-CF₃ | H | COMe | O |
| 52 | 4-Cl | 4-Cl | 4-CF₃ | H | Me | O |
| 54 | 4-CF₃ | 4-Cl | 4-F | Me | H | O |
| 55 | 4-CF₃ | 4-Cl | 4-F | Me | H | O |
| 56 | 4-F | 4-Cl | 4-Cl | Me | H | O |
| 57 | 3-Cl | 4-Cl | 4-Cl | Me | H | O |
| 58 | 3-Cl | 4-Cl | 3-Cl | Me | H | O |
| 59 | 4-Cl | 4-Cl | 4-CF₃ | H | COOMe | O |
| 60 | 4-Cl | 4-Cl | 4-CF₃ | H | Et | O |
| 61 | 4-Cl | 4-Cl | 4-CF₃ | H | CH₂COOMe | O |
| 62 | 4-Cl | 4-Cl | 4-OMe | H | H | O |
| 63 | 4-Cl | 4-Cl | 4-i-Pr | H | H | O |
| 64 | 4-Cl | 4-Cl | 4-Me | H | H | O |
| 65 | 4-Cl | 4-Cl | 4-OCF₂CF₂H | H | H | O |
| 66 | 4-Cl | 4-Cl | 3,4-di-Cl | H | H | O |
| 67 | 4-Cl | 4-Cl | 2-F,4-Cl | H | H | O |
| 68 | 4-Cl | 4-Cl | 4-NO₂ | H | H | O |
| 69 | 4-Cl | 4-Cl | 4-Br | H | H | O |
| 70 | 4-CN | 4-Br | 2,5-di-F | H | H | O |
| 71 | 4-CN | 4-Br | 3,5-di-NO₂ | H | H | O |
| 72 | 4-CN | 4-Br | 2,3,4-tri-Cl | H | H | O |
| 73 | 4-CN | 4-Br | 4-Et | H | H | O |
| 74 | 4-CN | 4-Br | 3-CF₃,4-F | H | H | O |
| 75 | 4-CN | 4-Br | 4-C₆H₅ | H | H | O |
| 76 | 4-CN | 4-Br | 4-cyclohexyl | H | H | O |
| 77 | 4-CN | 4-Br | 4-CF₃ | H | H | O |
| 78 | 4-CN | 4-Br | 3-CF₃ | H | H | O |
| 79 | 4-CN | 4-Br | 2-CF₃ | H | H | O |
| 80 | 4-CN | 4-Br | 4-CN | H | H | O |
| 81 | 4-CN | 4-Br | 3-CN | H | H | O |
| 82 | 4-CN | 4-Br | 2-CN | H | H | O |
| 83 | 4-CN | 4-Br | 4-Cl | H | H | O |
| 84 | 4-CN | 4-Br | 3-Cl | H | H | O |
| 85 | 4-CN | 4-Br | 2-Cl | H | H | O |
| 86 | 4-CN | 4-Br | 4-F | H | H | O |
| 87 | 4-CN | 4-Br | 3-F | H | H | O |
| 88 | 4-CN | 4-Br | 2-F | H | H | O |
| 89 | 4-CF₃ | 4-F | 4-CF₃ | H | H | O |
| 90 | 4-CF₃ | 4-F | 3-CF₃ | H | H | O |
| 91 | 4-CF₃ | 4-F | 4-CN | H | H | O |
| 92 | 4-CF₃ | 4-F | 3-CN | H | H | O |
| 93 | 4-CF₃ | 4-F | 4-F | H | H | O |
| 94 | 4-CF₃ | 4-F | 3-F | H | H | O |
| 95 | 4-Cl | 4-CN | 4-NO₂ | H | H | O |
| 96 | 4-Cl | 4-CN | 4-Br | H | H | O |
| 97 | 4-Cl | 4-OMe | 3-Cl | H | H | O |
| 98 | 4-Cl | 4-OMe | 3-CF₃ | H | H | O |
| 99 | 4-Cl | 4-OMe | 3-CF₃,4-F | H | H | O |
| 100 | 4-Cl | 4-OMe | 4-F | H | H | O |
| 101 | 4-Cl | 4-OMe | 4-CN | H | H | O |
| 102 | 4-Cl | 4-OMe | 3-CN | H | H | O |
| 103 | 4-Cl | 4-Cl | 2,5-di-F | Me | H | O |
| 104 | 4-Cl | 4-Cl | 3,5-di-NO₂ | Me | H | O |
| 105 | 4-Cl | 4-Cl | 2,3,4-tri-Cl | Me | H | O |
| 106 | 4-Cl | 4-Cl | 4-Et | Me | H | O |
| 107 | 4-Cl | 4-Cl | 3-CF₃,4-F | Me | H | O |
| 108 | 4-Cl | 4-Cl | 4-cyclohexyl | Me | H | O |
| 109 | 4-Cl | 4-Cl | 3-CN | Me | H | O |
| 110 | 4-Cl | 4-Cl | 2-CN | Me | H | O |
| 111 | 4-Cl | 4-Cl | 4-Cl | Me | H | O |
| 112 | 4-Cl | 4-Cl | 2-Cl | Me | H | O |
| 113 | 4-i-Pr | 4-Cl | 4-CF₃ | H | H | O |
| 114 | 4-i-Pr | 4-Cl | 4-Cl | H | H | O |
| 115 | 4-i-Pr | 4-Cl | 4-OMe | H | H | O |
| 116 | 4-Me | 4-Cl | 4-CF₃ | H | H | O |
| 117 | 4-Me | 4-Cl | 4-Cl | H | H | O |
| 118 | 4-Me | 4-Cl | 4-OMe | H | H | O |
| 119 | 4-Me | 4-Cl | 4-i-Pr | H | H | O |
| 120 | 4-i-Pr | 4-Cl | 4-NO₂ | H | H | O |
| 121 | 4-i-Pr | 4-Cl | 4-i-Pr | H | H | O |
| 122 | 4-Cl | 4-Cl | 4-F | Me | H | O |
| 123 | 4-Cl | 4-Cl | 3-F | Me | H | O |
| 124 | 4-Cl | 4-Cl | 2-F | Me | H | O |
| 125 | 4-Cl | 4-Cl | 2-Me,4-Cl | Me | H | O |
| 126 | 4-CN | 4-F | 2,5-di-F | H | H | O |
| 127 | 4-CN | 4-F | 3,5-di-NO₂ | H | H | O |
| 128 | 4-CN | 4-F | 4-Et | H | H | O |
| 129 | 4-CN | 4-F | 3-CF₃,4-F | H | H | O |
| 130 | 4-CN | 4-F | 4-OC₆H₅ | H | H | O |

TABLE 6-continued

| Compound # | R₂ | R₅ | R₁ | B | Y | X |
|---|---|---|---|---|---|---|
| 131 | 4-CN | 4-F | 4-CF₃ | H | H | O |
| 132 | 4-CN | H | 4-CF₃ | H | H | O |
| 133 | 4-CN | H | 4-t-Bu | H | H | O |
| 134 | 4-CN | H | 4-Cl | H | H | O |
| 135 | 4-CN | H | 4-CN | H | H | O |
| 136 | 4-CN | 4-F | 2,3,4-tri-Cl | H | H | O |
| 137 | 4-CN | 4-F | 3-CF₃ | H | H | O |
| 138 | 4-CN | 4-F | 4-Cl | H | H | O |
| 139 | 4-CN | 4-F | 3-Cl | H | H | O |
| 140 | 4-CN | 4-F | 2-Cl | H | H | O |
| 141 | 4-CN | 4-F | 4-F | H | H | O |
| 142 | 4-CN | 4-F | 3-F | H | H | O |
| 143 | 4-CN | 4-F | 2-F | H | H | O |
| 144 | 4-CF₃ | 4-OC₆H₅ | 2,3,4-tri-Cl | H | H | O |
| 145 | 4-CF₃ | 4-OC₆H₅ | 3-CF₃,4-F | H | H | O |
| 146 | 4-CF₃ | 4-OC₆H₅ | 4-OC₆H₅ | H | H | O |
| 147 | 4-CF₃ | 4-OC₆H₅ | 4-CF₃ | H | H | O |
| 148 | 4-CF₃ | 4-OC₆H₅ | 3-CF₃ | H | H | O |
| 149 | 4-CF₃ | 4-OC₆H₅ | 4-CN | H | H | O |
| 150 | 4-CF₃ | 4-OC₆H₅ | 3-CN | H | H | O |
| 151 | 4-CF₃ | 4-OC₆H₅ | 4-Cl | H | H | O |
| 152 | 4-CF₃ | 4-OC₆H₅ | 3-Cl | H | H | O |
| 153 | 4-CF₃ | 4-OC₆H₅ | 4-F | H | H | O |
| 154 | 4-Cl | 4-Cl | 4-COMe | H | H | O |
| 155 | 4-Cl | 4-Cl | 4-C₆H₅ | H | H | O |
| 156 | 4-Cl | 4-Cl | 4-O-s-Bu | H | H | O |
| 157 | 4-Cl | 4-Cl | 3,4-OCH₂O | H | H | O |
| 158 | 4-Cl | 4-Cl | 3-F,5-F | H | H | O |
| 159 | 3-CF₃ | 4-Cl | 2,3,4-tri-Cl | Me | H | O |
| 160 | 3-CF₃ | 4-Cl | 3-CF₃,4-F | Me | H | O |
| 161 | 3-CF₃ | 4-Cl | 4-OC₆H₅ | Me | H | O |
| 162 | 3-CF₃ | 4-Cl | 4-CF₃ | Me | H | O |
| 163 | 3-CF₃ | 4-Cl | 3-CF₃ | Me | H | O |
| 164 | 3-CF₃ | 4-Cl | 4-CN | Me | H | O |
| 165 | 3-CF₃ | 4-Cl | 3-CN | Me | H | O |
| 166 | 3-CF₃ | 4-Cl | 4-Cl | Me | H | O |
| 167 | 3-CF₃ | 4-Cl | 3-Cl | Me | H | O |
| 168 | 3-CF₃ | 4-Cl | 4-F | Me | H | O |
| 169 | 4-CF₃ | 3-CN | 2,3,4-tri-Cl | H | H | O |
| 170 | 4-CF₃ | 3-CN | 3-CF₃,4-F | H | H | O |
| 171 | 4-CF₃ | 3-CN | 4-OC₆H₅ | H | H | O |
| 172 | 4-CF₃ | 3-CN | 4-CF₃ | H | H | O |
| 173 | 4-CF₃ | 3-CN | 3-CF₃ | H | H | O |
| 174 | 4-CF₃ | 3-CN | 4-CN | H | H | O |
| 175 | 4-CF₃ | 3-CN | 3-CN | H | H | O |
| 176 | 4-CF₃ | 3-CN | 4-Cl | H | H | O |
| 177 | 4-CF₃ | 3-CN | 3-Cl | H | H | O |
| 178 | 4-CF₃ | 3-CN | 4-F | H | H | O |
| 179 | 4-OCF₂CF₂H | 4-Cl | 4-CF₃ | H | H | O |
| 180 | 4-OCF₂CF₂H | 4-Cl | 4-Cl | H | H | O |
| 181 | 4-OCF₂CF₂H | 4-Cl | 4-OCF₂CF₂H | H | H | O |
| 182 | 4-OCF₂CF₂H | 4-Cl | 4-i-Pr | H | H | O |
| 183 | 4-OCF₂CF₂H | H | 4-CF₃ | H | H | O |
| 184 | 4-OCF₂CF₂H | H | 4-Br | H | H | O |
| 185 | 2-Me,4-Cl | 4-Cl | 4-CF₃ | Me | H | O |
| 186 | 2-Me,4-Cl | 4-Cl | 3-CF₃ | Me | H | O |
| 187 | 2-Me,4-Cl | 4-Cl | 4-CN | Me | H | O |
| 188 | 2-Me,4-Cl | 4-Cl | 3-CN | Me | H | O |
| 189 | 2-Me,4-Cl | 4-Cl | 4-Cl | Me | H | O |
| 190 | 2-Me,4-Cl | 4-Cl | 3-Cl | Me | H | O |
| 191 | 2-Me,4-Cl | 4-Cl | 4-F | Me | H | O |
| 192 | 2-Me,4-Cl | 4-Cl | 3-CF₃,4-F | Me | H | O |
| 193 | 2-Me,4-Cl | 4-Cl | 4-CF₃ | H | H | O |
| 194 | 2-Me,4-Cl | 4-Cl | 3-CF₃ | H | H | O |
| 195 | 2-Me,4-Cl | 4-Cl | 4-CN | H | H | O |
| 196 | 2-Me,4-Cl | 4-Cl | 3-CN | H | H | O |
| 197 | 2-Me,4-Cl | 4-Cl | 4-Cl | H | H | O |
| 198 | 2-Me,4-Cl | 4-Cl | 3-Cl | H | H | O |
| 199 | 2-Me,4-Cl | 4-Cl | 4-F | H | H | O |
| 200 | 2-Me,4-Cl | 4-Cl | 3-CF₃,4-F | H | H | O |
| 201 | 2-Me,4-Cl | 4-Cl | 2-Me,4-Cl | H | H | O |
| 202 | 2-Me,4-Cl | 4-Cl | 3-Cl,4-F | H | H | O |
| 203 | 4-CF₃ | H | 4-CF₃ | H | H | O |
| 204 | 4-CF₃ | H | 4-CN | H | H | O |
| 205 | 4-CF₃ | H | 2-CN | H | H | O |
| 206 | 4-CF₃ | H | 4-Cl | H | H | O |
| 207 | 4-CF₃ | H | 3-Cl | H | H | O |
| 208 | 4-CF₃ | H | 2-Cl | H | H | O |
| 209 | 4-CF₃ | H | 4-F | H | H | O |
| 210 | 4-CF₃ | H | 2-F | H | H | O |

TABLE 6-continued

| Compound # | R₂ | R₅ | R₁ | B | Y | X |
|---|---|---|---|---|---|---|
| 211 | 4-CN | H | 4-F | H | H | O |
| 212 | 4-F | H | 4-CF₃ | H | H | O |
| 213 | 4-F | H | 3-CF₃ | H | H | O |
| 214 | 4-F | H | 4-CN | H | H | O |
| 215 | 4-F | H | 3-CN | H | H | O |
| 216 | 4-F | H | 3-Cl | H | H | O |
| 217 | 4-F | H | 4-F | H | H | O |
| 218 | 4-F | H | 3-F | H | H | O |
| 219 | 4-F | H | 3-CF₃,4-F | H | H | O |
| 220 | 4-F | H | 3-Cl₃,4-F | H | H | O |
| 221 | 4-CF₃ | 4-F | 4-CF₃ | Me | H | O |
| 222 | 4-CF₃ | 4-F | 4-CN | Me | H | O |
| 223 | 4-CF₃ | 4-F | 4-Cl | Me | H | O |
| 224 | 4-CF₃ | 4-F | 4-F | Me | H | O |
| 225 | 4-Cl | 4-F | 4-CF₃ | H | COMe | O |
| 226 | 4-F | 4-Cl | 4-NHCOMe | H | H | O |
| 227 | 4-F | 4-Cl | 4-OEt | H | H | O |
| 228 | 4-F | 4-Cl | 4-C₆H₅ | H | H | O |
| 229 | 4-F | 4-Cl | 4-NO₂ | H | H | O |
| 230 | 4-F | 4-Cl | 3-Cl,4-Br | H | H | O |
| 231 | 4-F | 4-Cl | 2-F,4-F | H | H | O |
| 232 | 4-CN | 4-OMe | 4-OMe | H | H | O |
| 233 | 4-CN | 4-OMe | 4-t-Bu | H | H | O |
| 234 | 4-CN | 4-OMe | 4-NO₂ | H | H | O |
| 235 | 4-CN | 4-OMe | 4-CN | H | H | O |
| 236 | 4-CN | 4-OMe | 4-Cl | H | H | O |
| 237 | 4-CN | 4-OMe | 4-CF₃ | H | H | O |
| 238 | 4-CF₃ | 4-C₆H₅ | 4-CF₃ | H | H | O |
| 239 | 4-CF₃ | 4-C₆H₅ | 4-CN | H | H | O |
| 240 | 4-CF₃ | 4-C₆H₅ | 4-Cl | H | H | O |
| 241 | 4-CF₃ | 4-C₆H₅ | 4-F | H | H | O |
| 242 | 4-CF₃ | 4-C₆H₅ | 4-t-Bu | H | H | O |
| 243 | 4-CF₃ | 4-C₆H₅ | 3-F,4-CF₃ | H | H | O |
| 244 | 4-Cl | 2-Cl | 2-OMe | H | H | O |
| 245 | 4-Cl | 2-Cl | 3-OMe | H | H | O |
| 246 | 4-Cl | 2-Cl | 4-OMe | H | H | O |
| 247 | 4-Cl | 2-Cl | 2-Cl | H | H | O |
| 248 | 4-Cl | 2-Cl | 3-Cl | H | H | O |
| 249 | 4-CF | 4-CONEt₂ | 4-CF₃ | H | H | O |
| 250 | 4-CF₃ | 4-CONEt₂ | 4-CN | H | H | O |
| 251 | 4-CF₃ | 4-CONEt₂ | 4-Cl | H | H | O |
| 252 | 4-CF₃ | 4-CONEt₂ | 4-F | H | H | O |
| 253 | 4-Br | 4-Cl | 4-CF₃ | H | H | O |
| 254 | 4-CF₃ | 4-Cl | 4-CF₃ | H | H | O |
| 255 | 4-COOMe | 4-F | 4-CF₃ | H | H | O |
| 256 | 4-COOMe | 4-F | 4-CN | H | H | O |
| 257 | 4-COOMe | 4-F | 4-Cl | H | H | O |
| 258 | 4-COOMe | 4-F | 4-F | H | H | O |
| 259 | 4-COOMe | 4-Cl | 4-CF₃ | H | H | O |
| 260 | 4-COOMe | 4-Cl | 4-CN | H | H | O |
| 261 | 4-COOMe | 4-Cl | 4-Cl | H | H | O |
| 262 | 4-COOMe | 4-Cl | 4-t-Bu | H | H | O |
| 263 | 4-COOMe | 2-Cl | 2-CN | H | H | O |
| 264 | 4-Cl | 2-Cl | 3-CN | H | H | O |
| 265 | 4-Cl | 2-Cl | 4-CN | H | H | O |
| 266 | 4-Cl | 2-Cl | 4-CN | H | H | O |
| 267 | 4-Cl | 2-Cl | 4-t-Bu | H | H | O |
| 268 | 4-Cl | 2-Cl | 2-CH₂C₆H₅ | H | H | O |
| 269 | 4-Cl | 2-Cl | 4-F | H | H | O |
| 270 | 4-Cl | 2-Cl | 4-CF₃ | H | H | O |
| 271 | 2-Cl | 4-F | 3-OMe | H | H | O |
| 272 | 2-Cl | 4-F | 4-OMe | H | H | O |
| 273 | 2-Cl | 4-F | 4-Cl | H | H | O |
| 274 | 2-Cl | 4-F | 3-SO₂NH₂ | H | H | O |
| 275 | 2-Cl | 4-F | 3-SO₂NH₂ | H | H | O |
| 276 | 2-Cl | 4-F | 3-CN | H | H | O |
| 277 | 2-Cl | 4-F | 4-CN | H | H | O |
| 278 | 2-Cl | 4-F | 4-t-Bu | H | H | O |
| 279 | 3-Cl | 4-F | 2-OMe | H | H | O |
| 280 | 3-Cl | 4-F | 3-OMe | H | H | O |
| 281 | 3-Cl | 4-F | 4-OMe | H | H | O |
| 282 | 3-Cl | 4-F | 2-Cl | H | H | O |
| 283 | 3-Cl | 4-F | 3-Cl | H | H | O |
| 284 | 3-Cl | 4-F | 4-Cl | H | H | O |
| 285 | 3-Cl | 4-F | 4-SO₂NH₂ | H | H | O |
| 286 | 3-Cl | 4-F | 2-CN | H | H | O |
| 287 | 3-Cl | 4-F | 3-CN | H | H | O |
| 288 | 3-Cl | 4-F | 4-CN | H | H | O |
| 289 | 3-Cl | 4-F | 4-t-Bu | H | H | O |
| 290 | 3-Cl | 4-F | 2-CH₂C₆H₅ | H | H | O |

TABLE 6-continued

| Compound # | R₂ | R₅ | R₁ | B | Y | X |
|---|---|---|---|---|---|---|
| 291 | 4-t-Bu | 4-C₆H₅ | 4-CF₃ | H | H | O |
| 292 | 4-t-Bu | 4-C₆H₅ | 4-Cl | H | H | O |
| 293 | 4-t-Bu | 4-t-Bu | 4-Cl | H | H | O |
| 294 | 4-t-Bu | 4-t-Bu | 4-CF₃ | H | H | O |
| 295 | 4-t-Bu | 4-t-Bu | 4-NO₂ | H | H | O |
| 296 | 4-t-Bu | 4-t-Bu | 4-CN | H | H | O |
| 297 | 4-t-Bu | 4-t-Bu | 4-OMe | H | H | O |
| 298 | 4-CN | 4-CN | 4-Cl | H | H | O |
| 299 | 4-CN | 4-CN | 4-OMe | H | H | O |
| 300 | 4-Cl | 4-F | 3,4,5-tri-Cl | H | H | O |
| 301 | 4-CN | 4-CN | 4-CF₃ | H | H | O |
| 302 | H | H | 4-CF₃ | H | H | O |
| 303 | 4-Cl | 4-F | 4-Cl | H | H | O |
| 304 | 4-Cl | 4-F | 4-OCF₃ | H | H | O |
| 305 | 4-Cl | 4-F | 4-SCH₃ | H | H | O |
| 306 | 4-Cl | 4-F | 4-COOEt | H | H | O |
| 307 | 3,4-di-Cl | 4-F | 4-CF₃ | H | H | O |
| 308 | 3,4-di-Cl | 4-F | 4-OCF₃ | H | H | O |
| 309 | 3,4-di-Cl | 4-F | 4-C₆H₅ | H | H | O |
| 310 | 3,4-di-Cl | 4-F | 4-SO₂NH₂ | H | H | O |
| 311 | 3,4-di-Cl | 4-F | 4-OEt | H | H | O |
| 312 | 4-CF₃ | 4-COCF₃ | 4-CF₃ | H | H | O |
| 313 | 4-CF₃ | 4-COCF₃ | 4-CH | H | H | O |
| 314 | 4-CF₃ | 4-COCF₃ | 4-Cl | H | H | O |
| 315 | 4-CF₃ | 4-COCF₃ | 4-F | H | H | O |
| 316 | 4-CF₃ | 4-COCF₃ | 4-t-Bu | H | H | O |
| 317 | 4-CF₃ | 4-COCF₃ | 4-COOMe | H | H | O |
| 318 | 4-Cl | 2-Cl | 4-SO₂NH₂ | H | H | O |
| 319 | 3-Cl | 4-F | 4-F | H | H | O |
| 320 | 3-Cl | 4-F | 4-CF₃ | H | H | O |
| 321 | 4-Cl | 2-Cl | 3-SO₂NH₂ | H | H | O |
| 322 | 2-Cl | 4-F | 3-Cl | H | H | O |
| 323 | 2-Cl | 4-F | 2-CN | H | H | O |
| 324 | 4-Cl | 2-Cl | 2-SO₂NH₂ | H | H | O |
| 325 | 2-CN | 4-F | 3-OMe | H | H | O |
| 326 | 2-CN | 4-F | 4-OMe | H | H | O |
| 327 | 2-CN | 4-F | 2-Cl | H | H | O |
| 328 | 2-CN | 4-F | 3-Cl | H | H | O |
| 329 | 2-CN | 4-F | 4-Cl | H | H | O |
| 330 | 2-CN | 4-F | 3-SO₂NH₂ | H | H | O |
| 331 | 2-CN | 4-F | 4-SO₂NH₂ | H | H | O |
| 332 | 2-CN | 4-F | 2-CN | H | H | O |
| 333 | 2-CN | 4-F | 3-CN | H | H | O |
| 334 | 2-CN | 4-F | 4-CN | H | H | O |
| 335 | 2-CN | 4-F | 4-t-Bu | H | H | O |
| 336 | 2-CN | 4-F | 4-CF₃ | H | H | O |
| 337 | 4-Cl | 3-Cl | 2-OMe | H | H | O |
| 338 | 4-Cl | 3-Cl | 3-OMe | H | H | O |
| 339 | 4-Cl | 3-Cl | 4-OMe | H | H | O |
| 340 | 4-Cl | 3-Cl | 2-Cl | H | H | O |
| 341 | 4-Cl | 3-Cl | 3-Cl | H | H | O |
| 342 | 4-Cl | 3-Cl | 2-SO₂NH₂ | H | H | O |
| 343 | 4-Cl | 3-Cl | 3-SO₂NH₂ | H | H | O |
| 344 | 4-Cl | 3-Cl | 2-CN | H | H | O |
| 345 | 4-Cl | 3-Cl | 3-CN | H | H | O |
| 346 | 4-Cl | 3-Cl | 4-t-Bu | H | H | O |
| 347 | 4-Cl | 3-Cl | 2-CH₂C₆H₅ | H | H | O |
| 348 | 4-Cl | 3-Cl | 4-CN | H | H | O |
| 349 | 4-Cl | 3-Cl | 4-COO-n-Pr | H | H | O |
| 350 | 4-Cl | 3-Cl | 3,5-Cl | H | H | O |
| 351 | 4-Cl | 4-F | 4-CF₃ | H | COOMe | O |
| 352 | 4-Cl | 4-F | 4-CF₃ | H | Me | O |
| 353 | 4-Cl | 4-F | 4-COO-n-Pr | H | H | O |
| 354 | 4-Cl | 4-F | 4-CF₃ | H | H | O |
| 355 | 4-CF₃ | 4-COOH | 4-CF₃ | H | H | O |
| 356 | 4-CF₃ | 4-COOH | 4-CN | H | H | O |
| 357 | 4-CF₃ | 4-COOH | 4-Cl | H | H | O |
| 358 | 4-CF₃ | 4-COOH | 4-F | H | H | O |
| 359 | 4-CF₃ | 4-COOH | 4-t-Bu | H | H | O |
| 360 | 4-CF₃ | 4-CF₃ | 4-CF₃ | H | H | O |
| 361 | 4-CF₃ | 4-CF₃ | 4-Cl | H | H | O |
| 362 | 4-CF₃ | C₂H₃ | 4-CF₃ | H | H | O |
| 363 | 4-NO₂ | 4-F | 4-CF₃ | H | H | O |
| 364 | 4-NH₂ | 4-F | 4-CF₃ | H | H | O |
| 365 | 4-SO₂CH₃ | 4-F | 4-CF₃ | H | H | O |
| 366 | 4-Cl | 3-Cl | 3-SO₂NH₂ | H | H | O |
| 367 | 2-OMe | 4-F | 4-CN | H | H | O |
| 368 | 2-OMe | 4-F | 2-CH₂C₆H₅ | H | H | O |
| 369 | 2-OMe | 4-F | 4-CF₃ | H | H | O |
| 370 | 2-OMe | 4-F | 2-OMe | H | H | O |

TABLE 6-continued

| Compound # | R₂ | R₅ | R₁ | B | Y | X |
|---|---|---|---|---|---|---|
| 371 | 2-OMe | 4-F | 4-OMe | H | H | O |
| 372 | 2-OMe | 4-F | 2-Cl | H | H | O |
| 373 | 2-OMe | 4-F | 4-Cl | H | H | O |
| 374 | 2-OMe | 4-F | 4-SO₂NH₂ | H | H | O |
| 375 | 2-OMe | 4-F | 2-CN | H | H | O |
| 376 | 2-OMe | 4-F | 3-OMe | H | H | O |
| 377 | 2-OMe | 4-F | 3-Cl | H | H | O |
| 378 | 4-Cl | 2-OMe | 3-OMe | H | H | O |
| 379 | 2-OMe | 4-F | 4-t-Bu | H | H | O |
| 380 | 2-OMe | 4-F | 3-CH | H | H | O |
| 381 | 4-Cl | 2-OMe | 4-OMe | H | H | O |
| 382 | 4-Cl | 2-OMe | 2-Cl | H | H | O |
| 383 | 4-Cl | 2-OMe | 3-Cl | H | H | O |
| 384 | 4-Cl | 2-OMe | 4-Cl | H | H | O |
| 385 | 4-Cl | 2-OMe | 2-CO₂NH₂ | H | H | O |
| 386 | 4-Cl | 2-OMe | 2-SO₂NH₂ | H | H | O |
| 387 | 4-Cl | 2-OMe | 2-OMe | H | H | O |
| 388 | 4-Cl | 2-OMe | 2-CN | H | H | O |
| 389 | 4-Cl | 2-OMe | 3-CN | H | H | O |
| 390 | 4-Cl | 2-OMe | 4-CN | H | H | O |
| 391 | 4-Cl | 2-OMe | 2-CH₂C₆H₅ | H | H | O |
| 392 | 4-Cl | 2-OMe | 4-CF₃ | H | H | O |
| 393 | 4-Cl | 2-OMe | 3-SO₂NH₂ | H | H | O |
| 394 | 4-Cl | 2-OMe | 4-t-Bu | H | H | O |
| 395 | 3-Cl | 4-F | 2-SO₂NH₂ | H | H | O |
| 396 | 3-Cl | 4-F | 3-SO₂NH₂ | H | H | O |
| 397 | 2-OMe | 4-F | 2-SO₂NH₂ | H | H | O |
| 398 | 2-OMe | 4-F | 3-SO₂NH₂ | H | H | O |
| 399 | 2-CH₂C₆H₅ | 4-F | 4-OMe | H | H | O |
| 400 | 4-F | 3,4-F | 4-CF₃ | H | H | O |
| 401 | 4-F | 3,4-F | 4-OCF₃ | H | H | O |
| 402 | 4-F | 3,4-F | 4-Cl | H | H | O |
| 403 | 4-F | 3,4-F | 4-Br | H | H | O |
| 404 | 4-CN | 4-CN | 4-CN | H | H | O |
| 405 | 4-CN | 4-CN | 4-t-Bu | H | H | O |
| 406 | 4-Cl | 4-OMe | 4-OMe | H | H | O |
| 407 | 4-Cl | 4-OMe | 4-NO₂ | H | H | O |
| 408 | 4-Cl | 4-OMe | 4-CF₃ | H | H | O |
| 409 | 4-Cl | 4-OMe | 4-t-Bu | H | H | O |
| 410 | 4-OCF₃ | 4-F | 4-CF₃ | H | H | O |
| 411 | 4-OCF₃ | 4-F | 4-OCF₃ | H | H | O |
| 412 | 4-OCF₃ | 4-F | 4-Cl | H | H | O |
| 413 | 4-OCF₃ | 4-F | 4-Br | H | H | O |
| 414 | 4-Cl | 3,4-F | 4-CF₃ | H | H | O |
| 415 | 4-Cl | 3,4-F | 4-OCF₃ | H | H | O |
| 416 | 4-Cl | 3,4-F | 4-OCF₂CF₂H | H | H | O |
| 417 | 4-Cl | 3,4-F | 4-Cl | H | H | O |
| 418 | 4-Cl | 4-Cl | 3,4,5-tri-Cl | H | H | O |
| 419 | 4-Cl | 4-Cl | 4-OCF₃ | H | H | O |
| 420 | 4-CF₃ | 4-F | 4-CF₃ | H | H | O |
| 421 | 2-CH₂C₆H₅ | 4-F | 4-CN | H | H | O |
| 422 | 2-CH₂C₆H₅ | 4-F | 4-t-Bu | H | H | O |
| 423 | 2-CH₂C₆H₅ | 4-F | 4-CF₃ | H | H | O |
| 424 | 3,4-di-F | 4-F | 4-CF₃ | H | H | O |
| 425 | 3,4-di-F | 4-F | 4-OCF₃ | H | H | O |
| 426 | 3,4-di-F | 4-F | 4-SMe | H | H | O |
| 427 | 3,4-di-F | 4-F | 4-Br | H | H | O |
| 428 | 3,4-di-F | 4-F | 4-CO₂NH | H | H | O |
| 429 | 3,4-di-F | 4-F | 4-C₆H₅ | H | H | O |
| 430 | 3,4-di-F | 4-F | 4-Cl | H | H | O |
| 431 | 3,4-di-F | 4-F | 4-OEt | H | H | O |
| 432 | 4-F | H | 4-CF₃ | H | Ac | O |
| 433 | 4-NO₂ | 4-Cl | 4-F | H | H | O |
| 434 | 4-CF₃ | 4-Cl | 4-CF₃ | Me | H | O |
| 435 | 4-Cl | 4-t-Bu | 4-Cl | H | H | O |
| 436 | 4-Cl | 4-t-Bu | 4-OMe | H | H | O |
| 437 | 4-Cl | 4-t-Bu | 4-CN | H | H | O |
| 438 | 4-Cl | 4-t-Bu | 4-CF₃ | H | H | O |
| 439 | 4-Cl | 4-t-Bu | 4-t-Bu | H | H | O |
| 440 | 4-Cl | 4-t-Bu | 4-NO₂ | H | H | O |
| 441 | 4-Cl | 4-C₆H₅ | 4-Cl | H | H | O |
| 442 | 4-Cl | 4-C₆H₅ | 4-OMe | H | H | O |
| 443 | 4-Cl | 4-C₆H₅ | 4-CN | H | H | O |
| 444 | 4-Cl | 4-C₆H₅ | 4-CF₃ | H | H | O |
| 445 | 4-Cl | 4-C₆H₅ | 4-t-Bu | H | H | O |
| 446 | 4-Cl | 4-C₆H₅ | 4-NO₂ | H | H | O |
| 447 | 4-CF₃ | 4-Br | 4-CF₃ | H | H | O |
| 448 | 4-CF₃ | 4-Br | 4-CN | H | H | O |
| 449 | 4-CF₃ | 4-Br | 4-Cl | H | H | O |
| 450 | 4-CF₃ | 4-Br | 4-F | H | H | O |

TABLE 6-continued

| Compound # | R₂ | R₅ | R₁ | B | Y | X |
|---|---|---|---|---|---|---|
| 451 | 4-CF₃ | 4-Br | 4-NO₂ | H | H | O |
| 452 | 4-F | 4-COOMe | 4-CF₃ | H | H | O |
| 453 | 4-F | 4-COOMe | 4-CN | H | H | O |
| 454 | 4-F | 4-COOMe | 4-Cl | H | H | O |
| 455 | 4-F | 4-COOMe | 4-F | H | H | O |
| 456 | 4-F | 4-COOMe | 4-t-Bu | H | H | O |
| 457 | 4-F | 4-COOMe | 3-CF₃,4-F | H | H | O |
| 458 | 4-Cl | 4-F | 4-CF₃ | Me | H | O |
| 459 | 4-CF₃ | 4-COOMe | 4-CF₃ | H | H | O |
| 460 | 4-CF₃ | 4-COOMe | 4-CN | H | H | O |
| 461 | 4-CF₃ | 4-COOMe | 4-Cl | H | H | O |
| 462 | 4-CF₃ | 4-COOMe | 4-F | H | H | O |
| 463 | 4-CF₃ | 4-COOMe | 4-COOMe | H | H | O |
| 464 | 4-NO₂ | 4-Cl | 4-CF₃ | H | H | O |
| 465 | 4-Cl | 4-F | 4-CF₃ | H | COEt | O |
| 466 | 4-CF₃ | 4-Br | 4-NH₂ | H | H | O |
| 467 | 4-Cl | 4-COOMe | 4-CF₃ | H | H | O |
| 468 | 4-CF | 4-CONHC₆H₄(p-CF₃) | 4-CF₃ | H | H | O |
| 469 | 4-Cl | 4-COOMe | 4-Cl | H | H | O |
| 470 | 4-Cl | 4-CONHC₆H₄(p-Cl) | 4-Cl | H | H | O |
| 471 | 4-Cl | 4-COOMe | 4-F | H | H | O |
| 472 | 4-NH₂ | 4-Cl | 4-CF | H | H | O |
| 473 | 4-Br | 4-F | 4-CF | H | H | O |
| 474 | 4-Br | 4-F | 4-Cl | H | H | O |
| 475 | 4-Br | 4-F | 4-F | H | H | O |

TABLE 7

| Compound # | R₂ | R₁ | B | A | X | Y |
|---|---|---|---|---|---|---|
| 1A | 4-F | 4-Cl | H | COOMe | O | H |
| 2A | 4-F | 4-Cl | Me | COOEt | O | H |
| 3A | 4-Cl | H | H | COOMe | O | H |
| 4A | 4-CF₃ | 4-Cl | H | COOMe | O | H |
| 5A | 4-CF₃ | 4-Cl | CH₂COOMe | COOMe | O | H |
| 6A | 4-Cl | 4-CF₃ | H | COOMe | O | H |
| 7A | 4-Cl | 4-CF₃ | Me | COOMe | O | H |
| 8A | 4-F | 4-Cl | Me | COOC₆H₅ | O | H |
| 9A | 4-Cl | 4-Cl | Me | COOMe | O | H |
| 10A | 4-Cl | 4-Cl | Me | CN | O | H |
| 11A | 4-Cl | 4-Cl | Me | CHO | O | H |
| 12A | 4-Cl | 4-Cl | H | COEt | O | H |
| 13A | 4-F | 4-CF₃ | Me | COOMe | O | H |
| 14A | 4-F | 4-CF₃ | Me | CHO | O | H |
| 15A | 4-F | 4-CF₃ | CH₂COOMe | COOMe | O | H |
| 16A | 4-Cl | 4-Br | H | COOMe | O | H |
| 17A | 4-Cl | 4-CN | H | COOMe | O | H |
| 18A | 4-Cl | 4-Cl | H | COOMe | O | H |
| 19A | 4-Cl | 2-F,4-Cl | H | COOMe | O | H |
| 20A | 4-CN | 4-Cl | H | COOMe | O | H |
| 21A | 4-CN | 4-CN | H | COOMe | O | H |
| 22A | 4-CN | 4-Cl | Me | COOMe | O | H |
| 23A | 4-CN | 4-CN | Me | COOMe | O | H |
| 24A | 4-CN | 2-F,4-Cl | Me | COOMe | O | H |
| 25A | 4-F | 4-CF₃ | Me | CHO | O | H |
| 26A | 4-Cl | 4-CN | Me | CONHMe | O | H |
| 27A | 4-Cl | 4-Cl | H | CONHMe | O | H |
| 28A | 4-CN | 4-F | Me | CN | O | H |
| 29A | 4-Cl | 2-F,4-Cl | H | CONHnBu | O | H |
| 30A | 2-F,4-Cl | 4-CN | Me | COOMe | O | H |
| 31A | 4-F | 4-CN | Me | CHO | O | H |
| 32A | 4-F | 4-F | Me | CHO | O | H |
| 33A | 4-F | 2,4-di-Cl | Me | CHO | O | H |
| 34A | 4-Cl | 4-CF₃ | H | H | O | H |
| 35A | 4-CN | 4-CF₃ | Me | COOMe | O | H |
| 36A | 4-F | 4-CF₃ | i-Pr | CHO | O | H |
| 37A | 4-F | 4-CN | i-Pr | CHO | O | H |
| 38A | 4-F | 4-F | i-Pr | CHO | O | H |
| 39A | 4-F | 2-F,4-Cl | i-Pr | CHO | O | H |
| 40A | 4-CF₃ | 4-CF₃ | i-Pr | CHO | O | H |
| 41A | 4-CF₃ | 4-CN | i-Pr | CHO | O | H |
| 42A | 4-CN | 4-CF₃ | i-Pr | CHO | O | H |
| 43A | 4-Cl | 4-CF₃ | i-Pr | CHO | O | H |
| 44A | 4-Cl | 4-CN | i-Pr | CHO | O | H |
| 45A | 4-CF₃ | 4-CF₃ | Me | COOMe | O | H |
| 46A | 4-CF₃ | 4-CF₃ | Me | COOMe | O | H |
| 47A | 4-CN | 4-CF₃ | Me | COOMe | O | H |
| 48A | 4-F | 4-CF₃ | Me | COOMe | O | H |

TABLE 7-continued

| Compound # | R₂ | R₁ | B | A | X | Y |
|---|---|---|---|---|---|---|
| 49A | 4-CF₃ | 4-Br | Me | COOMe | O | H |
| 50A | 4-CN | 4-Br | Me | COOMe | O | H |
| 51A | 4-Cl | 4-Br | Me | COOMe | O | H |
| 52A | 4-Cl | 4-Br | Me | CONHC₆H₄Br | O | H |
| 53A | 4-F | 4-Br | Me | COOMe | O | H |
| 54A | 4-Cl | 4-CF₃ | Me | COOMe | O | Me |
| 55A | 4-Cl | 2,4-di-Cl | i-Pr | CHO | O | H |
| 56A | 4-CF₃ | 4-CF₃ | Me | CONHC₆H₄CF₃ | O | H |
| 57A | 4-CN | 4-CN | i-Pr | CHO | O | H |
| 58A | 4-CN | 4-F | i-Pr | CHO | O | H |
| 59A | 4-F | 4-CF₃ | n-Bu | COOMe | O | Me |
| 60A | 4-Cl | 4-CF₃ | n-Bu | COOMe | O | Me |
| 61A | 4-CF₃ | 4-CF₃ | n-Bu | COOMe | O | Me |
| 62A | 4-F | 4-I | Me | COOMe | O | H |
| 63A | 2,4-di-Cl | 4-OCF₃ | Me | COOMe | O | H |
| 64A | 2,4-di-Cl | 4-OCF₃ | Me | COOMe | O | H |
| 65A | 2,4-di-Cl | 4-CF₃ | CH₂C₆H₅ | COOMe | O | H |
| 66A | 2,4-di-Cl | 4-F | CH₂C₆H₅ | COOMe | O | H |
| 67A | 2,4-di-Cl | 4-CF₃ | Me | COOMe | O | H |
| 68A | 2,4-di-Cl | 4-Br | CH₂C₆H₅ | COOn-Bu | O | H |
| 69A | 2,4-di-Cl | 4-CF₃ | Me | COOn-Bu | O | H |
| 70A | 2-F,4-Cl | 4-CF₃ | Me | COOn-Bu | O | H |
| 71A | 2-F,4-Cl | 4-CF₃ | Me | COOnMe | O | H |
| 72A | 2-F,4-Cl | 4-OCF₃ | Me | COOn-Bu | O | H |
| 73A | 2-F,4-Cl | 4-CF₃ | Me | COOn-Bu | O | H |
| 74A | 4-F | 4-CF₃ | Me | n-Pr | O | H |
| 75A | 4-F | 4-CF₃ | Me | COOn-Bu | O | H |
| 76A | 4-F | 4-OCF₃ | Me | COOn-Bu | O | H |
| 77A | 4-F | 4-COOMe | Me | COOn-Bu | O | H |
| 78A | 4-F | 4-Br | Me | COOn-Bu | O | H |
| 79A | 4-F | 4-CF₃ | Me | COOn-Bu | O | H |
| 80A | 4-F | 4-CN | Me | COOn-Bu | O | H |
| 81A | 4-F | 4-OCF₃ | n-Bu | COOMe | O | H |
| 82A | 4-F | 4-Br | n-Bu | COOMe | O | H |
| 83A | 4-OCF₃ | 4-Br | Me | COOMe | O | H |
| 84A | 4-F | 4-I | n-Bu | COOMe | O | H |
| 85A | 4-F | 4-CN | n-Bu | COOMe | O | H |
| 86A | 4-OCF₃ | 4-Cl | Me | COOMe | O | H |
| 87A | 4-F | 4-SMe | n-Bu | COOMe | O | H |
| 88A | 4-F | 4-CF₃ | n-Bu | COOMe | O | H |
| 89A | 4-F | 4-Br | Me | COOMe | O | H |
| 90A | 4-Cl | 4-Br | Me | COOMe | O | H |
| 91A | 4-OCF₃ | 4-CF₃ | Me | COMe | O | H |
| 92A | 4-OCF₃ | 4-Br | Me | COOMe | O | H |
| 93A | 4-OCF₃ | 4-CN | Me | COOMe | O | H |
| 94A | 4-Cl | 4-Br | CH₂C₆H₅ | COOMe | O | H |
| 95A | 4-Cl | 4-F | CH₂C₆H₅ | COOMe | O | H |
| 96A | 4-Cl | 4-OCF₃ | CH₂C₆H₅ | COOMe | O | H |
| 97A | 4-Br | 4-Br | Me | COOMe | O | H |
| 98A | 4-Br | 4-CF₃ | Me | COOMe | O | H |
| 99A | 4-Br | 4-CN | Me | COOMe | O | H |
| 100A | 4-Br | 4-CF₃ | Me | COOMe | O | H |
| 101A | 4-Br | 4-Br | Me | COOMe | O | H |
| 102A | 4-Br | 4-OCF₃ | Me | COOMe | O | H |
| 103A | 4-Br | 4-Cl | Me | COOMe | O | H |
| 104A | 4-Cl | 4-CF₃ | Me | COOt-Bu | O | Me |
| 105A | 4-OCF₃ | 4-CF₃ | Me | COOMe | O | n-Pr |
| 106A | 4-CF₃ | 4-CF₃ | Me | COOMe | O | n-Pr |
| 107A | 4-Br | 4-CF₃ | Me | CONHC₆H₄(p-CF₃) | O | H |
| 108A | 4-Br | 4-Br | Me | CONHC₆H₄(p-Br) | O | H |
| 109A | 4-Br | 4-OCF₃ | Me | CONC₆H₄(p-OCF₃) | O | H |
| 110A | 4-Cl | 4-CN | allyl | COOMe | O | H |
| 111A | 4-Cl | 4-SMe | allyl | COOMe | O | H |
| 112A | 4-Cl | 4-CF₃ | allyl | COOMe | O | H |
| 113A | 4-Cl | 4-CF₃ | allyl | COOMe | O | Me |
| 114A | 4-Cl | 4-CF₃ | allyl | COOMe | O | n-Pr |
| 115A | 4-Cl | 4-Br | allyl | COOMe | O | Me |
| 116A | 4-F | 4-CF₃ | Me | COOMe | S | H |
| 117A | 4-Cl | 4-CF₃ | Me | COOMe | S | H |
| 118A | 4-Cl | 4-CF₃ | Me | COOMe | S | Me |
| 119A | 4-F | 4-OCF₃ | n-Bu | COOMe | S | H |
| 120A | 4-F | 4-CF₃ | Me | COOMe | O | n-Pr |
| 121A | 4-Cl | 4-CF₃ | Me | COOMe | O | n-Pr |
| 122A | 4-Cl | 4-Br | allyl | COOEt | O | H |
| 123A | 4-Cl | 4-OCF₃ | Me | COOMe | O | Me |
| 124A | 4-Cl | 4-I | Me | COOMe | O | H |
| 125A | 4-OCF₃ | 4-OCF₃ | Me | COOt-Bu | O | H |
| 126A | 4-OCF₃ | 4-CF₃ | Me | COOt-Bu | O | Me |
| 127A | 4-Br | 4-CF₃ | Me | COOt-Bu | O | Me |
| 128A | 4-Br | 4-Br | Me | COOt-Bu | O | H |

TABLE 7-continued

| Compound # | R2 | R1 | B | A | X | Y |
|---|---|---|---|---|---|---|
| 129A | 4-Br | 4-OCF3 | Me | COOt-Bu | O | H |
| 130A | 4-OCF3 | 4-Br | Me | COOt-Bu | O | H |
| 131A | 4-Br | 4-CF3 | Me | COOt-Bu | O | H |
| 132A | 4-Br | 4-OCF | Me | COOt-Bu | O | H |

EXAMPLE 32

Fall Armyworm

Test units, each consisting of an 8-ounce plastic cup containing a layer of wheat germ diet, approximately 0.5 cm thick, were prepared. Ten third-instar larvae of fall armyworm (*Spodoptera frugiperda*) were placed into each cup. Solutions of each of the test compounds (acetone/distilled water 75/25 solvent) were sprayed onto the cups, a single solution per set of three cups. Spraying was accomplished by passing the cups, on a conveyer belt, directly beneath a flat fan hydraulic nozzle which discharged the spray at a rate of 0.5 pounds of active ingredient per acre (about 0.55 kg/ha) at 30 p.s.i. The cups were then covered and held at 27° C. and 50% relative humidity for 72 hours, after which time mortality readings were taken.

Of the compounds tested on fall armyworm, the following resulted in greater than or equal to 80% mortality:

1, 3, 4, 5, 6, 10, 11, 12, 14, 16, 17, 18, 20, 23, 26, 27, 29, 30, 31, 32, 33, 34, 36, 40, 41, 42, 44, 45, 46, 47, 48, 50, 51, 54, 59, 65, 67, 68, 69, 71, 74, 77, 86, 89, 90, 95, 96, 113, 116, 119, 132, 134, 135, 137, 138, 141, 162, 164, 166, 170, 172, 174, 176, 180, 184, 193, 195, 197, 200, 202, 203, 206, 221, 222, 223, 224, 225, 229, 231, 249, 253, 254, 255, 270, 303, 304, 305, 306, 307, 351, 352, 354, 357, 363, 364, 410, 411, 412, 414, 415, 417, 427, 430 from Table 6 and 7A, 9A, 13A, 46A, 50A, 51A 53A 61A, 62A, 83A, 100A, 102A, 103A from Table 7.

EXAMPLE 33

Tobacco Budworm

The test procedure of Example 32 was repeated for efficacy against third-instar larvae of the tobacco budworm (*Heliothis virescens*) except that mortality was assessed at 48 hours. Of the compounds tested on tobacco budworm, the following resulted in greater than or equal to 80% mortality:

1, 4, 5, 6, 11, 15, 23, 26, 27, 29, 30, 32, 41, 43, 45, 51, 54, 59, 65, 68, 69, 77, 96, 138, 172, 221, 222, 223, 225, 229, 249, 253, 303, 304, 305, 351, 352, 356, 358, 410, 411, 412, 414, 415, 417, 427, 430, from Table 6 and 7A, 40A, 46A, 54A, 62A, 83A, 100A, 102A, 103A from Table 7.

EXAMPLE 34

European Corn Borer

Test units, each consisting of an 8-ounce plastic cup containing a one-inch square of wheat germ/soyflour diet were prepared. Five third-instar larvae of the European corn borer (*Ostrinia nubilalis*) were placed into each cup. Sets of three test units were sprayed as described in Example 32 with individual solutions of the test compounds. The cups were then covered and held at 27° C. and 50% relative humidity for 48 hours, after which time mortality readings were taken. Of the compounds tested on European corn borer, the following resulted in greater than or equal to 80% mortality:

1, 5, 6, 18, 23, 30, 32, 33, 34, 40, 41, 42, 43, 44, 45, 46, 48, 50, 51, 59, 65, 68, 74, 86, 89, 95, 96, 116, 132, 134, 135, 138, 141, 164, 172, 176, 178, 197, 203, 211, 222, 224, 225, 227, 229, 231, 237, 249, 251, 254, 303, 304, 305, 351, 352, 354, 364, 410, 411, 412, 414, 415, 417, 427, 430, from Table 6 and 1A, 2A, 7A, 13A, 18A, 40A, 43A, 46A, 51A, 53A, 54A, 74A, 100A, 102A, 103A from Table 7.

EXAMPLE 35

Southern Corn Rootworm

Test units, each consisting of an 8-ounce plastic cup containing 1 sprouted corn seed, were prepared. Sets of three test units were sprayed as described in Example 32 with individual solutions of the test compounds. After the spray on the cups had dried, five third-instar larvae of the southern corn rootworm (*Diabrotica undecimpunctata howardi*) were placed into each cup. A moistened dental wick was inserted into each cup to prevent drying and the cups were then covered. The cups were then held at 27° C. and 50% relative humidity for 48 hours, after which time mortality readings were taken.

Of the compounds tested on southern corn rootworm, the following resulted in greater than or equal to 80% mortality:

5, 6, 11, 12, 16, 17, 18, 23, 26, 29, 30, 31, 32, 34, 41, 43, 44, 45, 46, 48, 51, 74, 77, 86, 89, 90, 96, 132, 138, 141, 172, 221, 225, 303, 304, 351, 352, 354, 364, 410, 412, 414, 415, 417, 427, 430 from Table 6 and 7A, 9A, 13A, 17A, 34A, 46A, 50A, 51A, 53A, 54A, 62A, 74A, 83A, 100A, 102A, 103A, from Table 7.

EXAMPLE 36

Boll Weevil

Five adult boll weevils (*Anthonomus grandis*) were placed into each of a series of 9-ounce cups. The test procedure employed was then otherwise the same as in Example 32 with three cups per treatment. Mortality readings were taken 48 hours after treatment.

Of the compounds tested on boll weevil, the following resulted in greater than or equal to 80% mortality:

5, 6, 11, 12, 18, 22, 23, 24, 26, 30, 31, 32, 33, 34, 40, 41, 42, 43, 44, 45, 46, 51, 54, 59, 63, 66, 67, 68, 77, 89, 90, 95, 96, 116, 117, 132, 134, 137, 138, 139, 141, 162, 166, 172, 174, 176, 179, 181, 183, 203, 206, 217, 221, 222, 225, 227, 229, 249, 253, 270, 302, 303, 304, 305, 307, 351, 352, 410, 412, 414, 415, 417, 430 from Table 6 and 2A, 6A, 7A, 9A, 13A, 34A, 46A, 50A, 51A, 54A, 62A, 71A, 100A, 102A, 103A, from Table 7.

EXAMPLE 37

Aster Leafhopper

Test units were prepared from a series of 12-ounce cups, each containing oat (*Avena sativa*) seedlings in a 1-inch layer of sterilized soil. Sets of three test units were sprayed as described in Example 32 with individual solutions of the test compounds. After the oats had dried from the spraying, between 10 and 15 adult aster leafhoppers (*Mascrosteles fascifrons*) were aspirated into each of the covered cups. The cups were held at 27° C. and 50% relative humidity for 48 hours, after which time mortality readings were taken.

Of the compounds tested on aster leafhopper, the following resulted in greater than or equal to 80% mortality:

5, 6, 23, 32, 34, 41, 43, 45, 50, 69, 96, 221, 303, 304, 351, 352, 410, 415, 417, from Table 6 and 7A, 13A, 46A, 51A, 53A, 54A, 62A, 74A, 100A, 102A, 103A from Table 7.

EXAMPLE 38

Combinations with Spray Oils

Both short-term and residual insecticidal activity of the tested compound (Compound 30) against fall armyworm, Spodoptera frugiperda, was improved when the emulsifiable concentrate formulation of the compound was combined with spray oils or spray oil concentrates.

The test compound was diluted in 5 ml of acetone and then mixed with distilled water to 100 and 50 ppm. Spray oil or spray oil concentrate was added to the solutions in the ratio 10:1 oil:active ingredient. The spray oil was a paraffinic petroleum-based oil having a median distillation temperature at atmospheric pressure of 377° C. The spray oil concentrate consisted of 83% isoparaffinic oil and 17% of a mixture of sorbitol ester and epoxylated sorbitol ester. Test units consisted of 3 week-old soybean plants growing in 4 inch pots. Three plants were sprayed to runoff on a turntable sprayer at 10 rpm with an atomizing nozzle for each treatment.

After the spray dried, treated leaflets were cut in half and each piece was placed in one well of a 6-cell tissue culture plate. One third instar larva was placed in each cell. The entire unit was then capped with a piece of moistened blotter paper. Four such units were set up for each treatment. Test units were held at 27° C. and 50% relative humidity. Mortality was assessed at 72 hours. Treated plants were held at 27° C. and 50% relative humidity and the test was repeated at 7 and 14 days to determine residual activity.

The results are recorded in Table 8.

TABLE 8

| Compound 30 With and Without Spray Oil or Spray Oil Concentrate | | | | |
|---|---|---|---|---|
| | | % MORTALITY | | |
| TREATMENT | RATE (PPM) | DAY 0 | DAY 7 | DAY 14 |
| Compound 30 + | 100 | 100 | 100 | 100 |
| Spray Oil | 50 | 100 | 96 | 96 |
| Concentrate | | | | |
| Compound 30 + | 100 | 100 | 100 | 100 |
| Spray Oil | 50 | 100 | 100 | 100 |
| Compound 30 | 100 | 100 | 83 | 50 |
| (without oil) | 50 | 100 | 83 | 46 |

EXAMPLE 39

Improved Activity with Synergists

Test units were prepared as described in Example 32 using 5 fall armyworm larvae, Spodoptera frugiperda. Prior to treatment with the test compound (Compound 30), the units were oversprayed with the piperonyl butoxide (PBO) at a rate 5X the concentration to be used for the test compound, using the technique described in Example 32. After 2.5 hours, the units were oversprayed with the test compound at 10, 5, 2.5, 1.0, 0.5 and 0.1 ppm. The test units were covered and held for 72 hours at 27° C. and 50% relative humidity after which time mortality was assessed. The results are recorded in Table 9.

TABLE 9

| Effect of Adding Piperonyl Butoxide | | |
|---|---|---|
| | % MORTALITY | |
| RATE (PPM) | WITHOUT PBO | WITH PBO 5:1 |
| 10 | 100 | 100 |
| 5 | 100 | 100 |
| 2.5 | 96 | 100 |
| 1.0 | 96 | 96 |
| 0.5 | 44 | 80 |
| 0.1 | 20 | 80 |

The embodiments of the invention in which an exclusive property or privilege is claimed are defined as follows:

What is claimed:

1. A compound having the following formula, and agriculturally suitable salts thereof:

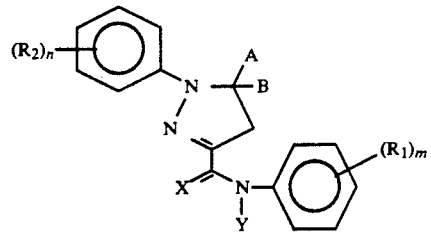

wherein:

X is O or S;

Y is H, $C_1$ to $C_4$ alkyl, $C_2$ to $C_4$ alkoxyalkyl, $C_1$ to $C_4$ alkylthio, $C_1$ to $C_4$ haloalkylthio, phenylthio, or phenylthio substituted with 1 to 3 substituents independently selected from W, $C_2$ to $C_4$ alkoxycarbonyl, C(O)H, $C_2$ to $C_4$ alkylcarbonyl or $C_2$ to $C_4$ haloalkylcarbonyl;

A is H, $C_1$ to $C_6$ alkyl, phenyl, phenyl substituted by $(R_5)_p$, CN, $CO_2R_3$, $C(O)R_3$, $C(O)NR_3R_4$, $C(S)NR_3R_4$, $C(S)R_3$ or $C(S)SR_3$;

B is H, $C_1$ to $C_6$ alkyl, $C_1$ to $C_6$ haloalkyl, $C_2$ to $C_6$ alkoxyalkyl, $C_2$ to $C_6$ cyanoalkyl, $C_3$ to $C_8$ alkoxycarbonylalkyl, $C_2$ to $C_6$ alkenyl, $C_2$ to $C_6$ alkynyl, $C_2$ to $C_6$ alkoxycarbonyl, phenyl, phenyl substituted with 1 to 3 substituents independently selected from W, benzyl or benzyl substituted with 1 to 3 substituents independently selected from W;

W is halogen, CN, $NO_2$, $C_1$ to $C_2$ alkyl, $C_1$ to $C_2$ haloalkyl, $C_1$ to $C_2$ alkoxy, $C_1$ to $C_2$ haloalkoxy, $C_1$ to $C_2$ alkylthio, $C_1$ to $C_2$ haloalkylthio, $C_1$ to $C_2$ alkylsulfonyl or $C_1$ to $C_2$ haloalkylsulfonyl;

$R_1$, $R_5$ and $R_5$ are independently $R_3$, halogen, CN, $N_3$, SCN, $NO_2$, $OR_3$, $SR_3$, $S(O)R_3$, $S(O)_2R_3$, $OC(O)R_3$, $OS(O)_2R_3$, $CO_2R_3$, $C(O)R_3$, $C(O)NR_3R_4$, $S(O)_2NR_3R_4$, $NR_3R_4$, $NR_4C(O)R_3$, $OC(O)NHR_3$, $NR_4C(O)NHR_3$, $NR_4S(O)_2R_3$, or when m, n or p is 2, $R_1$, $R_2$ or $R_5$, individually can be taken together as $-OCH_2O-$, $-OCF_2O-$, $-OCH_2CH_2O-$, $-CH_2C(CH_3)_2O-$, $-OCF_2CF_2O-$, or $-CF_2CF_2O-$ to form a cyclic bridge; provided $R_1$ is never H or $C_1$ to $C_4$ alkyl;

$R_3$ is H, $C_1$ to $C_4$ alkyl, $C_1$ to $C_4$ haloalkyl, $C_2$ to $C_4$ alkenyl, $C_2$ to $C_4$ haloalkenyl, $C_2$ to $C_4$ alkynyl, $C_2$ to $C_4$ haloalkynyl, $C_2$ to $C_4$ alkoxyalkyl, $C_2$ to C$_4$ alkylthioalkyl, C$_1$ to C$_4$ nitroalkyl, C$_2$ to C$_4$ cyanoalkyl, C$_3$ to C$_6$ alkoxycarbonylalkyl, C$_3$ to C$_6$ cycloalkyl, C$_3$ to C$_6$ halocycloalkyl, phenyl, benzyl, or phenyl or benzyl substituted with 1 to 3 substituents independently selected from W;

R$_4$ is H or C$_1$ to C$_4$ alkyl, or when R$_3$ and R$_4$ are attached to a single nitrogen atom, they can be taken together as (CH$_2$)$_4$, (CH$_2$)$_5$ or (CH$_2$CH$_2$OCH$_2$CH$_2$);

m is 1 to 3;
n is 0 to 3; and
p is 0 to 3.

2. A compound according to claim 1 wherein
X is O;
Y is H, CH$_3$, SCH$_3$, SCCl$_3$, SC$_6$H$_5$, 2-(NO$_2$)C$_6$H$_4$S, C(O)CH$_3$, C(O)H, C(O)CF$_3$, CO$_2$CH$_3$ or CO$_2$C$_2$H$_5$;
R$_3$ is C$_1$ to C$_4$ alkyl, C$_1$ to C$_2$ haloalkyl, C$_2$ to C$_4$ alkenyl, C$_2$ to C$_4$ haloalkenyl, propargyl, phenyl, benzyl, or phenyl or benzyl substituted with one of F, Cl, Br, CF$_3$, OCF$_2$H, OCF$_3$ or NO$_2$;
n is 0 to 2;
p is 0 to 2; and
m is 1 to 2.

3. A compound according to claim 2 wherein
R$_1$ is halogen, CN, SCN, NO$_2$, R$_3$, OR$_3$, SR$_3$, S(O)$_2$R$_3$, CO$_2$R$_3$ or C(O)R$_3$, or when m is 2, R$_1$ can be taken together as —OCF$_2$O—, —CH$_2$C(CH$_3$)$_2$O—, —OCF$_2$CF$_2$O— or —CF$_2$CF$_2$O—;
R$_2$ and R$_5$ are independently halogen, CN, SCN, NO$_2$, R$_3$, OR$_3$, SR$_3$, S(O)$_2$R$_3$, OC(O)R$_3$, OS(O)$_2$R$_3$, CO$_2$R$_3$, C(O)R$_3$, C(O)NR$_3$R$_4$, S(O)$_2$NR$_3$R$_4$ or NR$_3$R$_4$;
R$_3$ is C$_1$ to C$_4$ alkyl, C$_1$ to C$_2$ haloalkyl, C$_2$ to C$_4$ alkenyl, C$_2$ to C$_4$ haloalkenyl or propargyl;
R$_4$ is H or C$_1$ to C$_2$ alkyl;
A is C$_1$ to C$_4$ alkyl, phenyl, phenyl substituted with (R$_5$)$_p$, CO$_2$R$_3$, C(O)R$_3$, C(O)NR$_3$R$_4$ or C(O)NR$_4$. phenyl said phenyl optionally substituted with F, Cl, Br, CF$_3$, OCF$_2$H, OCF$_3$ or NO$_2$); and
B is H, C$_1$ to C$_4$ alkyl, C$_1$ to C$_4$ haloalkyl, or C$_3$ to C$_4$ alkenyl.

4. A compound according to claim 3 wherein
Y is H, CH$_3$, C(O)CH$_3$ or CO$_2$CH$_3$;
m is 1 or 2 and one substituent is in the 4-position of the phenyl ring;
n is 1 or 2 and one substituent is in the 4-position of the phenyl ring;
p is 1 or 2 and one substituent is in the 3 or 4-position of the phenyl ring;
R$_1$ is F, Cl, Br, CF$_3$, OCF$_2$H, OCF$_3$ or CN, or when m is 2, R$_1$ can be taken together as —CH$_2$C(CH$_3$)$_2$O— or —CF$_2$CF$_2$O—;
R$_2$ is F, Cl, Br, CN, NO$_2$, CF$_3$, CH$_3$, OCH$_3$, OCF$_2$H, OCF$_3$, SCH$_3$, SCF$_2$H, S(O)$_2$CH$_3$ or N(CH$_3$)$_2$;
R$_5$ is F, Cl, Br, CN, NO$_2$, CF$_3$, CH$_3$, OCH$_3$, OCF$_2$H, OCF$_3$, SCH$_3$, SCF$_2$H, S(O)$_2$CH$_3$, S(O)$_2$CF$_2$H, CO$_2$CH$_3$, C(O)NHCH$_3$, C(O)N(CH$_3$)$_2$, S(O)$_2$N(CH$_3$)$_2$ or N(CH$_3$)$_2$;
A is phenyl or phenyl substituted with (R$_5$)$_p$; and
B is H or CH$_3$.

5. A compound according to claim 3 wherein
Y is H, CH$_3$, C(O)CH$_3$ or CO$_2$CH$_3$;
m is 1 or 2 and one substituent is in the 4-position of the phenyl ring;
n is 1 or 2 and one substituent is in the 4-position of the phenyl ring;
R$_1$ is F, Cl, Br, CF$_3$, OCF$_2$H, OCF$_3$ or CN, or when m is Z, R$_1$ can be taken together as —CH$_2$(CH$_3$)$_2$O— or CF$_2$CF$_2$O—;
R$_2$ is F, Cl, Br, CN, NO$_2$, CF$_3$, CH$_3$, OCH$_3$, OCF$_2$H, OCF$_3$, SCH$_3$, SCF$_2$H, S(O)$_2$CH$_3$, S(O)$_2$CF$_2$H, CO$_2$CH$_3$, C(O)NHCH$_3$, C(O)N(CH$_3$)$_2$, S(O)$_2$N(CH$_3$)$_2$ or N(CH$_3$)$_2$;
A is CO$_2$CH$_3$, CO$_2$C$_2$H$_5$, C(O)NHCH$_3$ or C(O)N(CH$_3$)$_2$; and
B is CH$_3$.

6. A compound according to claim 5: methyl 1-(4-chlorophenyl)-4,5-dihydro-5-methyl-3-[[4-(trifluoromethyl)phenyl]aminocarbonyl]-1H-pyrazole-5-carboxylate.

7. A compound according to claim 4: 1-(4-chlorophenyl)-5-(4-fluorophenyl)-4,5-dihydro-N-[4-(trifluoromethyl)phenyl]-1H-pyrazole-3-carboxamide.

8. A compound according to claim 4: 1,5-bis(4-chlorophenyl)-4,5-dihydro-N-[4-(trifluoromethyl)-phenyl]-1H-pyrazole-3-carboxamide.

9. A compound of according to claim 4: 1-(4-chlorophenyl)-5-(4-cyanophenyl)-4,5-dihydro-N-[4-(trifluoromethyl)phenyl]-1H-pyrazole-3-carboxamide.

10. A composition comprising an insecticidally effective amount of a compound according to claim 1 and an agriculturally suitable carrier therefor.

11. A composition comprising an insecticidally effective amount of a compound according to claim 2 and an agriculturally suitable carrier therefor.

12. A composition comprising an insecticidally effective amount of a compound according to claim 3 and an agriculturally suitable carrier therefor.

13. A composition comprising an insecticidally effective amount of a compound according to claim 4 and an agriculturally suitable carrier therefor.

14. A composition comprising an insecticidally effective amount of a compound according to claim 5 and an agriculturally suitable carrier therefor.

15. A method of controlling insects comprising contacting them with an effective amount of a compound according to claim 1.

16. A method of controlling insects comprising contacting them with an effective amount of a compound according to claim 2.

17. A method of controlling insects comprising contacting them with an effective amount of a compound according to claim 3.

18. A method of controlling insects comprising contacting them with an effective amount of a compound according to claim 4.

19. A method of controlling insects comprising contacting them with an effective amount of a compound according to claim 5.

20. A composition according to claim 10 comprising additionally a spray oil or spray oil concentrate.

21. A method for controlling insects comprising contacting them with an effective amount of a composition according to claim 20.

* * * * *